(12) United States Patent
Lu et al.

(10) Patent No.: US 7,612,185 B2
(45) Date of Patent: *Nov. 3, 2009

(54) NUCLEIC ACID BIOSENSORS

(75) Inventors: Yi Lu, Champaign, IL (US); Juewen Liu, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 510 days.

This patent is subject to a terminal disclaimer.

(21) Appl. No.: 10/384,497

(22) Filed: Mar. 7, 2003

(65) Prior Publication Data

US 2004/0175693 A1    Sep. 9, 2004

(51) Int. Cl.
*C12N 15/11* (2006.01)
*C12Q 1/68* (2006.01)
*A61K 31/70* (2006.01)
*A01N 43/04* (2006.01)

(52) U.S. Cl. ............... 536/23.1; 536/24.5; 514/44; 435/6; 435/325; 435/375

(58) Field of Classification Search ........... 536/23.1, 536/24.5; 435/4, 6; 514/44
See application file for complete search history.

(56) References Cited

U.S. PATENT DOCUMENTS

| | | | |
|---|---|---|---|
| 4,703,017 A | 10/1987 | Campbell et al. | |
| 4,855,240 A | 8/1989 | Rosenstein et al. | |
| 5,459,040 A | 10/1995 | Hammock et al. | |
| 5,472,881 A | 12/1995 | Beebe et al. | |
| 5,580,967 A | 12/1996 | Joyce | |
| 5,593,835 A | 1/1997 | Rando et al. | |
| 5,631,148 A | 5/1997 | Urdea | |
| 5,663,064 A | 9/1997 | Burke et al. | |
| 5,807,718 A | 9/1998 | Joyce et al. | |
| 5,807,967 A | 9/1998 | Snow et al. | |
| 5,910,408 A | 6/1999 | Szostak et al. | |
| 5,989,813 A | 11/1999 | Gerdes | |
| 6,040,138 A | 3/2000 | Lockhart et al. | |
| 6,110,462 A | 8/2000 | Barbas et al. | |
| 6,287,765 B1 * | 9/2001 | Cubicciotti | 435/6 |
| 6,316,194 B1 | 11/2001 | Karn et al. | |
| 6,361,944 B1 | 3/2002 | Mirkin et al. | |
| 6,451,535 B1 | 9/2002 | Jenne et al. | |
| 6,485,982 B1 | 11/2002 | Charlton | |
| 6,541,617 B1 | 4/2003 | Bamdad et al. | |
| 6,630,306 B1 | 10/2003 | Breaker | |
| 6,706,474 B1 | 3/2004 | Lu et al. | |
| 6,818,455 B2 | 11/2004 | May et al. | |
| 6,849,414 B2 | 2/2005 | Guan et al. | |
| 6,890,719 B2 | 5/2005 | Lu et al. | |
| 7,192,708 B2 | 3/2007 | Lu et al. | |
| 2003/0215810 A1 | 11/2003 | Lu et al. | |
| 2004/0018515 A1* | 1/2004 | Diener et al. | 435/6 |
| 2004/0126882 A1 | 7/2004 | Ellington et al. | |
| 2004/0175693 A1 | 9/2004 | Lu et al. | |
| 2005/0136500 A1 | 6/2005 | Yang et al. | |
| 2005/0282186 A1 | 12/2005 | Lu et al. | |
| 2006/0019406 A1 | 1/2006 | Wei et al. | |
| 2006/0094026 A1 | 5/2006 | Lu et al. | |
| 2006/0166222 A1 | 7/2006 | Lu et al. | |
| 2007/0037171 A1 | 2/2007 | Lu et al. | |
| 2007/0269821 A1 | 11/2007 | Mazumdar et al. | |
| 2008/0176228 A1 | 7/2008 | Lu et al. | |

FOREIGN PATENT DOCUMENTS

| | | |
|---|---|---|
| EP | 121970 | 10/1984 |
| EP | 1219708 | 7/2002 |
| EP | 1 312 674 | 5/2003 |
| GB | 2339280 | 1/2000 |
| WO | WO 96/17086 | 6/1996 |
| WO | WO 97/09342 | 3/1997 |
| WO | WO 98/04740 | 2/1998 |
| WO | WO 98/27104 | 6/1998 |
| WO | WO 98/39484 | 9/1998 |
| WO | WO 98/49346 | 11/1998 |
| WO | WO 99/13338 | 3/1999 |
| WO | WO 99/27351 | 6/1999 |
| WO | WO 99/47704 | 9/1999 |
| WO | WO 00/26226 | 5/2000 |
| WO | WO 00/58505 | 10/2000 |
| WO | WO 01/00876 | 1/2001 |
| WO | WO 01/23548 | 4/2001 |
| WO | WO 01/24696 | 4/2001 |
| WO | WO 01/27612 A2 | 4/2001 |
| WO | WO 01/27612 A3 | 4/2001 |
| WO | WO 01/51665 | 7/2001 |
| WO | WO 01/73123 | 10/2001 |

(Continued)

OTHER PUBLICATIONS

Tanner et al. Transfection of human endothelial cells, 1997, Cardiovascular Research, vol. 35, pp. 522-528.*
Ronald R Breaker, DNA aptamers and DNA enzymes, 1997, Current Opinion in Chemical Biology, vol. 1, pp. 26-31.*
Fahlman et al., DNA conformational switches as sensitive electronic sensors of analytes, 2002, JACS, vol. 124, pp. 4610-4616.*
Allara D, Nuzzo R., "Spontaneously organized molecular assemblies. 1. Formation, dynamics and physical properties of n-alkanoic acids adsorbed from solution on an oxidized aluminum surface," *Langmuir* 1:45-52 (1985).
Andreola, M., F. Pileur, C. Calmels, M. Ventur, et al., "DNA aptamers selected against the HIV-1 RNase H display in vitro antiviral activity," *Biochemistry*, 40:10087-94 (2001).
Been, M. and G. Wickham, "Self-cleaving ribozymes of hepatitis delta virus RNA," *Eur. J. Biochem.*, 247:741-53 (1997).

(Continued)

*Primary Examiner*—J. E. Angell
*Assistant Examiner*—Dana Shin
(74) *Attorney, Agent, or Firm*—Evan Law Group LLC

(57) ABSTRACT

Sensors comprising aptazymes capable of detecting the presence and concentration of effectors, as well as methods of using such sensors, are disclosed.

20 Claims, 8 Drawing Sheets

FOREIGN PATENT DOCUMENTS

| WO | WO 02/00006 | 1/2002 |
|---|---|---|
| WO | WO 02/22882 | 3/2002 |
| WO | WO 02/098364 | 12/2002 |
| WO | WO 03/062422 | 7/2003 |
| WO | WO 03/068963 | 8/2003 |
| WO | WO 03/094838 | 11/2003 |
| WO | WO 03/095648 | 11/2003 |
| WO | WO 2004/081235 | 9/2004 |
| WO | WO 2005/095967 | 10/2005 |
| WO | WO 2005/100602 | 10/2005 |
| WO | WO 2006/048164 | 5/2006 |
| WO | WO 2006/052419 | 5/2006 |
| WO | WO 2006/078660 | 7/2006 |
| WO | WO 2007/106118 | 9/2007 |
| WO | WO 2007/109500 | 9/2007 |
| WO | WO 2008/089248 | 7/2008 |

OTHER PUBLICATIONS

Biroccio A, J. Hamm, I. Incitti, R. De Francesco, and L. Tomei,. "Selection of RNA aptamers that are specific and high-affinity ligands of the hepatitis C virus RNA-dependent RNA polymerase," *J Virol* 76:3688-3696 (2002).

Bock, L., L. Griffin, J. Latham,, E. Vermaas, and J. Toole, "Selection of single-stranded DNA molecules that bind and inhibit human thrombin," *Nature*, (London) 355:564-6 (1992).

Breaker R. and G. Joyce, "A DNA enzyme that cleaves RNA," *Chem Biol.*, 1:223-229 (1994).

Breaker R., "Engineered allosteric ribozymes as biosensor components," *Curr Opin Biotechnol.*, 13:31-39 (2002).

Breaker R., and G. Joyce, "A DNA enzyme with Mg(2+)-dependent RNA phosphoesterase activity.; A DNA enzyme that cleaves RNA," *Chem Biol; Chem Biol* 2 (10):655-60.

Breaker, R., "DNA enzymes," *Nat. Biotechnol.* 15:427-31 (1997).

Breaker, R., "Catalytic DNA: in training and seeking employment," *Nat. Biotechnol.*,17:422-3 (1999).

Breaker, R., "Making catalytic DNAs," *Science*, 290:2095-2096 (2000).

Brody, E. and L. Gold, "Aptamers as therapeutic and diagnostic agents," *J Biotechnol.*, 74:5-13 (2000).

Brown, A., C. Pavot, J. Li, and Y. Lu, "A lead-dependent DNAzyme with a two-step mechanism," Biochemistry 2003, 42:7152-7161 *Submitted* (2003).

Bruno, J. and J. Kiel, "In vitro selection of DNA aptamers to anthrax spores with electrochemiluminescence detection," *Biosens Bioelectron* 14:457-464 (1999).

Bruno, J. and J. Kiel, "Use of magnetic beads in selection and detection of biotoxin aptamers by electrochemiluminescence and enzymatic methods," *Biotechniques*, 32:178-80, 182-3 (2002).

Burgstaller, P. and M. Famulok, "Isolation of RNA aptamers for biological cofactors by in vitro selection," *Angew. Chem.*, 106:1163-6 (See also Angew. Chem., Int. Ed. Engl., 994, 33(10), 084-7) (1994).

Burgstaller, P., M. Kochoyan, and M. Famulok, "Structural probing and damage selection of citrulline- and arginine-specific RNA aptamers identify base positions required for binding," *Nucleic Acids Res.*, 23:4769-76 (1995).

Burke, D. and L. Gold, "RNA aptamers to the adenosine moiety of S-adenosyl methionine: structural inferences from variations on a theme and the reproducibility of SELEX," *Nucl. Acids Res.*, 25:2020-2024 (1997).

Burke, D., D. Hoffman, A. Brown, M. Hansen, et al., "RNA aptamers to the peptidyl transferase inhibitor chloramphenicol," *Chem. Biol.* 4:833-43 (1997).

Burmeister, J., Von Kiedrowski, G. & Ellington, A.D. (1997). Cofactor-assisted self-cleavage in DNA libraries with a 3'-'5'-phosphoramidate bond. *Angew. Chem., Int. Ed. Engl.* 36:1321-4.

Cadwell, R. and G. Joyce, "Mutagenic PCR," *PCR Methods Appl.*, 3:S136-S140 (1994).

Cadwell, R. and G. Joyce, "Randomization of genes by PCR mutagenesis," *PCR Methods Appl.*, 2:28-33 (1992).

Cao, Y, R. Jin, and C. Mirkin, "DNA-modified core-shell Ag/Au particles," *J. Am. Chem. Soc.*, 123:7961-7962 (2001).

Carmi, N., H. Balkhi, and R. Breaker, "Cleaving DNA with DNA," *Proc. Natl. Acad. Sci. U. S. A.* 95:2233-7 (1998).

Carmi, N., L. Shultz, and R. Breaker, "In vitro selection of self-cleaving DNAs," *Chem. Biol.*, 3:1039-1046 (1996).

Cech, T. and D. Herschlag, "Group I ribozymes: substrate recognition, catalytic strategies, and comparative mechanistic analysis," *Nucl. Acids Mol. Biol.* 10:1-17 (1996).

Cech, T., Structure and mechanism of the large catalytic RNAs: group I and group II introns and ribonuclease P, *In The RNA World* (Gesteland, R.F. & Atkins, J.F., ed.), pp. 239-70, Cold Spring Harbor Laboratory Press, Cold Spring Harbor, New York (1993).

Chaloin, L., M. Lehmann, G. Sczakiel, and T. Restle, "Endogenous expression of a high-affinity pseudoknot RNA aptamer suppresses replication of HIV-1," *Nucl. Acids Res.*, 30:4001-4008 (2002).

Chapman, K. and J. Szostak, "In vitro selection of catalytic RNAs," *Curr. Opin. Struct. Biol.*, 4:618-622 (1994).

Ciesiolka, J., J. Gorski, and M. Yarus, "Selection of an RNA domain that binds Zn2+," *RNA*, 1:538-550 (1995).

Conaty, J., P. Hendry, and T. Lockett, "Selected classes of minimised hammerhead ribozyme have very high cleavage rates at low Mg2+ concentration," *Nucl. Acids Res.*, 27:2400-2407 (1999).

Conn, M., J. Prudent, and P. Schultz, "Porphyrin Metallation Catalyzed by a Small RNA Molecule," *J. Am. Chem. Soc.*, 118:7012-7013 (1996).

Connell, G. and M. Yarus, "RNAs with dual specificity and dual RNAs with similar specificity," *Science*, 264:1137-1141(1994).

Connell, G., M. Illangesekare, and M. Yarus, "Three small ribooligonucleotides with specific arginine sites," *Biochemistry*, 32:5497-502 (1993).

Cuenoud, B. and J. Szostak, "A DNA metalloenzyme with DNA ligase activity," *Nature*, 375:611-614 (1995).

Dai X, De Mesmaeker A, Joyce GF. (1995) Cleavage of an amide bond by a ribozyme. *Science* 267:237-240.

DeRose, V., "Two Decades of RNA Catalysis," *Chem. & Biol.*, 9:961-969 (2002).

Earnshaw, G., "Modified oligoribonucleotides as site-specific probes of RAN structure and function," *Biopolymers*, 48:39-55 (1998).

Ekland, E. and D. Bartel, "RNA-catalysed RNA polymerization using nucleoside triphosphates," *Nature* 382:373-376 (1996).

Ekland, E., J. Szostak, and D. Bartel, "Structurally complex and highly active RNA ligases derived from random RNA sequences," *Science*, 269:364-370 (1995).

Ellington, A. and J. Szostak "In vitro selection of RNA molecules that bind specific ligands," *Nature*, 346:818-822 (1990).

Ellington, A. and R. Conrad, "Aptamers as potential nucleic acid pharmaceuticals," *Biotechnol. Annu. Rev.*, 1:185-214 (1995).

Ellington, A. and J. Szostak, "Selection in vitro of single-stranded DNA molecules that fold into specific ligand-binding structures," *Nature*, (London) 355:850-2 (1992).

Famulok, M. and A. Huettenhofer, "In Vitro Selection Analysis of Neomycin Binding RNAs with a Mutagenized Pool of Variants of the 16S rRNA Decoding Region," *Biochemistry*, 35:4265-70 (1996).

Famulok, M. and J. Szostak, "Stereospecific recognition of tryptophan agarose by in vitro selected RNA," *J. Am. Chem. Soc.*, 114:3990-3991 (1992).

Famulok, M., "Molecular Recognition of Amino Acids by RNA-Aptamers: An L-Citrulline Binding RNA Motif and Its Evolution into an L-Arginine Binder," *J. Am. Chem. Soc.*, 116:1698-706 (1994).

Famulok, M., "Oligonucleotide aptamers that recognize small molecules," *Curr. Opin. Struct. Biol.*, 9:324-329 (1999).

Faulhammer, D. and M. Famulok, "The $Ca^{2+}$Ion as a Cofactor for a Novel RNA-Cleaving Deoxyribozyme$_2$" *Angew Chem. Int, Ed. Engl.*, 35:2837-2841 (1997).

Fukusaki, E.-I., Kato, T., Maeda, H., Kawazoe, N., Ito, Y., Okazawa, A., Kajiyama, S.-I. & Kobayashi, A. (2000). DNA aptamers that bind to chitin. *Bioorg. Med. Chem. Lett.* 10:423-5.

Geiger, A., Burgstaller, P., Von Der Eltz, H., Roeder, A. & Famulok, M..(1996). RNA aptamers that bind L-arginine with sub-micromolar dissociation constants and high enantioselectivity. *Nucleic Acids Res.* 24:1029-36.

Geyer, C. and D. Sen, "Evidence for the metal-cofactor independence of an RNA phosphodiester-cleaving DNA enzyme," *Chem. Biol.* 4:579-593 (1997).

Giver, L., Bartel, D., Zapp, M., Pawul, A., Green, M. & Ellington, A.D. (1993). Selective optimization of the Rev-binding element of HIV-1. *Nucleic Acids Res.* 21:5509-16.

Giver, L., Bartel, D.P., Zapp, M.L., Green, M.R. & Ellington, A.D. (1993). Selection and design of high-affinity RNA ligands for HIV-1 Rev. *Gene* 137:19-24.

Grabar, K., R. Freeman, M. Homier, and M. Natan "Preparation and characterization of Au colloid Monolayers," *Anal. Chem.*, 67:735-743 (1995).

Haller, A. and P. Sarnow, "In vitro selection of a 7-methyl-guanosine binding RNA that inhibits translation of capped mRNA molecules," *Proc. Natl. Acad. Sci. USA*, 94:8521-6 (1997).

Harada, K. and A. Frankel, "Identification of two novel arginine binding DNAs," *EMBO J.*, 14:5798-5811 (1995).

Hesselberth, J., S. Robertson, S. Jhaveri, and A. Ellington, "In vitro. selection of nucleic acids for diagnostic applications," *J. Biotechnol.* 74:15-25 (2000).

Hofmann, H., S. Limmer, V. Hornung, and M. Sprinzl, "Ni2+-binding RNA motifs with an asymmetric purine-rich internal loop and a G-A base pair," *RNA*, 3:1289-1300 (1997).

Holeman, L., S. Robinson, J. Szostak, and C. Wilson, "Isolation and characterization of fluorophore-binding RNA aptamers," *Folding Des.* 3:423-31 (1998).

Huizenga, D. and J. Szostak, "A DNA aptamer that binds adenosine and ATP," *Biochemistry*, 34:656-665 (1995).

Iler, R, *In: The Surface Chemistry of Silica*. Wiley, New York, Chapter 6, 622-729 (1979).

Illangasekare, M. and M. Yarus, "Small-molecule-substrate interactions with a self-aminoacylating ribozyme," *J. Mol. Biol.*, 268:631-639 (1997).

Jayasena, S., "Aptamers: An Emerging Class of Molecules That Rival Antibodies in Diagnostics," *Clin. Chem.*, 45(9):1628-1650 (1999).

Jenison, R., S. Gill, A. Pardi, and B. Polisky, "High-resolution molecular discrimination by RNA," *Science*, 263:1425-9 (1994).

Jenison, R., S. Yang, A. Haeberli, and B. Polisky, "Interference-based detection of nucleic acid targets on optically coated silicon," *Nature Biotech.*, 19:62-65 (2001).

Jhaveri, S., M. Rajendran, and A. Ellington, "In vitro selection of signaling aptamers," *Nat. Biotechnol.*, 18:1293-1297 (2000).

Jhaveri, S., R. Kirby, R. Conrad, E. Maglott, M. Bowser, et al., "Designed signaling aptamers that transduce molecular recognition to changes in fluorescence intensity," *J. Am. Chem. Soc.*, 122:2469-2473 (2000).

Joyce, G., "In vitro evolution of nucleic acids," *Curr. Opin. Struct. Biol.*, 4:331-336 (1994).

Joyce, G., "Reactions Catalyzed by RNA and DNA Enzymes," *In The RNA World*, vol. 37 (Gesteland, R.F., Cech, T.R. & Atkins, J.F., ed.), pp. 687-689, Cold Spring Harbor Laboratory Press, Cold Spring Harbor, New York (1999).

Kato, T., T. Takemura, K. Yano, K. Ikebukuro, and I. Karube, "In vitro selection of DNA aptamers which bind to cholic acid," *Biochim. Biophys. Acta.*, 1493:12-8 (2000).

Kawakami, J., H. Imanaka, Y. Yokota, and N. Sugimoto, "In vitro selection of aptamers that act with Zn2+," *J. Inorg. Biochem.*, 82:197-206 (2000).

Kiga, D., Y. Futamura, K. Sakamoto, S. Yokoyama, "An RNA aptamer to the xanthine/guanine base with a distinctive mode of purine recognition," *Nucl. Acids Res.*, 26:1755-1760 (1998).

Klussmann, S., A. Nolte, R. Bald, V. Erdmann,. And J. Fuerste, "Mirror-image RNA that binds D-adenosine," *Nat. Biotechnol.* 14:1112-5 (1996).

Kohama, T., A. Olivera, L. Edsall, M. Nagiec, et al., "Molecular Cloning and Functional Characterization of Murine Sphingosine Kinase," *J. Biol. Chem.*, 273(37)23722-23728 (1998).

Koizumi, M. and R. Breaker, "Molecular Recognition of cAMP by an RNA Aptamer," *Biochemistry*, 39:8983-92 (2000).

Lato, S., A. Boles, and A. Ellington, "In vitro selection of RNA lectins: Using combinatorial chemistry to interpret ribozyme evolution," *Chem. Biol.* 2:291-303 (1995).

Lauhon, C. and J. Szostak, "RNA aptamers that bind flavin and nicotinamide redox cofactors," *J. Am. Chem. Soc.*, 117:1246-1257 (1995).

Li, J. and Y. Lu, "A highly sensitive and selective catalytic DNA biosensor for lead ions," *J. Am. Chem. Soc.*, 122:10466-10467 (2000).

Li, J., W. Zheng, A. Kwon, and Y. Lu, "In vitro selection and characterization of a highly efficient Zn(II)-dependent RNA-cleaving deoxyribozyme," *Nucl.Acids Res.*, 28:481-488 (2000).

Li, Y. and D. Sen, "A catalytic DNA for porphyrin metallation," *Nat. Struct. Biol.*, 3:743-7 (1996).

Li, Y. and R. Breaker, "Deoxyribozymes: new players in the ancient game of biocatalysis," *Curr. Opin. Struct. Biol.*, 9:315-323 (1999).

Li, Y. and R. Breaker, "Phosphorylating DNA with DNA," *Proc. Natl. Acad. Sci. USA*, 96:2746-2751 (1999).

Link, S., Z. Wang, M. El-Sayed, "Alloy formation of gold-silver particles and the dependence of the plasmon absorption on their compositions," *J. Phys. Chem. B* 103:3529-3533 (1999).

Lohse, P. and J. Szostak, "Ribozyme-catalysed amino-acid transfer reactions," *Nature*, 381:442-444 (1996) .

Lorsch, J. and J. Szostak, "In vitro evolution of new ribozymes with polynucleotide kinase activity," *Nature*, 371:31-36 (1994).

Lorsch, J. and J. Szostak, "In vitro selection of RNA aptamers specific for cyanocobalamin," *Biochemistry*, 33:973-82 (1994).

Lu, Y., "New Transition-Metal-Dependent DNAzymes as Efficient Endonucleqses and as Selective Metal Biosensors," *Chem. Eur. J.*, 8(20)4588-4596 (2002).

Majerfeld, I. and M. Yarus, "An RNA pocket for an aliphatic hydrophobe," *Nat. Struct. Biol.*, 1:287-92 (1994).

Majerfeld, I. and M. Yarus, "Isoleucine:RNA sites with associated coding sequences," *RNA*, 4:471-8 (1998).

Mannironi, C., A. Di Nardo, P. Fruscoloni, and G. Tocchini-Valentini, "In vitro selection of dopamine RNA ligands," *Biochemistry*, 36:9726-34 (1997).

Maoz, R. and J. Sagiv, "Penetration-controlled reactions in organized monolayer assemblies. 1. Aqueous permanganate interaction with monolayer and multilayer films of long-chain surfactants," *Langmuir* 3:1034-1044 (1987).

Mirkin, C., R. Letsinger, R. Mucic, J. Storhoff, "A DNA-based method for rationally assembling particles into macroscopic materials," *Nature* 382:607-609 (1996).

Mucic, R., M. Herrlein, C. Mirkin, R. Letsinger, "Synthesis and characterization of DNA with ferrocenyl groups attached to their 5'-termini: Electrochemical characterization of a redox-active nucleotide monolayer" *Chem. Commun.* 555 (1996). (Reference Incomplete.).

Nissen, P., Hansen, J., Ban, N., Moore, P.B. & Steitz, T.A. (2000). The structural basis of ribosome activity in peptide bond synthesis. *Science* (Washington, D. C.) 289:920-30.

Nolte, A., S. Klussmann, R. Bald, V. Erdmann, and J. Fuerste, "Mirror-design of L-oligonucleotide ligands binding to L-arginine," *Nature Biotech.*, 14:1116-1119 (1996).

Nuzzo, R., F. Fusco, D. Allara, "Spontaneously organized molecular assemblies, 3. Preparation and properties of solution adsorbed monolayers of organic disulfides on gold surfaces," *J. Am. Chem. Soc.* 109:2358-2368 (1987).

Okazawa, A., H. Maeda, E. Fukusaki, Y. Katakura, and A. Kobayashi, "In vitro selection of hematoporphyrin binding DNA aptamers," *Bioorg. Med. Chem. Lett.*, 10:2653-6 (2000).

Pan, T. and O. Uhlenbeck, "A small metalloribozyme with a two-step mechanism," *Nature*, 358:560-3 (1992).

Piccirilli, J., T. McConnell, A. Zaug, H. Noller, and T. Cech, "Aminoacyl esterase activity of the Tetrahymena ribozyme," *Science*, 256:1420-1424 (1992).

Prudent, J., T. Uno, and P. Schultz, "Expanding the scope of RNA catalysis" *Science*, 264:1924-1927 (1994).

Rakow, N. and K. Suslick, "A colorimetric sensor array for odour visualization," *Nature*, 406:710-713 (2000).

Rink, S., J. Shen, and L. Loeb, "Creation of RNA molecules that recognize the oxidative lesion 7,8-dihydro-8-hydroxy-2'-deoxyguanosine (8-oxodG) in DNA," *Proc. Natl. Acad. Sci. USA*, 95:11619-24 (1998).

Robertson, M. and A. Ellington, "In vitro selection of an allosteric ribozyme that transduces analytes to amplicons," *Nat. Biotechnol.* 17:62-66 (1999).

Roth, A. and R. Breaker, "An amino acid as a cofactor for a catalytic polynucleotide," *Proc. Natl. Acad. Sci. USA* 95:6027-6031 (1998).

Rusconi, C., E. Scardino, J. Layzer, G. Pitoc, et al., "RNA aptamers as reversible antagonists of coagulation factor IXa," *Nature*, 419:90-94 (2002).

Santoro, S. and G. Joyce, "A general purpose RNA-cleaving DNA enzyme," *Proc. Natl. Acad. Sci. USA*, 94:4262-4266 (1997).

Santoro, S. and G. Joyce, "Mechanism and utility of an RNA-cleaving DNA enzyme," *Biochemistry*, 37:13330-13342 (1998).

Sassanfar, M. and J. Szostak, "An RNA motif that binds ATP," *Nature* (London), 364:550-553, (1993).

Seetharaman, S., M. Zivarts, N. Sudarsan, and R. Breaker, "Immobilized RNA switches for the analysis of complex chemical and biological mixtures," *Nat. Biotechnol.* 19:336-341 (2001).

Sen, D. and C. Geyer, "DNA enzymes," *Curr. Opin. Chem. Biol.* 2:680-687 (1998).

Shaiu, W., D. Larson, J. Vesenka, and E. Henderson, "Atomic force microscopy of oriented linear DNA molecules labeled with 5nm gold spheres," *Nucl. Acids Res.*, 21:99-103 (1993).

Sigurdsson, S., J. Thomson, and F. Eckstein, "Small ribozymes," *Cold Spring Harbor Monogr. Ser.*, 35:339-76 (1998).

Smith, J., D. Olson, and B. Armitage, "Molecular recognition of PNA-containing hybrids: Spontaneous assembly of helical cyanine dye aggregates on PNA templates," *J. Am. Chem. Soc.* 121:2686-2695 (1999).

Soriaga, M. and A. Hubbard, "Determination of the orientation of aromatic molecules adsorbed on platinum electrodes: The influence of solute concentration," *J. Am. Chem. Soc.*, 104:3937-3941 (1982).

Soukup, G. and R. Breaker, "Allosteric nucleic acid catalysts," *Curr. Opin. Struct. Biol.*, 10:318-325 (2000).

Stage-Zimmermann, T. and O. Uhlenbeck, "Hammerhead ribozyme kinetics," *RNA*, 4:875-89 (1998).

Stojanovic, M. and D. Landry, "Aptamer-based colorimetric probe for cocaine," *J. Am. Chem. Soc.*, 124:9678-9679 (2002).

Storhoff, J., R. Elghanian, R. Mucic, C. Mirkin, and R. Letsinger, "One-pot colorimetric differentiation of polynucleotides with single base imperfections using gold particle probes," *J. Am. Chem. Soc.* 120:1959-1964 (1998).

Sun, L., M. Cairns, E. Saravolac, A. Baker, A. and W. Gerlach, "Catalytic nucleic acids: From lab to applications," *Pharmacol. Rev.* 52:325-47 (2000).

Tang, J. and R. Breaker, "Rational design of allosteric ribozymes," *Chem. Biol.*, 4:453-459 (1997).

Tang, J. and R. Breaker, "Structural diversity of self-cleaving ribozymes," *Proc. Natl. Acad. Sci. USA*, 97:5784-5789 (2000).

Tanner, N., "Biochemistry of hepatitis delta virus catalytic RNAs," *Ribozymes Gene Ther. Cancer*: 23-38 (1998).

Tao, J. and A. Frankel, "Arginine-Binding RNAs Resembling TAR Identified by in Vitro Selection," *Biochemistry*, 35:2229-38 (1996).

Tarasow, T., S. Tarasow, and B. Eaton, "RNA-catalysed carbon-carbon bond formation," *Nature*, 389:54-57 (1997).

Timmons and Zisman., "Investigation of Fatty Acid Monolayers on Metals by Contact Potential Measurements," *J. Phys. Chem.* 69:984-990 (1965).

Tompkins, H. and D. Allara, "The study of the gas-solid interaction of acetic acid with a cuprous oxide surface using reflection-absorption spectroscopy," *J. Coll. and Interface Science*, 49(3):410-420 (1974).

Travascio, P., A. Bennet, D. Wang, and D. Sen, "A ribozyme and a catalytic DNA with peroxidase activity: active sites versus cofactor-binding sites," *Chemistry & Biology* 6:779-87 (1999).

Tsang, J. and G. Joyce, "In vitro evolution of randomized ribozymes," *Meth. Enzy.*, 267:410-426 (1996).

Tuerk, C. and L. Gold, "Systematic evolution of ligands by exponential enrichment: RNA ligands to bacteriophage T4 DNA polymerase," *Science*, 249:505-510 (1990).

Vaish, N., P. Heaton, O. Fedorova, and F. Eckstein, "In vitro selection of a purine nucleotide-specific hammerheadlike ribozyme," *Proc. Natl. Acad. Sci. USA*, 95:2158-2162 (1998).

Valadkhan, S. and J. Manley, "Splicing-related catalysis by protein-free snRNAs," *Nature* (London, United Kingdom), 413:701-7 (2001).

Vianini, E., M. Palumbo, and B. Gatto, "In vitro selection of DNA aptamers that bind L-tyrosinamide," *Bioorganic & Med. Chem.* 9:2543-8 (2001).

Wallace, S. and R. Schroeder, "In vitro selection and characterization of streptomycin-binding RNAs: recognition discrimination between antibiotics," *RNA*, 4:112-123(1998).

Wallis, M., B. Streicher, H. Wank, U. von Ahsen, et al., "In vitro selection of a viomycin-binding RNA pseudoknot," *Chem. Biol.*, 4:357-366 (1997).

Wallis, M., U. Von Ahsen, R. Schroeder, and M. Famulok, "A novel RNA motif for neomycin recognition," *Chem. Biol.* 2:543-52 (1995).

Walter, N. and J. Burke, "The hairpin ribozyme: structure, assembly and catalysis," *Curr. Opin. Chem. Biol.*, 2:24-30 (1998).

Wang, D., B. Lai, and D. Sen, "A general strategy for effector-mediated control of RNA-cleaving ribozymes and DNA enzymes," *J. Mol. Biol.* 318:33-43 (2002).

Wang, F., J. van Brocklyn, L. Edsall, V. Nava, and S. Spiegel, "Sphingosine-1-phosphate Inhibits Motility of Human Breast Cancer Cells Independently of Cell Surface Receptors," *Cancer Res.*, 59:6185-6191 (1999).

Wang, Y., J. Killian, K. Hamasaki, and R. Rando, "RNA Molecules That Specifically and Stoichiometrically Bind Aminoglycoside Antibiotics with High Affinities," *Biochemistry*, 35:12338-46 (1996).

Wecker, M., D. Smith, and L. Gold, "In vitro selection of a novel catalytic RNA: characterization of a sulfur alkylation reaction and interaction with a small peptide," *RNA*, 2:982-994 (1996).

Werstuck, G. and M. Green, "Controlling gene expression in living cells through small molecule-RNA interactions," *Science* (Washington, D. C.) 282:296-8 (1998).

Whitesides, George M., Proceedings of the Robert A. Welch Foundation 39th Conference On Chemical Research Nanophase Chemistry, Houston, TX, (1995).

Wiegand, T., R. Janssen, and E. Eaton, "Selection of RNA amide synthases," *Chem. Biol.*, 4:675-683 (1997).

Williams, K., X. Liu, T. Schumacher, H. Lin, et al., "Bioactive and nuclease-resistant L-DNA ligand of vasopressin," *Proc. Natl. Acad. Sci. USA*, 94:11285-90 (1997).

Wilson, C. and J. Szostak, "Isolation of a fluorophore-specific DNA aptamer with weak redox activity," *Chem. Biol.* 5:609-17 (1998).

Wilson, C. and J. Szostak, "In vitro evolution of a self-alkylating ribozyme," *Nature*, 374:777-782 (1995).

Wilson, D. and J. Szostak, "In vitro selection of functional nucleic acids," *Ann. Rev. Biochem.*, 68:611-647 (1999).

Xia, P., L. Wang, J. Gamble, and M. Vadas, "Activation of Sphingosine Kinase by Tumor Necrosis Factor-α Inhibits Apoptosis in Human Endothelial Cells," *J. Biol. Chem.*, 274(48)34999-34505 (1999).

Yang, Q., I. Goldstein, H. Mei, and D. Engelke, "DNA ligands that bind tightly and selectively to cellobiose," *Proc. Natl. Acad. Sci. USA*, 95:5462-5467 (1998).

Zhang,B. and T. Cech, "Peptide bond formation by in vitro selected ribozymes," *Nature*, 390:96-100 (1997).

Zillmann, M., S. Limauro, and J. Goodchild, "In vitro optimization of truncated stem-loop II variants of the hammerhead ribozyme for cleavage in low concentrations of magnesium under non-turnover conditions," *RNA*, 3:734-747 (1997).

Zimmerman, J. and L. Maher, III, "In vivo selection of spectinomycin-binding RNAs," *Nucl. Acids Res.* 30:5425-35 (2002).

Hesselberth, J.R. et al., "Simultaneous detection of diverse analytes with an aptazyme ligase array", Analytical Biochemistry vol. 312, No. 2, pp. 106-112, (2003).

Broude, N. E., "Stem-loop oligonucleotides: a robust tool for molecular biology and biotechnology", Trends in Biotechnology, vol. 20, No. 6, pp. 249-256, (2002).

Rajendran, M., et al., "Selecting nucleic acids for biosensor applications", Combinatorial Chemistry and High Throughput Screening, vol. 5, No. 4, pp. 263-270, (2002).

Liu, J., et al., "A colorimetric lead biosensor using DNAzyme-directed assembly of gold nanoparticles", Journal of the America Chemical Society, vol. 125, No. 22, pp. 6642-6643, (2003).

Lu, Y., et al., "New fluorescent and colorimetric DNAzyme biosensors for metal ions", Journal of Inorganic Biochemistry, vol. 96, No. 1, p. 30, 11th International Conference on Biological Inorganic Chemistry; Cairns, Australia, (2003).

Liu, J., et al., "Adenosine-dependent assembly of aptazyme-functionalized gold nanoparticles and its application as a colorimetric biosensor", Analytical Chemistry vol. 76, No. 6, pp. 1627-1632, (2004).

Abstract of Joyce, G., "Design and catalytic activity of enzyumic DNA molecules"., (1998).

Aggarwal, S.K., et al., "Determination of lead in urine and whole blood by stable isotope dilution gas chromatography-mass spectrometry"., Clinical Chemistry, vol. 40, No. 8, pp. 1494-1502, (1994).

Alivisatos, A.P., et al., "Organization of "nanocrystal molecules" using DNA"., Nature, vol. 382, pp. 609-611, (1996).

Allara, D. et al., "Spontaneously organized molecular assemblies. 1.Formation, dynamics and physical properties of n-alkanoic acids adsorbed from solution on an oxidized aluminum surface"., Langmuir, vol. 1, No. 1, pp. 45-52, (1985).

Andreola, M-L., et al., "DNA aptamers selected against the HIV-1 RNase H display in vitro antiviral activity"., Biochemistry, vol. 40, No. 34, pp. 10087-10094, (2001).

Bain, C. D., et al., "Modeling organic surfaces with self-assembled monolayers"., Angew. Chem. Int. Ed. Engl., vol. 28, No. 4, pp. 506-512, (1989).

Bannon, D.I., et al., "Graphite furnace atomic absorption spectroscopic measurement of blood lead in matrix-matched standards"., Clinical Chemistry, vol. 40, No. 9, pp. 1730-1734, (1994).

Been, M.D., et al., "Self-cleaving ribozymes of hepatitis delta virus RNA"., Eur. J. Biochem., vol. 247, pp. 741-753, (1997).

Berens, C., et al., "A tetracycline-binding RNA aptamer"., Bioorganic & Medicinal Chemistry, vol. 9, pp. 2549-2556, (2001).

Biroccio, A., et al., "Selection of RNA aptamers that are specific and high-affinity ligands of the hepatitis C virus RNA-dependent RNA polymerase"., Journal of Virology, vol. 76, No. 8, pp. 3688-3696, (2002).

Blake, D.A., et al., "Antibody-based sensors for heavy metal ions"., Biosensors & Bioelectronics, vol. 16, pp. 799-809, (2001).

Blank, M., et al., "Systematic evolution of a DNA aptamer binding to rat brain tumor microvessels. Selective targeting of endothelial regulatory protein pigpen"., Journal of Biological Chemistry, vol. 276, No. 19, pp. 16464-16468, (2001).

Bock, L.C., et al., "Selection of single-stranded DNA molecules that bind and inhibit human thrombin"., Nature, vol. 355, pp. 564-566, (1992).

Bogden, J.D., et al., "Soil contamination from lead in paint chips"., Bulletin of Environmental Contamination & Toxicology, vol. 14, No. 3, pp. 289-294, (1975).

Boiziau, C., et al., "DNA aptamers selected against the HIV-1 trans-activation-responsive RNA element form RNA-DNA kissing complexes"., Journal of Biological Chemistry, vol. 274, No. 18, pp. 12730-12737, (1999).

Bowins, R.J., et al., "Electrothermal isotope dilution inductively coupled plasma mass spectrometry method for the determination of sub-ng ml$^{-1}$ levels of lead in human plasma"., Journal of Analytical Atomic Spectrometry, vol. 9, pp. 1233-1236, (1994).

Breaker, R.R., "Catalytic DNA: in training and seeking employment"., Nature Biotechnology, vol. 17, pp. 422-423, (1999).

Breaker, R.R., "DNA aptamers and DNA enzymes" Current Opinion in Chemical Biology, vol. 1, pp. 26-31, (1997).

Breaker, R.R., "DNA enzymes"., Nature Biotechnology, vol. 15, pp. 427-431, (1997).

Breaker, R.R., "Molecular Biology: Making Catalytic DNAs"., Science, vol. 290, issue 5499, pp. 2095-2096, (2000).

Breaker, R.R., et al., "A DNA enzyme that cleaves RNA"., Chemistry & Biology, vol. 1, No. 4, pp. 223-229, (1994).

Breaker, R.R., et al., "A DNA enzyme with $Mg^{2+}$-dependent RNA phosphoesterase activity"., Chemistry & Biology, vol. 2, No. 10, pp. 655-660, (1995).

Breaker, R.R., et al., "Engineered allosteric ribozymes as biosensor components"., Current Opinion in Biotechnology, vol. 13, pp. 31-39, (2002).

Brody, E.N., et al., "Aptamers as therapeutic and diagnostic agents"., Reviews in Molecular Biotechnology, vol. 74, pp. 5-13, (2000).

Broude, N. E., "Stem-loop oligonucleotides: a robust tool for molecular biology and biotechnology", Trends in Biotechnology, vol. 20, No. 6, pp. 249-256, (2002).

Brown, A.K., et al., "A lead-dependent DNAzyme with a two-step mechanism"., Biochemistry, vol. 42, No. 23, pp. 7152-7161, (2003).

Bruesehoff, P.J., et al., "Improving metal ion specificity during in Vitro selection of catalytic DNA"., Combinatorial Chemistry & High Throughput Screening, vol. 5, pp. 327-335, (2002).

Bruno, J.G., et al., "In vitro selection of DNA aptamers to anthrax spores with electrochemiluminescence detection"., Biosensors & Bioelectronics, vol. 14, pp. 457-464, (1999).

Bruno, J.G., et al., "Use of magnetic beads in selection and detection of biotoxin aptamers by electrochemiluminescence and enzymatic methods"., BioTechniques, vol. 32, No. 1, pp. 178-180, pp. 182-183, (2002).

Brust, M., et al., "Novel gold-dithiol nano-networks with non-metallic electronic properties"., Advanced Materials, vol. 7, No. 9, pp. 795-797, (1995).

Burdette, S.C., et al., "Fluorescent Sensors for $Zn^{2+}$ Based on a Fluorescein Platform: Synthesis, Properties and Intracellular Distribution"., J. Am. Chem. Soc., vol. 123, No. 32, pp. 7831-7841, (2001).

Burgstaller, P., et al., "Isolation of RNA aptamers for biological cofactors by in vitro selection"., Angew. Chem. Int. Ed. Engl, vol. 33, No. 10, pp. 1084-1087, (1994).

Burgstaller, P., et al., "Structural probing and damage selection of citrulline- and arginine-specific RNA aptamers identify base positions required for binding"., Nucleic Acids Research, vol. 23, No. 23, pp. 4769-4776, (1995).

Burke, D.H., et al., "A Novel Acidophilic RNA Motif That Recognizes Coenzyme A"., Biochemistry, vol. 37, No. 13, pp. 4653-4663, (1998).

Burke, D.H., et al., "RNA aptamers to the adenosine moiety of S-adenosyl methionine: structural inferences from variations on a theme and the reproducibility of SELEX"., Nucleic Acids Research, vol. 25, No. 10, pp. 2020-2024, (1997).

Burke, D.H., et al., "RNA aptamers to the peptidyl transferase inhibitor chloramphenicol"., Chemistry & Biology, vol. 4, No. 11, pp. 833-843, (1997).

Burmeister, J., et al., "Cofactor-assisted self-cleavage in DNA libraries with a 3'-5'-phosphoramidate bond"., Angew. Chem. Int. Ed. Engl., vol. 36, No. 12, pp. 1321-1324, (1997).

Burwell Jr., R.L., "Modified silica gels as adsorbents and catalysts"., Chemical Technology, 4, pp. 370-377, (1974).

Cadwell, R.C., et al., "Mutagenic PCR"., PCR Methods and Applications, vol. 3, pp. S136-S140, (1994).

Cadwell, R.C., et al., "Randomization of genes by PCR mutagenesis"., PCR Methods and Applications, vol. 2, pp, 28-33, (1992).

Cake, K.M., et al., "In vivo x-ray fluorescence of bone lead in the study of human lead metabolism: serum lead, whole blood lead, bone lead, and cumulative exposure"., Advances in X-Ray Analysis, vol. 38, pp. 601-606, (1995).

Camara Rica, C., et al., "Determination of trace concentrations of lead and nickel in human milk by electrothermal atomisation atomic absorption spectrophotometry and inductively coupled plasma emission spectroscopy"., The Science of the Total Environment, vol. 22, pp. 193-201, (1982).

Cao, Y.W., et al., "DNA-modified core-shell Ag/Au nanoparticles"., J. Am. Chem. Soc., vol. 123, No. 32, pp. 7961-7962, (2001).

Carmi, N., et al., "Cleaving DNA with DNA"., Proc. Natl. Acad. Sci. USA, vol. 95, pp. 2233-2237, (1998).

Carmi, N., et al., "In vitro selection of self-cleaving DNAs"., Chemistry & Biology, vol. 3, No. 12, pp. 1039-1046, (1996).

Cech, T.R., "Structure and mechanism of the large catalytic RNAs: group I and group II introns and ribonuclease P"., The RNA World, pp. 239-269, Cold Spring Harbor Laboratory Press, Cold Spring Harbor, New York, (1993).

Cech, T.R., et al., "Group I ribozymes: substrate recognition, catalytic strategies, and comparative mechanistic analysis"., Nucleic Acids and Molecular Biology, vol. 10, pp. 1-17, (1996).

Chaloin, L., et al., "Endogenous expression of a high-affinity pseudoknot RNA aptamer suppresses replication of HIV-1"., Nucleic Acids Research, vol. 30, No. 18, pp. 4001-4008, (2002).

Chapman, K.B., et al., "In vitro selection of catalytic RNAs"., Current Opinion in Structural Biology, vol. 4, pp. 618-622, (1994).

Chartrand, P., et al., "Effect of structural modifications on the activity of the leadzyme"., Biochemistry, vol. 36, No. 11, pp. 3145-3150, (1997).

Chen, J., et al., "Synthesis from DNA of a molecule with the connectivity of a cube"., Nature, vol. 350, pp. 631-633, (1991).

Chen, C-T., et al., "A highly selective fluorescent chemosensor for lead ions"., J. Am. Chem. Soc., vol. 124, pp. 6246-6247, (2002).

Chen, J-H., et al., "A specific quadrilateral synthesized from DNA branched junctions"., J. Am. Chem. Soc., vol. 111, No. 16, pp. 6402-6407, (1989).

Chen, L., et al., "Crystal structure of a four-stranded intercalated DNA: $d(C_4)$"., Biochemistry, vol. 33, No. 46, pp. 13540-13546, (1994).

Chinnapen, D.J.F., et al., "Hemin-stimulated docking of cytochrome c to a hemin-DNA aptamer complex"., Biochemistry, vol. 41, No. 16, pp. 5202-5212, (2002).

Ciesiolka, J., et al., "Selection of an RNA domain that binds $Zn^{2+}$"., RNA, vol. 1, pp. 538-550, (1995).

Ciesiolka, J., et al., "Small RNA-divalent domains"., RNA, vol. 2, pp. 785-793, (1996).

Conaty, J., et al., "Selected classes of minimised hammerhead ribozyme have very high cleavage rates at low $Mg^{2+}$. concentration"., Nucleic Acids Research, vol. 27, No. 11, pp. 2400-2407, (1999).

Conn, M.M., et al., "Porphyrin Metalation Catalyzed by a Small RNA Molecule"., J. Am. Chem. Soc. vol. 118, No. 29, pp. 7012-7013, (1996).

Connell, G.J., et al., "RNAs with dual specificity and dual RNAs with similar specificity"., Science, New Series, vol. 264, issue 5162, pp. 1137-1141, (1994).

Connell, G.J., et al., "Three small ribooligonucleotides with specific arginine sites"., Biochemistry, vol. 32, No. 21, pp. 5497-5502, (1993).

Cuenoud, B., et al., "A DNA metalloenzyme with DNA ligase activity"., Nature, vol. 375, pp. 611-614, (1995).

Czarnik, A.W., "Desperately seeking sensors"., Chemistry & Biology, vol. 2, No. 7, pp. 423-428, (1995).

Dai, X., et al., "Cleavage of an amide bond by a ribozyme"., Science, New Series, vol. 267, issue 5195, pp. 237-240, (1995).

Davis, J.H., et al., "Isolation of high-affinity GTP aptamers from partially structured RNA libraries"., Proc. Natl. Acad. Sci. USA, vol. 99, No. 18, pp. 11616-11621, (2002).

Davis, K.A., et al., "Staining of cell surface human CD4 with 2'-F-pyrimidine-containing RNA aptamers for flow cytometry"., Nucleic Acids Research, vol. 26, No. 17, pp. 3915-3924, (1998).

Definition of the word "ion" printed from Merriam-Webster online dictionary (www.m-w.com) on Jun. 30, 2004.

Definition of the word "particle" printed from Merriam-Webster online dictionary (www.m-w.com) on Jun. 29, 2004.

Deo, S., et al., "A Selective, Ratiometric Fluorescent Sensor for $Pb^{2+}$" J. Am. Chem. Soc., vol. 122, No. 1, pp. 174-175, (2000).

Derose, V.J., "Two Decades of RNA Catalysis"., Chemistry & Biology, vol. 9, pp. 961-969, (2002).

Didenko, V.V., "DNA probes using fluorescence resonance energy transfer (FRET): Designs and applications"., BioTechniques, vol. 31, pp. 1106-1121, (2001). We have reference, but we are missing pp. 1119-1121.

Doudna, J.A., et al., "The Chemical Repertoire of Natural Ribozymes"., Nature, vol. 418, pp. 222-228, (2002).

Dubois, L.H., et al., "Synthesis, structure, and properties of model organic surfaces"., Annu. Rev. Phys. Chem., vol. 43, pp. 437-463, (1992).

Earnshaw, D.J., et al., "Modified oligoribonucleotides as site-specific probes of RNA structure and function"., Biopolymers (Nucleic Acid Sciences), vol. 48, pp. 39-55, (1998).

Ekland, E.H., et al., "RNA-catalysed RNA polymerization using nucleoside triphosphates"., Nature, vol. 382, pp. 373-376, (1996).

Ekland, E.H., et al., "Structurally complex and highly active RNA ligases derived from random RNA sequences"., Science,, vol. 269, issue 5222, pp. 364-370, (1995).

Elghanian, R., et al., "Selective colorimetric detection of polynucleotides based on the distance-dependent optical properties of gold nanoparticles"., Science, vol. 277, pp. 1078-1081, (1997).

Ellington, A.D., et al., "Aptamers as potential nucleic acid pharmaceuticals"., Biotechnology Annual Review, vol. 1, pp. 185-214, (1995).

Ellington, A.D., et al., "In vitro selection of RNA molecules that bind specific ligands"., Nature, vol. 346, pp. 818-822, (1990).

Ellington, A.D., et al., "Selection in vitro of single-stranded DNA molecules that fold into specific ligand-binding structures"., Nature, vol. 355, pp. 850-852, (1992).

Famulok, M., "Molecular Recognition of Amino Acids by RNA-Aptamers: An L-Citrulline Binding RNA Motif and Its Evolution into an L-Arginine Binder"., J. Am. Chem. Soc., vol. 116, No. 5, pp. 1698-1706, (1994).

Famulok, M., "Oligonucleotide aptamers that recognize small molecules", Current Opinion in Structural Biology, vol. 9, pp. 324-329, (1999).

Famulok, M., et al., "In Vitro Selection Analysis of Neomycin Binding RNAs with a Mutagenized Pool of Variants of the 16S rRNA Decoding Region"., Biochemistry, vol. 35, No. 14, pp. 4265-4270, (1996).

Famulok, M., et al., "Stereospecific recognition of tryptophan agarose by in vitro selected RNA"., J. Am. Chem. Soc., vol. 114, No. 10, pp. 3990-3991, (1992).

Faulhammer, D., et al., "Characterization and Divalent Metal-ion Dependence of in Vitro Selected Deoxyribozymes which Cleave DNA/RNA Chimeric Oligonucleotides"., J. Mol. Biol., vol. 269, pp. 188-202, (1997).

Faulhammer, D., et al., "The $Ca^{2+}$ion as a cofactor for a novel RNA-cleaving deoxyribozyme"., Angew. Chem., Int. Ed. Engl., vol. 35, No. 23/24, pp. 2837-2841, (1996).

Feldman, B.J., et al., "Determination of lead in blood by square wave anodic stripping voltammetry at a carbon disk ultramicroelectrode"., Analytical Chemistry, vol. 66, No. 13, pp. 1983-1987, (1994).

Ferguson, A., et al., "A novel strategy for selection of allosteric ribozymes yields riboreporter™ sensors for caffeine and aspartame"., Nucleic Acids Research, vol. 32, No. 5, pp. 1756-1766, (2004).

Fodor, S.P.A., et al., "Light-directed, spatially addressable parallel chemical synthesis"., Science, New Series, vol. 251, issue 4995, pp. 767-773, (1991).

Frank, D.N., et al., "In vitro selection for altered divalent metal specificity in the RNase P RNA"., Proc. Natl. Acad. Sci. USA, vol. 94, pp. 14355-14360, (1997).

Frens, G., et al., "Controlled Nucleation for the regulation of the particle size in monodisperse gold suspensions"., Nature Physical Science, vol. 241, pp. 20-22, (1973).

Fukusaki, E-I., et al., "DNA aptamers that bind to chitin"., Bioorganic & Medicinal Chemistry letters, vol. 10, pp. 423-425, (2000).

Geiger, A., et al., "RNA aptamers that bind L-arginine with sub-micromolar dissociation constants and high enantioselectivity"., Nucleic Acids Research, vol. 24, No. 6, pp. 1029-1036, (1996).

Geyer, C.R., et al., "Evidence for the metal-cofactor independence of an RNA phosphodiester-cleaving DNA enzyme"., Chemistry & Biology, vol. 4, No. 8, pp. 579-593, (1997).

Geyer, C.R., et at., "Lanthanide Probes for a Phosphodiester-cleaving, Lead-dependent, DNAzyme", J. Mol. Biol., vol. 275, pp. 483-489, (1998).

Giver, L., et al., "Selection and design of high-affinity RNA ligands for HIV-1 Rev"., Gene, vol. 137, pp. 19-24, (1993).

Giver, L., et al., "Selective optimization of the Rev-binding element of HIV-1",Nucleic Acids Research, vol. 21, No. 23, pp. 5509-5516, (1993).

Godwin, H.A., et al., "A Flourescent Zinc Probe Based on Metal-Induced Peptide Folding"., J. Am. Chem. Soc., vol. 118, pp. 6514-6515, (1996).

Grabar, K., et al., "Preparation and characterization of Au colloid Monolayers"., Analytical chemistry, vol. 67, No. 4, pp. 735-743, (1995).

Granadillo, V.A., et al., "The influence of the blood levels of lead, aluminum and vanadium upon the arterial hypertension"., Clinica Chimica Acta, vol. 233, pp. 47-59, (1995).

Grate, D., et al., "Laser-mediated, site-specific inactivation of RNA transcripts"., Proc. Natl. Acad. Sci. USA, vol. 96, pp. 6131-6136, (1999).

Guschin, D., et al., "Manual manufacturing of oligonucleotide, DNA, and protein microchips"., Analytical Biochemistry, vol. 250, pp. 203-211, (1997).

Haller, A.A., et al., "In vitro selection of a 7-methyl-guanosine binding RNA that inhibits translation of capped mRNA molecules"., Proc. Natl. Acad. Sci. USA, vol. 94, pp. 8521-8526, (1997).

Harada, K., et al., "Identification of two novel arginine binding DNAs"., The EMBO Journal, vol. 14, No. 23, pp. 5798-5811, (1995).

Hartig, J.S., et al., "Reporter ribozymes for real-time analysis of domain-specific interactions in biomolecules: HIV-1 reverse transcriptase and the primer-template complex"., Angew. Chem. Int. Ed., vol. 41, No. 22, pp. 4263-4266, (2002).

He, X-x., et al., "Bioconjugated nanoparticles for DNA protection from cleavage"., J. Am. Chem. Soc., vol. 125, No. 24, pp. 7168-7169, (2003).

Hennrich, G., et al., "Redox switchable fluorescent probe selective for either Hg(II) or Cd(II) and Zn(II)" J. Am. Chem. Soc., vol. 121, No. 21, pp. 5073-5074, (1999).

Hesselberth, J., et al., "In vitro selection of nucleic acids for diagnostic applications"., Reviews in Molecular Biotechnology, vol. 74, pp. 15-25, (2000).

Hesselberth, J.R., et al., "Simultaneous detection of diverse analytes with an aptazyme ligase array", Analytical Biochemistry vol. 312, pp. 106-112, (2003).

Ho, H-A., et al., "Optical sensors based on hybrid aptamer/conjugated polymer complexes"., J. Am. Chem. Soc., vol. 126, No. 5, pp. 1384-1387, (2004).

Hock, B., "Antibodies for immunosensors, A review"., Analytica Chimica Acta, vol. 347, pp. 177-186, (1997).

Hofmann, H.P., et al., "$Ni^{2+}$-binding RNA motifs with an asymmetric purine-rich internal loop and a G-A base pair"., RNA, vol. 3, pp. 1289-1300, (1997).

Holeman, L.A., et al., "Isolation and characterization of fluorophore-binding RNA aptamers"., Folding & Design, vol. 3, pp. 423-431, (1998).

Hoogstraten, C.G., et al., "NMR solution structure of the lead-dependent ribozyme: Evidence for dynamics in RNA catalysis"., J. Mol. Biol., vol. 284, pp. 337-350, (1998).

Hoogstraten, C.G., et al., "Structural analysis of metal ion ligation to nucleotides and nucleic acids using pulsed EPR spectroscopy"., J. Am. Chem. Soc., vol. 124, No. 5, pp. 834-842, (2002).

Huizenga, D.E., et al., "A DNA aptamer that binds adenosine and ATP"., Biochemistry, vol. 34, No. 2, pp. 656-665, (1995).

Iler, R.K., "The Chemistry of Silica: Solubility, Polymerization, Colloid and Surface Properties, and Biochemistry. Chapter 6, The surface chemistry of silica"., pp. 622-729, A Wiley-Interscience Publication, New York, (1979).

Illangasekare, M., et al., "Small-molecule-substrate interactions with a self-aminoacylating ribozyme"., J. Mol. Biol., vol. 268, pp. 631-639, (1997).

Imperiali, B., et al., "Peptide platforms for metal ion sensing"., Proc. SPIE—The international society for optical engineering, vol. 3858, pp. 135-143, (1999).

International Search Report dated Jan. 15, 2003 for corresponding PCT application No. PCT/US01/20557.

International Search Report dated Aug. 1, 2003 for corresponding PCT application No. PCT/US03/08483.

Iqbal, S.S., et al., "A review of molecular recognition technologies for detection of biological threat agents"., Biosensors & Bioelectronics, vol. 15, pp. 549-578, (2000).

Jagner, D., et al., "Determination of lead in microliter amounts of whole blood by stripping potentiometry"., Electroanalysis, vol. 6, pp. 285-291, (1994).

Jayasena, S.D., "Aptamers: an emerging class of molecules that rival antibodies in diagnostics"., Clinical Chemistry, vol. 45, No. 9, pp. 1628-1650, (1999).

Jenison, R., et al., "Interference-based detection of nucleic acid targets on optically coated silicon", Nature Biotechnology, vol. 19, pp. 62-65, (2001).

Jenison, R.D., et al., "High-resolution molecular discrimination by RNA"., Science, vol. 263, pp. 1425-1429, (1994).

Jenne, A., et al., "Rapid Identification and Characterization of Hammerhead-Ribozyme Inhibitors Using Fluorescence-Based Technology"., Nature Biotechnology, vol. 19, pp. 56-61, (2001).

Jenne, A., et al., "Real-time Characterization of Ribozymes by Fluorescence Resonance Energy Transfer (FRET)"., Angewandte Chemie. International Edition, vol. 38, No. 9, pp. 1300-1303, (1999).

Jhaveri, S., et al., "In vitro selection of signaling aptamers"., Nature Biotechnology, vol. 18, pp. 1293-1297, (2000).

Jhaveri, S.D., et al., "Designed signaling aptamers that transduce molecular recognition to changes in fluorescence intensity"., J. Am. Chem. Soc., vol. 122, No. 11, pp. 2469-2473, (2000).

Jin, R., et al., "What controls the melting properties of DNA-linked gold nanoparticle assemblies?"., J. Am. Chem. Soc., vol. 125, No. 6, pp. 1643-1654, (2003).

Joos, B., et al., "Covalent attachment of hybridizable oligonucleotides to glass supports"., Analytical Biochemistry, vol. 247, pp. 96-101, (1997).

Josephson, L., et al., "Magnetic nanosensors for the detection of oligonucleotide sequences"., Angewandte Chemie. International Edition, vol. 40, No. 17, pp. 3204-3206, (2001).

Joyce, G.F., "Appendix 3: Reactions Catalyzed by RNA and DNA Enzymes". The RNA World, vol. 37, pp. 687-690, Cold Spring Harbor Laboratory Press, Cold Spring Harbor, New York, (1999).

Joyce, G.F., "In vitro evolution of nucleic acids"., Current Opinion in Structural Biology, vol. 4, pp. 331-336, (1994).

Katahira, M., et al., "Two metal-binding sites in a lead ribozyme bound to competitively by $Pb^{2+}$ and $Mg^{2+}$ Induced structural changes as revealed by NMR"., European Journal of Biochemistry, vol. 255, pp. 727-733, (1998).

Kato, T., et al., "In vitro selection of DNA aptamers which bind to cholic acid"., Biochimica et Biophysica Acta, vol. 1493, pp. 12-18, (2000).

Kawakami, J., et al., "In vitro selection of aptamers that act with $Zn^{2+}$"., Journal of Inorganic Biochemistry, vol. 82, pp. 197-206, (2000).

Khan, R., et al., "Interaction of retroviral nucleocapsid proteins with transfer $RNA^{Phe}$ : a lead ribozyme and $^1H$ NMR study"., Nucleic Acids Research, vol. 24, No. 18, pp. 3568-3575, (1996).

Khosraviani, M., et al., "Detection of heavy metals by immunoassay: Optimization and validation of a rapid, portable assay for ionic cadmium"., Environ. Sci. Technol., vol. 32, No. 1, pp. 137-142, (1998).

Kiga, D., et al., "An RNA aptamer to the xanthine/guanine base with a distinctive mode of purine recognition"., Nucleic Acids Research, vol. 26, No. 7, pp. 1755-1760, (1998).

Kim, M.H., et al., "Activation and repression of the activity of a lead ribozyme by the combination of $Pb^{2+}$ and $Mg^{2+1n}$"., J. Biochem., vol. 122, No. 5, pp. 1062-1067, (1997).

Kluβmann, S., et at "Mirror-image RNA that binds D-adenosine"., Nature Biotechnology, vol. 14, pp. 1112-1115. (1996).

Kohama, T., et al., "Molecular Cloning and Functional Characterization of Murine Sphingosine Kinase", The Journal of Biological Chemistry, vol. 273, No. 37, pp. 23722-23728, (1998).

Koizumi, M., et al., "Allosteric selection of ribozymes that respond to the second messengers cGMP and cAMP"., Nature Structural Biology, vol. 6, No. 11, pp. 1062-1071, (1999).

Koizumi, M., et al., "Molecular Recognition of cAMP by an RNA Aptamer"., Biochemistry, vol. 39, No. 30, pp. 8983-8992, (2000).

Koizumi, M., et al., "Allosteric ribozymes sensitive to the second messengers cAMP and cGMP"., Nucleic Acids Symposium Series, No. 42, pp. 275-276, (1999).

Kruger, K., et al., "Self-splicing RNA: autoexcision and autocyclization of the ribosomal RNA intervening sequence of the Tetrahymena"., Cell, vol. 31, pp. 147-157, (1982).

Lato, S.M., et al., "In vitro selection of RNA lectins: Using combinatorial chemistry to interpret ribozyme evolution"., Chemistry & Biology, vol. 2, No. 5, pp. 291-303, (1995).

Lauhon, C. T., et al., "RNA aptamers that bind flavin and nicotinamide redox cofactors"., J. Am. Chem. Soc., vol. 117, No. 4, pp. 1246-1257, (1995).

Lebruska, L.L., "Selection and Characterization of an RNA Decoy for Transcription Factor NF-κB"., Biochemistry, vol. 38, No. 10, pp. 3168-3174, (1999).

Lee, M., et al., "A fiber-optic microarray biosensor using aptamers as receptors"., Analytical Biochemistry, vol. 282, pp. 142-146, (2000).

Lee, S-W., et al., "Ordering of quantum dots using genetically engineered viruses"., Science, vol. 296, pp. 892-895, (2002).

Legault, P., et al., "Order, dynamics and metal-binding in the lead-dependent ribozyme"., J. Mol. Biol., vol. 284, pp. 325-335, (1998).

Lehman, N., et al., "Evolution in vitro of an RNA enzyme with altered metal dependence"., Nature, vol. 361, pp. 182-185, (1993).

Lemieux, S., et al., "Modeling active RNA structures using the intersection of conformational space: application to the lead-activated ribozyme"., RNA, vol. 4, pp. 739-749, (1998).

Levy, M., et al., "ATP-Dependent Allosteric DNA Enzymes"., Chemistry & Biology, vol. 9, pp. 417-426, (2002).

Li, J., et al., "A highly sensitive and selective catalytic DNA biosensor for lead ions"., J. Am. Chem. Soc., vol. 122, No. 42, pp. 10466-10467, (2000).

Li, J., et al., "In vitro selection and characterization of a highly efficient Zn(II)-dependent RNA-cleaving deoxyribozyme"., Nucleic Acids Research, vol. 28, No. 2, pp. 481-488, (2000).

Li, J.J., et al., "Using molecular beacons as a sensitive fluorescence assay for enzymatic cleavage of single-stranded DNA"., Nucleic Acids Research, vol. 28, No. 11, e52, pp. i-vi, (2000).

Li, Y., et al., "A catalytic DNA for porphyrin metallation"., Nature Structural Biology, vol. 3, No. 9, pp. 743-747, (1996).

Li, Y., et al., "Capping DNA with DNA"., Biochemistry, vol. 19, No. 11, pp. 3106-3114, (2000).

Li, Y., et al., "Deoxyribozymes: new players in the ancient game of biocatalysis"., Current Opinion in Structural Biology, vol. 9, pp. 315-323, (1999).

Li, Y., et al., "Phosphorylating DNA with DNA"., Proc. Natl. Acad. Sci. USA, vol. 96, pp. 2746-2751, (1999).

Link, S., et al., "Alloy formation of gold-silver nanoparticles and the dependence of the plasmon absorption on their composition"., J. Phys. Chem. B, vol. 103, No. 18, pp. 3529-3533, (1999).

Liu, H-W., et al., "Determination of cadmium, mercury and lead in seawater by electrothermal vaporization isotope dilution inductively coupled plasma mass spectrometry"., Spectrochimica Acta Part B Atomic Spectroscopy 54, pp. 1367-1375, (1999).

Liu, J., et al., "A colorimetric lead biosensor using DNAzyme-directed assembly of gold nanoparticles", J. Am. Chem. Soc., vol. 125, No. 22, pp. 6642-6643, (2003).

Liu, J., et al., "Accelerated color change of gold nanoparticles assembled by DNAzymes for simple and fast colorimetric $Pb^{2+}$ detection"., J. Am. Chem. Soc., vol. 126, No. 39, pp. 12298-12305, (2004).

Liu, J., et al., "Adenosine-dependent assembly of aptazyme-functionalized gold nanoparticles and its application as a colorimetric biosensor"., Analytical Chemistry, vol. 76, No. 6, pp. 1627-1632, (2004).

Liu, J., et al., "Colorimetric biosensors based on DNAzyme-assembled gold nanoparticles"., Journal of Fluorescence, vol. 14, No. 4, pp. 343-354, (2004).

Liu, J., et al., "Highly dispersible molecular sieve carbon nanoparticles"., Chem. Mater., vol. 16, No. 22, pp. 4205-4207, (2004).

Liu, X., et al., "A fiber-optic evanescent wave DNA biosensor based on novel molecular beacons"., Analytical Chemistry, vol. 71, No. 22, pp. 5054-5059, (1999).

Liu, Z., et al., "Assemblage of signaling DNA enzymes with intriguing metal-ion specificities and pH dependences"., J. Am. Chem. Soc., vol. 125, No. 25, pp. 7539-7545, (2003).

Lohse, P.A., et al., "Ribozyme-catalysed amino-acid transfer reactions"., Nature, vol. 381, pp. 442-444, (1996).

Lorsch, J.R., et al., "In vitro evolution of new ribozymes with polynucleotide kinase activity"., Nature, vol. 371, pp. 31-36, (1994).

Lorsch, J.R., et al., "In vitro selection of RNA aptamers specific for cyanocobalamin"., Biochemistry, vol. 33, No. 4, pp. 973-982, (1994).

Lott, W.B., et al., "A two-metal ion mechanism operates in the hammerhead ribozyme-mediated cleavage of an RNA substrate"., Proc. Natl. Acad. Sci. USA, vol. 95, pp. 542-547, (1998).

Lu, Y., "New transition-metal-dependent DNAzymes as efficient endonucleases and as selective metal biosensors"., Chem. Eur. J., vol. 8, No. 20, pp. 4589-4596, (2002).

Lu, Y., et al., "New fluorescent and colorimetric DNAzyme biosensors for metal ions", Journal of Inorganic Biochemistry, vol. 96, issue 1, pp. 30, Abstract of the $11^{th}$ International Conference on Biological Inorganic Chemistry; (Jul. 15, 2003).

Majerfeld, I., et al., "An RNA pocket for an aliphatic hydrophobe"., Structural Biology, vol. 1, No. 5, pp. 287-292, (1994).

Majerfeld, I., et al., "Isoleucine:RNA sites with associated coding sequences"., RNA, vol. 4, pp. 471-478, (1998).

Mannironi, C., et al., "In vitro selection of dopamine RNA ligands"., Biochemistry, vol. 36, No. 32, pp. 9726-9734, (1997).

Maoz, R., et al., "Penetration-controlled reactions in organized monolayer assemblies. 1. Aqueous permanganate interaction with monolayer and multilayer films of long-chain surfactants"., Langmuir. vol. 3, No. 6, pp. 1034-1044, (1987).

Marcus, A.H., et al., "Estimating the contribution of lead based paint to soil lead, dust lead, and childhood blood lead"., American Society for Testing and Materials Spec. STP 1226, pp. 12-23, (1995).

Marsh, T.C., et al., "A new DNA nanostructure, the G-wire, imaged by scanning probe microscopy"., Nucleic Acids Research, vol. 23, No. 4, pp. 696-700, (1995).

Matteucci, M.D., et al., "Synthesis of Deoxyoligonucleotides on a polymer support"., J. Am. Chem. Soc., vol. 103, No. 11, pp. 3185-3191, (1981).

Mecklenburg, M., et al., "A strategy for the broad range detection of compounds with affinity for nucleic acids"., Analytica Chimica Acta, vol. 347, pp. 79-86, (1997).

Mei, S.H.J., et al., "An efficient RNA-cleaving DNA enzyme that synchronizes catalysis with fluorescence signaling"., J. Am. Chem. Soc., vol. 125, No. 2, pp. 412-420, (2003).

Meli, M., et al., "Adenine-aptamer complexes: A bipartite RNA site that binds the adenine nucleic base"., The Journal of Biological Chemistry, vol. 277, No. 3, pp. 2104-2111, (2002).

Mirkin, C.A., et al., "A DNA-based method for rationally assembling nanoparticles into macroscopic materials"., Nature, vol. 382, pp. 607-609, (1996).

Mirkin, S.M., et al., "H-DNA and related structures"., Annu. Rev. Biophys. Biomol. Struct., vol. 23, pp. 541-576, (1994).

Miyawaki, A., et al. "Fluorescent indicators for $Ca^{2+}$ on green fluorescent proteins and calmodulin"., Nature, vol. 388, pp. 882-887, (1997).

Mucic, R.C., et al., "Synthesis and characterization of DNA with ferrocenyl groups attached to their 5'-termini: electrochemical characterization of a redox-active nucleotide monolayer"., Chem. Commun., pp. 555-557, (1996).

Mullah, B., et al., "Automated synthesis of double dye-labeled oligonucleotides using tetramethylrhodamine (TAMRA) solid supports"., Tetrahedron Letters, vol. 38, No. 33, pp. 5751-5754, (1997).

Nazarenko, I.A., et al., "A closed tube format for amplification and detection of DNA based on energy transfer"., Nucleic Acids Research, vol. 26, No. 12, pp. 2516-2521, (1997).

Nazarenko, I.A., et al., "Defining a Smaller RNA Substrate for Elongation Factor Tu"., Biochemistry, vol. 34, No. 8, pp. 2545-2552, (1995).

Niemeyer, C.M., "Nanoparticles, proteins, and nucleic acids: Biotechnology meets materials science"., Angew. Chem. Int. Edition, vol. 40, pp. 4128-4158, (2001).

Nieuwlandt, D., et al., "In Vitro Selection of RNA Ligands to Substance P"., Biochemistry, vol. 34, No. 16, pp. 5651-5659, (1995).

Nissen, P., et al., "The structural basis of ribosome activity in peptide bond synthesis"., Science, vol. 289, pp. 920-930, (2000).

Nolte, A., et al., "Mirror-design of L-oligonucleotide ligands binding to L-arginine"., Nature Biotechnology, vol. 14, pp. 1116-1119, (1996).

Nutiu, R., et al., "Structure-switching signaling aptamers"., J. Am. Chem. Soc., vol. 125, No. 16, pp. 4771-4778, (2003).

Nuzzo, R.G., et al., "Spontaneously organized molecular assemblies. 3. Preparation and properties of solution adsorbed monolayers of organic disulfides on gold surfaces"., J. Am. Chem. Soc., vol. 109, No. 8, pp. 2358-2368, (1987).

O'Donnell, M.J., et al., "High-Density, Covalent Attachment of DNA to Silicon Wafers for Analysis by MALDI-TOF Mass Spectrometry"., Analytical Chemistry, vol. 69, No. 13, pp. 2438-2443, (1997).

Oehme, I., et al., "Optical sensors for determination of heavy metal ions"., Mikrochim. Acta, vol. 126, pp. 177-192, (1997).

Ohmichi, T., et al., "Role of $Nd^{3+}$ and $Pb^{2+}$ on the RNA cleavage reaction by a small ribozyme"., Biochemistry, vol. 36, No. 12, pp. 3514-3521, (1997).

Ohmichi, T., et al., "Effect of substrate RNA sequence on the cleavage reaction by a short ribozyme"., Nucleic Acids Research, vol. 26, No. 24, pp. 5655-5661, (1998).

Okazawa, A., et al., "In vitro selection of hematoporphyrin binding DNA aptamers"., Bioorganic & Medicinal Chemistry, Letters 10, pp. 2653-2656, (2000).

Ota, N., et al., "Effects of helical structures formed by the binding arms of DNAzymes and their substrates on catalytic activity"., Nucleic Acids Research, vol. 26, No. 14, pp. 3385-3391, (1998).

Pan, T., et al., "A small metalloribozyme with a two-step mechanism"., Nature, vol. 358, pp. 560-563, (1992).

Pan, T., et al., "In vitro selection of RNAs that undergo autolytic cleavage with $Pb^{2+}$", Biochemistry, vol. 31, No. 16, pp. 3887-3895, (1992).

Pan, T., et al., "Properties of an in vitro selected $Pb^{2+}$ cleavage motif"., Biochemistry, vol. 33, No. 32, pp. 9561-9565, (1994).

Pan, W., et al., "Isolation of virus-neutralizing RNAs from a large pool of random sequences"., Proc. Natl. Acad. Sci. USA, vol. 92, pp. 11509-11513, (1995).

Park, S-J., et al., "Array-based electrical detection of DNA with nanoparticle probes"., Science, vol. 295, pp. 1503-1506, (2002).

Parsons, P.J., et al., "A rapid Zeeman graphite furnace atomic absorption spectrometric method for the determination of lead in blood"., Spectrochimica Acta, vol. 48B, No. 6/7, pp. 925-939, (1993).

Pavlov, A.R., et al., "Determination of lead in environmental water samples by a rapid and portable immunoassay"., ANYL, Book of Abstracts, 219th ACS National Meeting, San Francisco, CA, Mar. 26-30, 2000.

Pavlov, V., et al., "Aptamer-functionalized Au nanoparticles for the amplified optical detection of thrombin"., J. Am. Chem. Soc., vol. 126, No. 38, pp. 11768-11769, (2004).

Pearce, D.A., et al., "Peptidyl chemosensors incorporating a FRET mechanism for detection of Ni(II)"., Bioorganic & Medicinal Chemistry, Letters 8, pp. 1963-1968, (1998).

Pease, A.C., et al., "Light-generated oligonucleotide arrays for rapid DNA sequence analysis"., Proc. Natl. Acad. Sci. USA, vol. 91, pp. 5022-5026, (1994).

Piccirilli, J.A., et al., "Aminoacyl esterase activity of the tetrahymena ribozyme"., Science, New Series, vol. 256, issue 5062, pp. 1420-1424, (1992).

Pley, H.W., et al., "Three-dimensional structure of a hammerhead ribozyme"., Nature, vol. 372, pp. 68-74, (1994).

Potyrailo, R.A., et al., "Adapting selected nucleic acid ligands (aptamers) to biosensors"., Analytical Chemistry, vol. 70, No. 16, pp. 3419-3425, (1998).

Prudent, J.R., et al., "Expanding the scope of RNA catalysis"., Science, New Series, vol. 264, issue 5167, pp. 1924-1927, (1994).

Qiao, H., et al., "Transferability of blood lead determinations by furnace atomic absorption spectrophotometry and continuum background correction"., Clinical Chemistry, vol. 41, No. 10, pp. 1451-1454, (1995).

Rabinowitz, M., et al., "Home refinishing, lead paint, and infant blood lead levels"., American Journal of Public Health, vol. 75, No. 4, pp. 403-404, (1985).

Rajendran, M., et al., "Selecting nucleic acids for biosensor applications"., Combinatorial Chemistry and High Throughput Screening, vol. 5, No. 4, pp. 263-270, (2002).

Rakow, N. A., et al., "A colorimetric sensor array for odour visualization"., Nature, vol. 406, pp. 710-713, (2000).

Rink, S.M., et al., "Creation of RNA molecules that recognize the oxidative lesion 7,8-dihydro-8-hydroxy-2'-deoxyguanosine (8-oxodG) in DNA"., Proc. Natl. Acad. Sci. USA, vol. 95, pp. 11619-11624, (1998).

Robertson, M.P., et al., "Design and optimization of effector-activated ribozyme ligases"., Nucleic Acids Research, vol. 28, No. 8, pp. 1751-1759, (2000).

Robertson, M.P., et al., "In vitro selection of an allosteric ribozyme that transduces analytes to amplicons"., Nature Biotechnology, vol. 17, pp. 62-66, (1999).

Roth, A., et al., "An amino acid as a cofactor for a catalytic polynucleotide"., Proc. Natl. Acad. Sci. USA, vol. 95, pp. 6027-6031, (1998).

Roychowdhury-Saha, M., et al., "Flavin Recognition by an RNA Aptamer Targeted toward FAD"., Biochemistry, vol. 41, No. 8, pp. 2492-2499, (2002).

Ruckman, J., et al., "2'-Fluoropyrimidine RNA-based aptamers to the 165-amino acid form of vascular endothelial growth factor ($VEGF_{165}$) Inhibition of receptor binding and VEGF-induced vascular permeability through interactions requiring the exon 7-encoded domain"., The Journal of Biological Chemistry, vol. 273, No. 32, pp. 20556-20567, (1998).

Rurack, K., et al., "A selective and sensitive fluoroionophore for $Hg^{II}$, $Ag^{I}$, and $Cu^{II}$ with virtually decoupled fluorophore and receptor units"., J. Am. Chem. Soc., vol. 122, No. 5, pp. 968-969, (2000).

Rusconi, C.P., et al., "RNA aptamers as reversible antagonists of coagulation factor Ixa"., Nature, vol. 419, pp. 90-94, (2002).

Sabanayagam, C.R., et al., "Oligonucleotide immobilization on micropatterened streptavidin surfaces"., Nucleic Acids Research, vol. 28, No. 8, e33, pp. i-iv, (2000).

Santoro, S.W. et al., "Mechanism and utility of an RNA-cleaving DNA enzyme"., Biochemistry, vol. 37, No. 38, pp. 13330-13342, (1998).

Santoro, S.W., et al., "A general purpose RNA-cleaving DNA enzyme"., Proc. Natl. Acad. Sci. USA, vol. 94, pp. 4262-4266, (1997).

Santoro, S.W., et al., "RNA Cleavage by a DNA Enzyme with Extended Chemical Functionality"., J. Am. Chem. Soc., vol. 122, No. 11, pp. 2433-2439, (2000).

Sassanfar, M., et al., "An RNA motif that binds ATP"., Nature, vol. 364, pp. 550-553, (1993).

Schwartz, J., et al., "The risk of lead toxicity in homes with lead paint hazard"., Environmental Research, vol. 54, No. 1, pp. 1-7, (1991).

Scott, W.G., et al., "The crystal structure of an all-RNA hammerhead ribozyme: A proposed mechanism for RNA catalytic cleavage"., Cell, vol. 81, pp. 991-1002, (1995).

Scott, W.G., "RNA catalysis"., Current Opinion in Structural Biology, vol. 8, pp. 720-726, (1998).

Search results of key word search of medline, Mar. 26, 2000.

Search results of key word search on Chemical Abstracts, Mar. 24, 2000.

Search results of key word search from various databases, Mar. 24, 2000.

Seeman, N. C., et al., "Synthetic DNA knots and catenanes"., New Journal of Chemistry, vol. 17, pp. 739-755, (1993).

Seeman, N. C., et al., "Emulating biology: Building nanostructures from the bottom up"., Proc. Natl. Acad. Sci., vol. 99, suppl. 2, pp. 6451-6455, (2002).

Seeman, N.C., "DNA in a material world"., Nature, vol. 421, pp. 427-431, (2003).

Seetharaman, S., et al., "Immobilized RNA switches for the analysis of complex chemical and biological mixtures"., Nature Biotechnology, vol. 19, pp. 336-341, (2001).

Sen, D., et al., "DNA enzymes"., Current Opinion in Chemical Biology, vol. 2, pp. 680-687, (1998).

Shaiu, W-L., et al., "Atomic force microscopy of oriented linear DNA molecules labeled with 5nm gold spheres"., Nucleic Acids Research, vol. 21, No. 1, pp. 99-103, (1993).

Shaw, S.Y., et al., "Knotting of a DNA chain during ring closure"., Science, New Series, vol. 260, issue 5107, pp. 533-536, (1993).

Shekhtman, E.M., et al., "Stereostructure of replicative DNA catenanes from eukaryotic cells"., New Journal of Chemistry, vol. 17, pp. 757-763, (1993).

Sigurdsson, S.T., et al., "Small ribozymes"., RNA Structure and Function, Cold Spring Harbor Laboratory Press (Monograph 35), pp. 339-375, (1998).

Singh, K.K., et al., "Fluorescence Polarization for Monitoring Ribozyme Reactions in Real-Time"., Biotechniques, vol. 29, No. 2, pp. 344-351, (2000).

Smith, F.W., et al., "Quadruplex structure of oxytricha telomeric DNA oligonucleotides"., Nature, vol. 356, pp. 164-168, (1992).

Smith, J.O., et al., "Molecular recognition of PNA-containing hybrids: Spontaneous assembly of helical cyanine dye aggregates on PNA templates"., J. Am. Chem. Soc., vol. 121, No. 12, pp. 2686-2695, (1999).

Soriaga, M.P., et al., "Determination of the orientation of aromatic molecules adsorbed on platinum electrodes: The effect of solute concentration"., J. Am. Chem. Soc., vol. 104, No. 14, pp. 3937-3945, (1982).

Soukup, G.A., et al., "Engineering precision RNA molecular switches"., Proc. Natl. Acad. Sci. USA, vol. 96, pp. 3584-3589, (1999).

Soukup, G.A., et al., "Allosteric nucleic acid catalysts"., Current Opinion in Structural Biology, vol. 10, pp. 318-325, (2000).

Srisawat, C., et al., "Sephadex-binding RNA ligands: rapid affinity purification of RNA from complex RNA mixtures"., Nucleic Acids Research, vol. 29, No. 2 e4, pp. 1-5, (2001).

Stage-Zimmermann, T.K., et al., "Hammerhead ribozyme kinetics"., RNA, vol. 4, pp. 875-889, (1998).

Stojanovic, M.N., et al., "Aptamer-based colorimetric probe for cocaine"., J. Am. Chem. Soc., vol. 124, No. 33, pp. 9678-9679, (2002).

Stojanovic, M.N., et al., "Aptamer-based folding fluorescent sensor for cocaine"., Journal of the American Chemical Society, vol. 123, No. 21, pp. 4928-4931, (2001).

Stojanovic, M.N., et al., "Fluorescent sensors based on aptamer self-assembly"., Journal of the American Chemical Society, vol. 122, No. 46, pp. 11547-11548, (2000).

Storhoff, J.J., et al., "Programmed materials synthesis with DNA"., Chem. Rev., vol. 99, No. 7, pp. 1849-1862, (1999).

Storhoff, J.J., et al., "What Controls the Optical Properties of DNA-Linked Gold Nanoparticle Assemblies?"., J. Am. Chem. Soc., vol. 122, No. 19, pp. 4640-4650, (2000).

Storhoff, J.J., et al., "One-pot colorimetric differentiation of polynucleotides with single base imperfections using gold nanoparticle probes"., Journal of the American Chemical Society, vol. 120, No. 9, pp. 1959-1964, (1998).

Streicher, B., et al., "Lead cleavage site in the core structure of group I intron-RNA"., Nucleic Acids Research, vol. 21, No. 2, pp. 311-317, (1993).

Sugimoto, N., et al., "Site-specific cleavage reaction catalyzed by leadzyme is enhanced by combined effect of lead and rare earth ions"., FEBS Letters, vol. 393, pp. 97-100, (1996).

Sun, L.Q., et al., "Catalytic nucleic acids: From lab to applications"., Pharmacological Reviews, vol. 52, pp. 325-347, (2000).

Tahan, J.E., et al., "Electrothermal atomic absorption spectrometric determination of Al, Cu, Ge, Pb, V and Zn in clinical samples and in certified environmental reference materials"., Analytica Chimica Acta, vol. 295, pp, 187-197, (1994).

Takagi, Y., et al., "Survey and Summary: Recent advances in the elucidation of the mechanisms of action of ribozymes"., Nucleic Acids Research, vol. 29, No. 9, pp. 1815-1834, (2001).

Tang, J., et al., "Rational design of allosteric ribozymes"., Chemistry & Biology, vol. 4, No. 6, pp. 453-459, (1997).

Tang, J., et al., "Structural diversity of self-cleaving ribozymes"., Proc. Natl. Acad. Sci. USA, vol. 97, No. 11, pp. 5784-5789, (2000).

Tanner, N. K., "Biochemistry of hepatitis delta virus catalytic RNAs"., Ribozymes in the Gene Therapy of Cancer, Chapter 3, pp. 23-38, (1998).

Tao, J., et al., "Arginine-Binding RNAs Resembling TAR Identified by in Vitro Selection"., Biochemistry, vol. 35, No. 7, pp. 2229-2238, (1996).

Tarasow, T.M., et al., "RNA-catalysed carbon-carbon bond formation"., Nature, vol. 389, pp. 54-57, (1997).

Telting-Diaz, M., et al., "Mass-produced ionophore-based fluorescent microspheres for trace level determination of lead ions"., Analytical Chemistry, vol. 74, No. 20, pp. 5251-5256, (2002).

Thompson, R.B., et al., "Determination of Picomolar Concentrations of Metal Ions Using Fluorescence Anisotropy: Biosensing with a "Reagentless" Enzyme Transducer"., Analytical Chemistry, vol. 70, No. 22, pp. 4717-4723, (1998).

Timmons, C.O., et al., "Investigation of Fatty Acid Monolayers on Metals by Contact Potential Measurements", Journal of Physical Chemistry, vol. 69, No. 3, pp. 984-990, (1965).

Tompkins, H.G., et al., "The study of the gas-solid interaction of acetic acid with a cuprous oxide surface using reflection-absorption spectroscopy"., Journal of Colloid and Interface Science, vol. 49, No. 3, pp, 410-421, (1974).

Travascio, P., et al., "A ribozyme and a catalytic DNA with peroxidase activity: active sites versus cofactor-binding sites"., Chemistry & Biology, vol. 6, No. 11, pp. 779-787, (1999).

Tsang, J., et al., "In vitro evolution of randomized ribozymes"., Methods in Enzymology, vol. 267, pp. 410-426, (1996).

Tsien, R.Y., "Fluorescent and photochemical probes of dynamic biochemical signals inside living cells"., Fluorescent Chemosensors for Ion and Molecule Recognition, (ed. Czarnik, A. W.), chapter 9, pp. 130-146, American Chemical Society, (1993).

Tuerk, C., et al., "RNA pseudoknots that inhibit human immunodeficiency virus type 1 reverse transcriptase"., Proc. Natl. Acad. Sci. USA, vol. 89, pp. 6988-6992, (1992).

Tuerk, C., et al., "Systematic evolution of ligands by exponential enrichment: RNA ligands to bacteriophage T4 DNA polymerase"., Science, New Series, vol. 249, issue 4968, pp. 505-510, (1990).

Tyagi, S., et al., "Molecular Beacons: Probes that fluoresce upon hybridization"., Nature Biotechnology, vol. 14, pp. 303-308, (1996).

Tyagi, S., et al., "Multicolor molecular beacons for allele discrimination"., Nature Biotechnology, vol. 16, pp. 49-53, (1998).

Tyagi, S., et al., "Wavelength-shifting molecular beacons"., Nature Biotechnology, vol. 18, pp. 1191-1196, (2000).

Ueyama, H., "A novel potassium sensing in aqueous media with a synthetic oligonucleotide derivative. Fluorescence resonance energy transfer associated with guanine quartet-potassium ion complex formation"., J. Am. Chem. Soc., vol. 124, No. 48, pp. 14286-14287, (2002).

Uphoff, K.W., et al., "In vitro selection of aptamers: the dearth of pure reason"., Current Opinion in Structural Biology, vol. 6, pp. 281-288, (1996).

Vaish, N. K., et al., "In vitro selection of a purine nucleotide-specific hammerhead-like ribozyme"., Proc. Natl. Acad. Sci. USA, vol. 95, pp. 2158-2162, (1998).

Valadkhan, S., et al., "Splicing-related catalysis by protein-free snRNAs"., Nature, vol. 413, pp. 701-707, (2001).

Vianini, E., et al., "In vitro selection of DNA aptamers that bind L-tyrosinamide"., Bioorganic & Medicinal Chemistry, vol. 9, pp. 2543-2548, (2001).

Walkup, G.K., et al., "Design and Evaluation of a Peptidyl Fluorescent Chemosensor for Divalent Zinc"., J. Am. Chem. Soc., vol. 118, No. 12, pp. 3053-3054, (1996).

Wallace, S.T., et al., In vitro selection and characterization of streptomycin-binding RNAs: recognition discrimination between antibiotics. RNA, vol. 4, pp. 112-123, (1998).

Wallis, M.G., et al., "A novel RNA motif for neomycin recognition"., Chemistry & Biology, vol. 2, No. 8, pp. 543-552, (1995).

Wallis, M.G., et al., "In vitro selection of a viomycin-binding RNA pseudoknot"., Chemistry & Biology, vol. 4, No. 5, pp. 357-366, (1997).

Walter, F., et al., "Folding of the four-way RNA junction of the hairpin ribozyme"., Biochemistry, vol. 37, No. 50, pp. 17629-17636, (1998).

Walter, N. G., et al., "The hairpin ribozyme: structure, assembly and catalysis"., Current Opinion in Chemical Biology, vol. 2, pp. 24-30, (1998).

Wang, D.Y., et al., "A general strategy for effector-mediated control of RNA-cleaving ribozymes and DNA enzymes"., J. Mol. Biol., vol. 318, pp. 33-43, (2002).

Wang, F., et al., "Sphingosine-1-phosphate Inhibits Motility of Human Breast Cancer Cells Independently of Cell Surface Receptors"., Cancer Research, vol. 59, pp. 6185-6191, (1999).
Wang, J., "Survey and Summary: From DNA biosensors to gene chips"., Nucleic Acids Research, vol. 28, No. 16, pp. 3011-3016, (2000).
Wang, K.Y., et al., "A DNA aptamer which binds to and inhibits thrombin exhibits a new structural motif for DNA"., Biochemistry, vol. 32, No. 8, pp. 1899-1904, (1993).
Wang, Y., et al., "Assembly and characterization of five-arm and six-arm DNA branched junctions"., Biochemistry, vol. 30, pp. 5667-5674, (1991).
Wang, Y., et al., "RNA molecules that specifically and stoichiometrically bind aminoglycoside antibiotics with high affinities"., Biochemistry, vol. 35, No. 38, pp. 12338-12346, (1996).
Wecker, M., et al., "In vitro selection of a novel catalytic RNA: characterization of a sulfur alkylation reaction and interaction with a small peptide"., RNA, vol. 2, pp. 982-994, (1996).
Wedekind, J.E., et al., "Crystal structure of a lead-dependent ribozyme revealing metal binding sites relevant to catalysis"., Nature Structural Biology, vol. 6, No. 3, pp. 261-268, (1999).
Wedekind, J.E., et al., "Crystal structure of the leadzyme at 1.8, Å Resolution: Metal ion binding and the implications for catalytic mechanism and allo site ion regulation"., Biochemistry, vol. 42, No. 32, pp. 9554-9563, (2003).
Wells, R.D., "Unusual DNA structures"., Journal of Biological Chemistry, vol. 263, No. 3, pp. 1095-1098, (1988).
Werstuck, G., et al., "Controlling gene expression in living cells through small molecule-RNA interactions"., Science, vol. 282, pp. 296-298, (1998).
Whaley, S.R., et al., "Selection of peptides with semiconductor binding specificity for directed nanocrystal assembly"., Nature, vol. 405, pp. 665-668, (2000).
Whitesides, G.M., et al., "Self-assembled monolayers and lithography"., Proceedings of the Robert A. Welch Foundation 39th Conference On Chemical Research on Nanophase Chemistry, pp. 109-121, Houston, TX, Oct. 23-24, 1995.
Wiegand, T.W., et al., "High-affinity oligonucleotide ligands to human IgE inhibit binding to Fc epsilon receptor I"., The Journal of Immunology, vol. 157, pp. 221-230, (1996).
Wiegand, T.W., et al., "Selection of RNA amide synthases"., Chemistry & Biology, vol. 4, No. 9, pp. 675-683, (1997).
Williams, K.P., et al., "Bioactive and nuclease-resistant L-DNA ligand of vasopressin"., Proc. Natl. Acad. Sci. USA, vol. 94, pp. 11285-11290, (1997).
Williams, K.P., et al., "Selection of novel $Mg^{2+}$-dependent self-cleaving ribozymes" The EMBO Journal, vol. 14, No. 18, pp. 4551-4557, (1995).
Wilson, C., et al., "Functional requirements for specific ligand recognition by a biotin-binding RNA Pseudoknot"., Biochemistry, vol. 37, No. 41, pp. 14410-14419, (1998).
Wilson, C., et al., "In vitro evolution of a self-alkylating ribozyme"., Nature, vol. 374, pp. 777-782, (1995).
Wilson, C., et al., "Isolation of a fluorophore-specific DNA aptamer with weak redox activity"., Chemistry & Biology, vol. 5, No. 11, pp. 609-617, (1998).
Wilson, D.S., et al., "In vitro selection of functional nucleic acids"., Annu. Rev. Biochem. vol. 68, pp. 611-647, (1999).
Winkler, J.D., et al., "Photodynamic Fluorescent Metal Ion Sensors with Parts per Billion Sensitivity"., J. Am. Chem. Soc., vol. 120, No. 13, pp. 3237-3242, (1998).
Wittmann, C., et al.,"Microbial and Enzyme sensors for environmental monitoring"., Handbook of Biosensors and Electronic Noses: Medicine, Food, and the Environment, pp. 299-332, (1997).
Xia, P., et al., "Activation of Sphingosine Kinase by Tumor Necrosis Factor-α Inhibits Apoptosis in Human Endothelial Cells"., Journal of Biological Chemistry, vol. 274, No. 48, pp. 34499-34505, (1999).
Yan, H., et al., "DNA-Templated self-assembly of protein arrays and highly conductive nanowires"., Science, vol. 301, pp. 1882-1884, (2003).
Yang, Q., et al., "DNA ligands that bind tightly and selectively to cellobiose"., Proc. Natl. Acad. Sci. USA, vol. 95, pp. 5462-5467, (1998).

Yurke, B., et al., "A DNA-fuelled molecular machine made of DNA"., Nature, vol. 406, pp. 605-608, (2000).
Zhang, B., et al., "Peptide bond formation by in vitro selected ribozymes"., Nature, vol. 390, pp. 96-100, (1997).
Zhang, P., et al., "Design of a molecular beacon DNA probe with two fluorophores"., Angewandte Chemie International Edition, vol. 40, No. 2, pp. 402-405, (2001).
Zillmann, M., et al., "In vitro optimization of truncated stem-loop II variants of the hammerhead ribozyme for cleavage in low concentrations of magnesium under non-turnover conditions"., RNA, vol. 3, pp. 734-747, (1997).
Zimmerman, J.M., et al., "In vivo selection of spectinomycin-binding RNAs"., Nucleic Acids Research, vol. 30, No. 24, pp. 5425-5435, (2002).
Zimmermann, G.R., et al., "Molecular interactions and metal binding in the theophylline-binding core of an RNA aptamer"., RNA, vol. 6, pp. 659-667, (2000).
International Search Report dated Nov. 21, 2005 for corresponding PCT application No. PCT/US2005/001060.
Supplemental International Search Report dated Jan. 10, 2006 for corresponding PCT application No. PCT/US2005/001060.
Liu, J., et al., "Size control, metal substitution, and catalytic application of cryptomelane nanomaterials prepared using cross-linking reagents"., Chem. Mater., vol. 16, No. 2,. pp. 276-285, (2004).
Cake, K.M., et al., "Partition of circulating lead between serum and red cells is different for internal and external sources of lead"., American Journal of Industrial Medicine, vol. 29, pp. 440-445, (1996).
International Search Report dated Aug. 31, 2004 for corresponding PCT application No. PCT/US2004/002946.
Hazarika, P., et al., "Reversible switching of DNA-Gold nanoparticle aggregation"., Angewandte Chemie International Edition, vol. 43, No. 47, pp. 6469-6471, (2004).
International Search Report dated May 29, 2006 for PCT application No. PCT/US2005/037896 (related application).
Liu, J., et al., "Improving fluorescent DNAzyme biosensors by combining Inter- and Intramolecular quenchers"., Analytical Chemistry, vol. 75, No. 23, pp. 6666-6672, (2003).
Liu, J., et al., "Stimuli-responsive disassembly of nanoparticle aggregates for light-up colorimetric sensing"., Journal of the American Chemical Society, vol. 127, No. 36, pp. 12677-12683, (2005).
Abstract of: Iwasaki, K., Mizota, T., Kenkyu Hokoku—Kanagawa-ken Kogyo Shikensho 1991, 62, 57.
Storhoff, J.J., et al., "Facile colorimetric detection of polynucleotides based on gold nanoparticle probes"., Proceedings of the 1998 ERDEC Scientific Conference on Chemical and Biological Defense Research, Nov. 17-20, 1998, Aberdeen Proving Ground, pp. 221-226, (1999).
Yang, Y., et at, "Measurement of lead and magnesium in distilled spirits using inductively coupled plasma optical emission spectrometry viewed from the end"., Analytical Chemistry (Fenxi Huaxue), Chinese Journal of Analytical Chemistry, vol. 25, No. 9, pp. 1114-1117, (1997).
Cake, K.M., et at, "Partition of circulating lead between serum and red cells is different for internal and external sources of lead"., American Journal of Industrial Medicine, vol. 29, pp. 440-445, (1996).
European Search Report dated Jul. 10, 2006 for PCT application No. PCT/US2003/12576.
International Search Report dated Nov. 17, 2006 for PCT application No. PCT/US2006/001627.
Liu, J., et al., "DNAzyme-directed assembly of gold nanoparticles as colorimetric sensor for a broad range of analytes", pp. 1-3, located at http://ieeenano2003.arc.nasa.gov/THM@.pdf, (2003).
Wang, D.Y., et al., "A general approach for the use of oligonucleotide effectors to regulate the catalysis of RNA-cleaving ribozymes and DNAzymes", Nucleic Acids Research, vol. 30, No. 8, pp. 1735-1742, (2002).
Levy, M., et al., "Exponential growth by cross-catalytic cleavage of deoxyribozymogens",PNAS, vol. 100, No. 11, pp. 6416-6421, (2003).

Beyer, S., et al., "A modular DNA signal translator for the controlled release of a protein by an aptamer", Nucleic Acids Research, vol. 34, No. 5, pp. 1581-1587, (2006).

Frauendorf, C., et al., "Detection of small organic analytes by fluorescing molecular switches", Bioorganic & Medicinal Chemistry, vol. 9, pp. 2521-2524, (2001).

Glynou, K., et al., "Oligonucleotide-functionalized gold nanoparticles as probes in a dry-reagent strip biosensor for DNA analysis by hybridization", Anal. Chem, vol. 75, No. 16, pp. 4155-4160, (2003).

Liu, J., et al., "Optimization of a $Pb^{2+}$-directed gold nanoparticle/DNAzyme assembly and its application as a colorimetric biosensor for $Pb^{2+}$", Chem. Mater., vol. 16, No. 17, pp. 3231-3238, (2004).

Jones, K.D., et al., "Anniversary Essays, 3. Assay development, Changes in the development of rapid assays since 1995", Medical Devicelink, found at: http://www.devicelink.com/ivdt/archive/05/04/005.html, 3 pages, (2005).

Product Description: Pall Corporation, "Immunochromatographic, lateral flow or strip tests development ideas", found at: http://www.pall.com/34445_4154.asp, 7 pages, (1998).

Liu, J., et al., "Fast colorimetric sensing of adenosine and cocaine based on a general sensor design involving aptamers and nanoparticles", Angew. Chem. Int. Ed., vol. 45, pp. 90-94, (2006).

Liu, J., et al., "A simple and sensitive "dipstick" test in serum based on lateral flow separation of aptamer-linked nanostructures", Angewandte Chemie International Edition, vol. 45, pp. 7955-7959, (2006).

Jiang, P. et al., "Fluorescent detection of zinc in biological systems: recent development on the design of chemosensors and biosensors", Coordination Chemistry Reviews, vol. 248, pp. 205-229, (2004).

Lim, M.H. et al., "Metal-based turn-on fluorescent probes for sensing nitric oxide", Accounts of Chemical Research, vol. 40, No. 1, pp. 41-51, (2007).

Yoon, S. et al., "Screening mercury levels in fish with a selective fluorescent chemosensor", Journal of the American Chemical Society, vol. 127, pp. 16030-16031, (2005).

Yang, L. et al., "Imaging of the intracellular topography of copper with a fluorescent sensor and by synchrotron x-ray fluorescence microscopy", Proceedings of the National Academy of Science, vol. 102, No. 32, pp. 11179-11184, (2005).

He, Q. et al., "A selective fluorescent sensor for detecting lead in living cells", Journal of the American Chemical Society, vol. 128, pp. 9316-9317, (2006).

Zeng, L. et al., "A selective turn-on fluorescent sensor for imaging copper in living cells", Journal of the American Chemical Society, vol. 128, pp. 10-11, (2006).

Wegner, S.V. et al., "Design of an emission ratiometric biosensor from MerR family proteins: A sensitive and selective sensor for $Hg^{2+n}$ ", Journal of the American Chemical Society, vol. 129, pp. 3474-3475, (2007).

Nolan, E.M. et al., "Turn-on and ratiometric mercury sensing in water with a red-emitting probe", Journal of the American Chemical Society, vol. 129, pp. 5910-5918, (2007).

Sasaki, D.Y. et al., "Metal-induced dispersion of lipid aggregates: A simple, selective, and sensitive fluorescent metal ion sensor", Angew. Chem. Int. Ed. England, vol. 34, No. 8, pp. 905-907, (1995).

Torrado, A. et al., "Exploiting polypeptide motifs for the design of selective Cu(II) ion chemosensors" Journal of the American Chemical Society, vol. 120, pp. 609-610, (1998).

Grandini, P. et al., "Exploiting the self-assembly strategy for the design of selective $Cu^{II}$ ion chemosensors", Angew. Chem. Int. Ed, vol. 38, No. 20, pp. 3061-3064, (1999).

Klein, G. et al., "A fluorescent metal sensor based on macrocyclic chelation", Chem. Comm., pp. 561-562, (2001).

Zheng, Y. et al., "A new fluorescent chemosensor for copper ions based on tripeptide glycyl-histidyl-lysine (GHK)", Organic Letters, vol. 3, No. 21, pp. 3277-3280, (2001).

Boiocchi, M. et al., "A two-channel molecular dosimeter for the optical detection of copper(II)" Chem. Comm, pp. 1812-1813, (2003).

Zheng, Y. et al., "Peptidyl fluorescent chemosensors for the detection of divalent copper", Analytical Chemistry, vol. 75, No. 7, pp. 1706-1712, (2003).

Zheng, Y. et al., "Development of fluorescent film sensors for the detection of divalent copper", Journal of the American Chemical Society, vol. 125, pp. 2680-2686, (2003).

Roy, B.C. et al., "Synthesis of new, pyrene-containing metal-chelating lipids and sensing of cupric ions", Organic Letters, vol. 5, No. 1, pp. 11-14, (2003).

Kaur, S. et al., "Photoactive chemosensors 4: a $Cu^{2+}$protein cavity mimicking fluorescent chemosensor for selective $Cu^{2+}$recognition", Tetrahedron Letters, vol. 45, pp. 5081-5085, (2004).

Mei, Y. et al., "A selective and sensitive chemosensor for $Cu^{2+}$based on 8-hydroxyquinoline", Tetrahedron Letters, vol. 47, pp. 2447-2449, (2006).

Zhang, X-B. et al., "A highly selective fluorescent sensor for $Cu^{2+}$based on 2-(2'-hydroxyphenyl) benzoxazole in a poly(vinyl chloride) matrix", Analytica Chimica Acta, vol. 567, pp. 189-195, (2006).

Comba, P. et al., "Synthesis of new phenanthroline-based heteroditopic ligands—highly efficient and selective fluorescence sensors for copper (II) ions", European Journal of Inorganic Chemistry, pp. 4442-4448, (2006).

Kim, S. H. et al., "$Hg^{2+}$-selective off-on and $Cu^{2+}$-selective on-off type fluoroionophore based upon cyclam", Organic Letters, vol. 8, No. 3, pp. 371-374, (2006).

White, B. R. et al., "Fluorescent peptide sensor for the selective detection of $Cu^{2+}$", Talanta, vol. 71, pp. 2015-2020, (2007).

Oter, O. et al., "Spectral characterization of a newly synthesized fluorescent semicarbazone derivative and its usage as a selective fiber optic sensor for copper(II)", Analytica Chimica Acta, vol. 584, pp. 308-314, (2007).

Dujols, V. et al., "A long-wavelength fluorescent chemodosimeter selective for Cu(II) ion in water", Journal of the American Chemical Society, vol. 119, pp. 7386-7387, (1997).

Yang, J-S. et al., "$Cu^{2+}$-induced blue shift of the pyrene excimer emission: a new signal transduction mode of pyrene probes", Organic Letters, vol. 3, No. 6, pp. 889-892, (2001).

Kaur, S. et al., "Photoactive chemosensors 3: a unique case of fluorescence enhancement with Cu(II)", Chem. Comm., pp. 2840-2841, (2002).

Wu, Q. et al., "Catalytic signal amplification using a heck reaction. An example in the fluorescence sensing of Cu(II)", Journal of the American Chemical Society, vol. 126, pp. 14682-14683, (2004).

Royzen, M. et al., "Ratiometric displacement approach to Cu(II) sensing by fluorescence", Journal of the American Chemical Society, vol. 127, pp. 1612-1613, (2005).

Xu, Z. et al., "Ratiometric and selective fluorescent sensor for $Cu^{II}$ based on internal charge transfer (ICT)", Organic Letters, vol. 7, No. 5, pp. 889-892, (2005).

Wen, Z-C. et al., "A highly selective charge transfer fluoroionophore for $Cu^{2+}$", Chem. Commun., pp. 106-108, (2006).

Yang, H. et al., "Highly selective ratiometric fluorescent sensor for Cu(II) with two urea groups", Tetrahedron Letters, vol. 47, pp. 2911-2914, (2006).

Martinez, R. et al., "2-aza-1,3-butadiene derivatives featuring an anthracene or pyrene unit: highly selective colorimetric and fluorescent signaling of $Cu^{2+}$cation", Organic Letters, vol. 8, No. 15, pp. 3235-3238, (2006).

Navani, N. K. et al., "Nucleic acid aptamers and enzymes as sensors", Current Opinion in Chemical Biology, vol. 10, pp. 272-281, (2006).

Liu, J. et al., "A catalytic beacon sensor for uranium with parts-per-trillion sensitivity and millionfold selectivity", Proceedings of the National Academy of Science, vol. 104, No. 7, pp. 2056-2061, (2007).

Georgopoulos, P.G. et al., "Environmental copper: its dynamics and human exposure issues", Journal of Toxicology and Environmental Health, Part B, vol. 4, pp. 341-394, (2001).

Hertzberg, R.P. et al., "Cleavage of DNA with methidiumpropyl-EDTA-iron(II): reaction conditions and product analyses", Biochemistry, vol. 23, pp. 3934-3945, (1984).

Yazzie, M. et al., "Uranyl acetate causes DNA single strand breaks in vitro in the presence of ascorbate (Vitamin C)", Chem. Res. Toxicol., vol. 16, pp. 524-530, (2003).

Bolletta, F. et al., "A [Ru$^{II}$ (bipy)$_3$]-[1,9-diamino-3,7-diazanonane-4,6-dione] two-component system as an efficient on-off luminescent chemosensor for Ni$^{2+}$ and Cu$^{2+}$ in water, based on an ET (energy transfer) mechanism", Journal of the Chemical Society, Dalton Transactions, pp. 1381-1385, (1999).

Carmi, N. et al., "Characterization of a DNA-cleaving deoxyribozyme", Bioorganic & Medicinal Chemistry, vol. 9, issue 10, pp. 2589-2600, (2001).

Liu, J. et al., "A DNAzyme catalytic beacon sensor for paramagnetic Cu$^{2+}$ ions in aqueous solution with high sensitivity and selectivity", Journal of the American Chemical Society, 2 pages, (2007), ASAP Web Release Date: Jul. 24, 2007.

Tanaka, K. et al., "Programmable self-assembly of metal ions inside artificial DNA duplexes", Nature Nanotechnology, vol. 1, pp. 190-194, (2006).

Achenbach, J.C. et al., "DNAzymes: From creation in vitro to application in vivo", Current Pharmaceutical Biotechnology, vol. 5, pp. 321-336, (2004).

Balaji, T. et al., "Optical sensor for the visual detection of mercury using mesoporous silica anchoring porphyrin moiety", The Analyst, vol. 130, pp. 1162-1167, (2005).

Caballero, A. et al., "Highly selective chromogenic and redox or fluorescent sensors of Hg$^{2+}$ in aqueous environment based on 1,4-disubstituted azines", Journal of the American Chemical Society, vol. 127, pp. 15666-15667, (2005).

Chan, W.H. et al., "Development of a mercury ion-selective optical sensor based on fluorescence quenching of 5,10,15,20-tetraphenylporphyrin", Analytica Chimica Acta, vol. 444, pp. 261-269, (2001).

Chen, P. et al., "A general strategy to convert the merR family proteins into highly sensitive and selective fluorescent biosensors for metal ions", Journal of the American Chemical Society, vol. 126, pp. 728-729, (2004).

Chiuman, W. et al., "Efficient signaling platforms built from a small catalytic DNA and doubly labeled fluorogenic substrates", Nucleic Acids Research, vol. 35, No. 2, pp. 401-405, (2007).

Cruz, R.P.G. et al., "Dinucleotide junction cleavage versatility of 8-17 deoxyribozyme", Chemistry & Biology, vol. 11, pp. 57-67, (2004).

Frasco, M.F. et al., "Mechanisms of cholinesterase inhibition by inorganic mercury", the FEBS Journal, vol. 274, pp. 1849-1861, (2007).

Guo, X. et al., "A highly selective and sensitive fluorescent chemosensor for Hg$^{2+}$ in neutral buffer aqueous solution", The Jouranl of the American Chemical Society, vol. 126, pp. 2272-2273, (2004).

Harris, H.H. et al., "The chemical form of mercury in fish", Science, vol. 301, pp. 1203, (2003).

Ha-Thi, M-H. et al., "Highly selective and sensitive phosphane sulfide derivative for the detection of HG$^{2+}$ in an organoaqueous medium", Organic Letters, vol. 9, No. 6, pp. 1133-1136, (2007).

Joyce, G.F. et al., "Directed evolution of nucleic acid enzymes", Annual Review Biochem., vol. 73, pp. 791-836, (2004).

Ko, S-K. et al., "In vivo monitoring of mercury ions using a rhodamine-based molecular probe", Journal of the American Chemical Society, vol. 128, pp. 14150-14155, (2006).

Kuswandi, B. et al., "Capillary optode: determination of mercury(II) in aqueous solution", Analytical Letters, vol. 32, No. 9. 4, pp. 649-664, (1999).

Kuswandi, B. et al., "Selective pool optode for mercury ion sensing in aqueous solution", Sensors and Actuators B, vol. 74, pp. 131-137, (2001).

Lee, J-S. et al., "Colorimetric detection of mercuric ion (HG$^{2+}$) in aqueous media using DNA-functionalized gold nanoparticles", Angewandte Chemie International Edition, vol. 46, pp. 4093-4096, (2007).

Liu, B. et al., "A selective fluorescent ratiometric chemodosimeter for mercury ion", Chem. Communications, pp. 3156-3158, (2005).

Liu, J. et al., "Fluorescent DNAzyme biosensors for metal ions based on catalytic molecular beacons", Methods in Molecular Biology, vol. 335, pp. 275-288, (2006).

Matsushita, M. et al., "A blue fluorescent antibody-cofactor sensor for mercury", Organic Letters, vol. 7, No. 22, pp. 4943-4946, (2005).

Miyake, Y. et al., "Mercury$^{II}$-mediated formation of thymine-Hg$^{II}$-thymine base pairs in DNA duplexes", Journal of the American Chemical Society, vol. 128, No. 7, pp. 2172-2173, (2006).

Nolan, E.M. et al., "A "turn-on" fluorescent sensor for the selective detection of mercuric ion in aqueous media", Journal of the American Chemical Society, vol. 125, pp. 14270-14271, (2003).

Ono, A. et al., "highly selective oligonucleotide-based sensor for mercury (II) in aqueous solutions", Angew. Chem. Int. Ed., vol. 43, pp. 4300-4302, (2004).

Ostatna, V. et al., "Self-assembled monolayers of thiol-end-labeled DNA at mercury electrodes", Langmuir, vol. 22, pp. 6481-6484, (2006).

Prodi, L. et al., "An effective fluorescent achemosensor for mercury ions", Journal of the American Chemical Society, vol. 122, No. 28, pp. 6769-6770, (2000).

Silverman, S.K., "Survey and Summary: In vitro selection, characterization, and application of deoxyribozymes that cleave RNA", Nucleic Acids Research, vol. 33, No. 19, pp. 6151-6163, (2005).

Song, K.C. et al., "Fluorogenic Hg$^{2+}$-selective chemodosimeter derived from 8-hydroxyquinoline", Organic Letters, vol. 8, No. 16, pp. 3413-3416, (2006).

Szurdoki, F. et al., "A combinatorial approach to discover new chelators for optical metal ion sensing", Analytical Chemistry, vol. 72, No. 21, pp. 5250-5257, (2000).

Tanaka, Y. et al., "$^{15}$N-$^{15}$N J-coupling across Hg$^{II}$: Direct observation of Hg$^{II}$-mediated T-T base pairs in a DNA duplex" Journal of the American Chemical Society, vol. 129, No. 2, pp. 244-245, (2007).

Jacoby, M. "Mercury Sensor—Analytical Chemistry: Colorimetric method is sensitive and selective", Chemical & Engineering News, pp. 15, May 7, 2007.

Vannela, R. et al., "In vitro selection of Hg (II) and as (V)-dependent RNA-cleaving DNAzymes", Environmental Engineering Science, vol. 24, No. 1, pp. 73-84, (2007).

Vaughan, A.A. et al., "Optical fibre reflectance sensors for the detection of heavy metal ions based on immobilized Br-PADAP", Snesors and Actuators B, vol. 51, pp. 368-376, (1998).

Virta, M. et al., "A luminescence-based mercury biosensor", Analytical Chemistry, vol. 67, No. 3, pp. 667-669, (1995).

Wang, J. et al., "Detecting Hg$^{2+}$ ions with an ICT fluorescent sensor molecule: Remarkable emission spectra shift and unique selectivity", Journal of Organic Chemistry, vol. 71, pp. 4308-4311, (2006).

Wang, J. et al., "A series of polyamide receptor based PET fluorescent sensor molecules: Positively cooperative Hg$^{2+}$ ion binding with high sensitivity", Organic Letters, vol. 8, No. 17, pp. 3721-3724, (2006).

Widmann, A. et al., "Mercury detection in seawater using a mercaptoacetic acid modified gold microwire electrode", Electroanalysis, vol. 17, No. 10, pp. 825-831, (2005).

Xiao, Y. et al., "Electrochemical detection of parts-per-billion lead via an electrode-bound DNAzyme assembly", Journal of the American Chemical Society, vol. 129, pp. 262-263, (2007).

Yang, W. et al., "Solid phase extraction and spectrophotometric determination of mercury in tobacco and tobacco additives with 5-(p-aminobenzylidene)-thiothiorhodanine", Journal of the Brazilian Chemical Society, vol. 17, No. 5, pp. 1039-1044, (2006).

Yang, Y-K. et al., "A rhodamine-based fluorescent and colorimetric chemodosimeter for the rapid detection of Hg2+ ions in aqueous media", Journal of the American Chemical Society, vol. 127, pp. 16760-16761, (2005).

Zhang, X-B. et al "An optical fiber chemical sensor for mercury ions based on a porphyrin dimmer", Analytical Chemistry, vol. 74, No. 4, pp. 821-825, (2002).

Zhao, Y. et al., "A "turn-on" fluorescent sensor for selective Hg(II) detection in aqueous media based on metal-induced dye formation", Inorganic Chemistry, vol. 45, No. 25, pp. 10013-10015, (2006).

Zhao, Y. et al., "Tuning the sensitivity of a foldamer-based mercury sensor by its folding energy", Journal of the American Chemical Society, vol. 128, No. 31, pp. 9988-9989, (2006).

Zhao, Y. et al., "Detection of Hg2+ in aqueous solutions with a foldamer-based fluorescent sensor modulated by surgactant micelles", Organic Letters, vol. 8, No. 21, pp. 4715-4717, (2006).

Zuker, M., "Mfold web server for nucleic acid folding and hybridization prediction", Nucleic Acids Research, vol. 31, No. 13, pp. 3406-3415, (2003).

International Search Report dated May 10, 2007 for PCT application No. PCT/US2006/030617.

Liu, J. et al., "Adenosine-dependent assembly of aptazyme-functionalized gold nanoparticles and its application as a colorimetric biosensor", Analytical Chemistry, vol. 76, No. 6, pp. 1627-1632, (2004).

Liu, J. et al., "Smart nanomaterials responsive to multiple chemical stimuli with controllable cooperativity", Advanced Materials, vol. 18, No. 13, pp. 1667-1671, (2006).

Nutiu, R. et al., "Signaling aptamers for monitoring enzymatic activity and for inhibitor screening", Chembiochem—A European Journal of Chemical Biology, vol. 5, No. 8, pp. 1139-1144, (2004).

Nutiu, R. et al., "Structure-switching signaling aptamers: Transducing molecular recognition into fluorescence signaling", Chemistry—A European Journal, vol. 10, No. 8, pp. 1868-1876, (2004).

International Search Report dated Jul. 31, 2007 for PCT application No. PCT/US2007/064055.

Ahern, H., "Biochemical, reagent kits offer scientists good return on investment", The Scientist, vol. 9, No. 15, pp. 20-22, (1995).

Homann, M. et al., "Dissociation of long-chain duplex RNA can occur via strand displacement in vitro: biological implication", Nucleic Acids Research, vol. 24, No. 22, pp. 4395-4400, (1996).

Alivisatos, A.P. et al., "Quantum dots as cellular probes", Annual Review Biomed. Eng, vol. 7, pp. 55-76, (2005).

Dyadyusha, L. et al., "Quenching of CdSe quantum dot emission, a new approach for biosensing", Chemical Communication, pp. 3201-3203, (2005).

Ellington, A.D. et al., "In vitro selection of RNA molecules that bind specific ligands", Nature, vol. 346, pp. 818-822, (1990).

Gerion, D. et al., "Room-temperature single-nucleotide polymorphism and multiallele DNA detection using fluorescent nanocrystals and microarrays", Analytical Chemistry, vol. 75, No. 18, pp. 4766-4772, (2003).

Goldman, E.R. et al., "Multiplexed toxin analysis using four colors of quantum dot fluororeagents", Analytical Chemistry, vol. 76, No. 3, pp. 684-688, (2004).

Gueroui, Z. et al., "Single-molecule measurements of gold-quenched quantum dots", Physical Review Letters, vol. 93, No. 16, pp. 166108/1-166108/4, (2004).

Han, M. et al., "Quantum-dot-tagged microbeads for multiplexed optical coding of biomolecules", Nature Biotechnology, vol. 19, pp. 631-635, (2001).

Hansen, J.A. et al., "Quantum-dot/Aptamer-based ultrasensitive multi-analyte electrochemical biosensor", Journal of the American Chemical Society, vol. 128, No. 7, pp. 2228-2229, (2006).

Hartig, J.S. et al., "Protein-dependent ribozymes report molecular interactions in real time", Nature Biotechnology, vol. 20, pp. 717-722, (2002).

Herman, T. et al., "Adaptive recognition by nucleic acid aptamers", Science, vol. 287, pp. 820-825, (2000).

Kurreck, J., "Antisense technologies Improvement through novel chemical modifications", Eur. J. Biochem, vol. 270, pp. 1628-1644, (2003).

Lee, J.F. et al., "Aptamer database", Nucleic Acids Research, vol. 32, Database Issue, pp. D95-D100, (2004).

Levy, M. et al., "Quantum-dot aptamer beacons for the detection of proteins", ChemBioChem, vol. 6, pp. 2163-2166, (2005).

Liu, J. et al., "Smart nanomaterials responsive to multiple chemical stimuli with controllable cooperativity", Advanced Materials, vol. 18, pp. 1667-1671, (2006).

Liu, J. et al., "Preparation of aptamer-linked gold nanoparticle purple aggregates for colorimetric sensing of analytes", Nature Protocols, vol. 1, No. 1, pp. 246-252, (2006).

Medintz, I.L. et al., "Quantum dot bioconjugates for imaging, labeling and sensing", Nature Materials, vol. 4, pp. 435-446, (2005).

Miduturu, C. V. et al., "Modulation of DNA constraints that control macromolecular folding", Angew. Chem. Int. Ed., vol. 45, pp. 1918-1921, (2006).

Mitchell, G.P. et al., "Programmed assembly of DNA functionalized quantum dots", Journal of the American Chemical Society, vol. 121, No. 35, pp. 8122-8123, (1999).

Nutiu, R. et al., "Structure-switching signaling aptamers: Transducing molecular recognition into fluorescence signaling", Chem. Eur. J., vol. 10, pp. 1868-1876, (2004).

Oh, E. et al., "Inhibition assay of biomolecules based on fluorescence resonance energy transfer (FRET) between quantum dots and gold nanoparticles", Journal of the American Chemical Society, vol. 127, No. 10, pp. 3270-3271, (2005).

Rajendran, M. et al., "In vitro selection of molecular beacons", Nucleic Acids Research, vol. 31, No. 19, pp. 5700-5713, (2003).

Vet, J.A.M. et al., "Multiplex detection of four pathogenic retroviruses using molecular beacons", Proceedings of the National Academy of Science, USA., vol. 96, pp. 6394-6399, (1999).

Wargnier, R. et al., "Energy transfer in aqueous solutions of oppositely charged CdSe/ZnS core/shell quantum dot-nanogold assemblies", Nano Letters, vol. 4, No. 3, pp. 451-457, (2004).

Wilson, R. et al., "Encoded microcarriers for high-throughput multiplexed detection", Angewandte Chemie International Edition, vol. 45, pp. 6104-6117, (2006).

Winkler, W.C. et al., "Regulation of bacterial gene expression by riboswitches", The Annual Review of Microbiology, vol. 59, pp. 487-517, (2005).

Yang, C.J. et al., "Light-switching excimer probes for rapid protein monitoring in complex biological fluids", PNAS, vol. 102, No. 48, pp. 17278-17283, (2005).

Liu, J. et al., "Quantum dot encoding of aptamer-linked nanostructures for one-pot simultaneous detection of multiple analytes", Analytical Chemistry, vol. 79, No. 11, pp. 4120-4125, (2007).

Lu, Y. et al., "Smart nanomaterials inspired by biology: Dynamic assembly of error-free nanomaterials in response to multiple chemical and biological stimuli", Accounts of Chemical Research, vol. 40, No. 5, pp. 315-323, (2007).

Allen, M.J. et al., "Magnetic resonance contrast agents for medical and molecular imaging", Met. Ions Biol. Syst., vol. 42, pp. 1-38, (2004).

Artemov, D. et al., "MR molecular imaging of the Her-2/neu receptor in breast cancer cells using targeted iron oxide nanoparticles", Magnetic Resonance in Medicine, vol. 49, pp. 403-408, (2003).

Buerger, C. et al., "Sequence-specific peptide aptamers, interacting with the intracellular domain of the epidermal growth factor receptor, interfere with stat3 activation and inhibit the growth of tumor cells", The Journal of Biological Chemistry, vol. 278, No. 39, pp. 37610-37621, (2003).

Buerger, C. et al., "Bifunctional recombinant proteins in cancer therapy: cell penetrating peptide aptamers as inhibitors of growth factor signaling", J. Cancer Research Clin. Oncol., vol. 129, pp. 669-675, (2003).

Carr, D.H. et al., "Gadolinium-DTPA as a contrast agent in MRI: initial clinical experience in 20 patients", American Journal of Roentfenol., vol. 143, pp. 215-224, (1984).

Chen, Y. et al., "An autonomous DNA nanomotor powered by a DNA enzyme", Angew. Chem. Int. Ed., vol. 43, pp. 3554-3557, (2004).

Corot, C. et al., "Macrophage imaging in central nervous system and in carotid atherosclerotic plaque using ultrasmall superparamagnetic iron oxide in magnetic resonance imaging", Investigative Radiology, vol. 39, No. 10, pp. 619-625, (2004).

Dodd, C.H. et al., "Normal T-cell response and in vivo magnetic resonance imaging of T cells loaded with HIV transactivator-peptide-derived superparamagnetic nanoparticles", Journal of Immunological Methods, vol. 256, pp. 89-105, (2001).

Drolet, D.W. et al., "An enzyme-linked oligonucleotide assay", Nature Biotechnology, vol. 14, pp. 1021-1025, (1996).

Enochs, W.S. et al., "Improved delineation of human brain tumors on MR images using a long-circulating, superparamagnetic iron oxide agent", Journal of Magnetic Resonance Imaging, vol. 9, pp. 228-232, (1999).

Famulok, M. et al., "Nucleic acid aptamers-from selection in vitro to applications in vivo", Accounts of Chemical research, vol. 33, No. 9, pp. 591-599, (2000).

Fang, X. et al., "Molecular aptamer for real-time oncoprotein platelet-derived growth factor monitoring by fluorescence anisotropy", Analytical Chemistry, vol. 73, No. 23, pp. 5752-5757, (2001).

Frullano, L. et al., "Synthesis and characterization of a doxorubicin-Gd(III) contrast agent conjugate: A new approach toward prodrug-procontrast complexes", Inorganic Chemistry, vol. 45, No. 21, pp. 8489-8491, (2006).

Hamaguchi, N. et al., "Aptamer beacons for the direct detection of proteins", Analytical Biochemistry, vol. 294, pp. 126-131, (2001).

Harisinghani, M.G. et al., "Noninvasive detection of clinically occult lymph-node metastases in prostate cancer", The New England Journal of Medicine, vol. 348, No. 25, pp. 2491-2499, (2003).

Hermann, T. et al., "Adaptive recognition by nucleic acid aptamers", Science, vol. 287, pp. 820-825, (2000).

Hoppe-Seyler, F. et al., "Peptide aptamers: Specific inhibitors of protein function", Current Molecular Medicine, vol. 4, pp. 529-538, (2004).

Huang, C-C. et al., "Aptamer-modified gold nanoparticles for colorimetric determination of platelet-derived growth factors and their receptors", Analytical Chemistry, vol. 77, No. 17, pp. 5735-5741, (2005).

Josephson, L. et al., "High-efficiency intracellular magnetic labeling with novel superparamagnetic-tat peptide conjugates", Bioconjugate Chem., vol. 10, No. 2, pp. 186-191, (1999).

Josephson, L. et al., "The effects of iron oxides on proton relaxivity", Magnetic Resonance Imaging, vol. 6, pp. 647-653, (1988).

Josephson, L. et al., "Magnetic nanosensors for the detection of oligonucleotide sequences", Angew. Chem. Int. Ed., vol. 40, No. 17, pp. 3204-3206, (2001).

Kabalka, G. et al., "Gadolinium-labeled liposomes: Targeted MR contrast agents for the liver and spleen", Radiology, vol. 163, pp. 255-258, (1987).

Kooi, M.E. et al., "Accumulation of ultrasmall superparamagnetic particles of iron oxide in human atherosclerotic plaques can be detected by in vivo magnetic resonance imaging", Circulation, vol. 107, pp. 2453-2458, (2003).

Kresse, M. et al., "Targeting of ultrasmall superparamagnetic iron oxide (USPIO) particles to tumor cells in vivo by using transferring receptor pathways", Magn. Reson. Med., vol. 40, pp. 236-242, (1998).

Lee, J. et al., "A steroid-conjugated contrast agent for magnetic resonance imaging of cell signaling", Journal of American Chemical Society, vol. 127, No. 38, pp. 13164-13166, (2005).

Lewin, M. et al., "Tat peptide-derivatized magnetic nanoparticles allow in vivo tracking and recovery of progenitor cells", Nature Biotechnology, vol. 18, pp. 410-414, (2000).

Li, J.J. et al., "Molecular aptamer beacons for real-time protein recognition", Biochemical and Biophysical Research Communications, vol. 292, No. 1, pp. 31-40, (2002).

Li, W-H. et al., "A calcium-sensitive magnetic resonance imaging contrast agent", Journal of the American Chemical Society, vol. 121, No. 6, pp. 1413-1414, (1999).

Lin, C.H. et al., "Structural basis of DNA folding and recognition in an AMP-DNA aptamer complex: distinct architectures but common recognition motifs for DNA and RNA aptamers complexed to AMP", Chemistry and Biology, vol. 4, pp. 817-832, (1997).

Liss, M. et al., "An aptamer-based quartz crystal protein biosensor", Analytical Chemistry, vol. 74, No. 17, pp. 4488-4495, (2002).

Liu, Y. et al., "Aptamer-directed self-assembly of protein arrays on a DNA nanostructure", Angew. Chem. Int. Ed., vol. 44, pp. 4333-4338, (2005).

Macaya, R.F. et al., "Thrombin-binding DNA aptamer forms a unimolecular quadruplex structure in solution", Proceedings of the National Academy of Science USA, vol. 90, pp. 3745-3749, (1993).

Nagel-Wolfrum, K. et al., "The interaction of specific peptide aptamers with the DNA binding domain and the dimerization domain of the transcription factor stat3-inhibits transactivation and induces apoptosis in tumor cells", Molecular Cancer Research, vol. 2, pp. 170-182, (2004).

Nitin, N. et al., "Functionalization and pepride-based delivery of magnetic nanoparticles as an intracellular MRI contrast agent", J. Biol. Inorg. Chem., vol. 9, pp. 706-712, (2004).

Nutiu, R. et al., "Engineering DNA aptamers and DNA enzymes with fluorescence-signaling properties", Pure Appl. Chem., vol. 76, Nos. 7-8, pp. 1547-1561, (2004).

Nutiu, R. et al., "Structure-switching signaling aptamers: Transducing molecular recognition into fluorescence signaling", Chem. Eur. J., vol. 10, pp. 1868-1876, (2004).

Padmanabhan, K. et al., "The structure of a-thrombin inhibited by a 15-mer single-stranded DNA aptamer", The Journal of Biological Chemistry, vol. 268, No. 24, pp. 17651-17654, (1993).

Pavlov, V. et al., "Aptamer-functionalized au nanoparticles for the amplified optical detection of thrombin", The Journal of the American Chemical Society, vol. 126, No. 38, pp. 11768-11769, (2004).

Pendergrast, P.S. et al., "Nucleic acid aptamers for target validation and therapeutic applications", Journal of Biomolecular Techniques, vol. 16, issue 3, pp. 224-234, (2005).

Perez, J.M. et al., "Use of magnetic nanoparticles as nanosensors to probe for molecular interactions", ChemBioChem, vol. 5, pp. 261-264, (2004).

Perez, J.M. et al., "Viral-induced self-assembly of magnetic nanoparticles allows the detection of viral particles in biological media", Journal of the American Chemical Society, vol. 125, No. 34, pp. 10192-10193, (2003).

Radi, A-E. et al., "Reagentless, reusable, ultrasensitive electrochemical molecular beacon aptasensor", Journal of the American Chemical Society, vol. 128, No. 1, pp. 117-124, (2006).

Saeed, M. et al., "Occlusive and reperfused myocardial infarcts: differentiation with Mn-DPDP-enhanced MR imaging", Radiology, vol. 172, pp. 59-64, (1989).

Shen, T. et al., "Monocrystalline iron oxide nanocompounds (MION): Physicochemical properties", Magn. Reson. Med., vol. 29, pp. 599-604, (1993).

Soriaga, M.P. et al., "Determination of the orientation of adsorbed molecules at solid-liquid interfaces by thin-layer electrochemistry: Aromatic compounds at platinum electrodes", Journal of the American Chemical Society, vol. 104, pp. 2735-2742, (1982).

Soriaga, M.P. et al., "Determination of the orientation of aromatic molecules adsorbed on platinum electrodes: The influence of iodide a surface-active anion", Journal of the American Chemical Society, vol. 104, pp. 2742-2747, (1982).

Soriaga, M.P. et al., "Determination of the orientation of aromatic molecules adsorbed on platinum electrodes: The effect of solute concentration", Journal of the American Chemical Society, vol. 104, pp. 3937-3945, (1982).

Sosnovik, D.E. et al., "Emerging concepts in molecular MRI", Current Opinion in Biotechnology, vol. 18, pp. 4-10, (2007).

Taboada, E. et al., "Relaxometric and magnetic characterization of ultrasmall iron oxide nanoparticles with high magnetization. Evaluation as potential $T_1$ magnetic resonance imaging contrast agents for molecular imaging", Langmuir, vol. 23, No. 8, pp. 4583-4588, (2007).

Tasset, D.M. et al., "Oligonucleotide inhibitors of human thrombin that bind distinct epitopes", J. Mol. Biol., vol. 272, pp. 688-698, (1997).

Tian, Y. et al., "DNAzyme amplification of molecular beacon signal", Talanta, vol. 67, pp. 532-537, (2005).

Tompkins, H.G. et al., "The study of the gas-solid interaction of acetic acid with a cuprous oxide surface using reflection-absorption spectroscopy", Journal of colloid and interface science, vol. 49, No. 3, pp. 410-421, (1974).

Tsourkas, A. et al., "Magnetic relaxation switch immunosensors detect enantiomeric impurities", Angew. Chem. Int. Ed., vol. 43, pp. 2395-2399, (2004).

Wang, S. et al., "Core/shell quantum dots with high relaxivity and photoluminescence for multimodality imaging", Journal of the American Chemical Society, vol. 129, No. 13, pp. 3848-3856, (2007).

Weissleder, R. et al., "MR imaging of splenic metastases: Ferrite-enhanced detection in rats", American Journal Roentgenol., vol. 149, pp. 723-726, (1987).

Xiao, Y. et al., "Label-free electronic detection of thrombin in blood serum by using an aptamer-based sensor", Angew. Chem. Int. Ed., vol. 44, pp. 5456-5459, (2005).

Xiao, Y. et al., "A reagentless signal-on architecture for electronic, aptamer-based sensors via target-induced strand displacement", Journal of the American Chemical Society, vol. 127, No. 51, pp. 17990-17991, (2005).

Xu, D. et al., "Label-free electrochemical detection for aptamer-based array electrodes", Analytical Chemistry, vol. 77, No. 16, pp. 6218-6224, (2005).

Yamamoto, R. et al., "Molecular beacon aptamer fluoresces in the presence of Tat protein of HIV-1", Genes to Cells, vol. 5, pp. 389-396, (2000).

Zhao, M. et al., "Magnetic sensors for protease assays", Angew. Chem. Int. Ed., vol. 42, No. 12, pp. 1375-1378, (2003).

Zhao, M. et al., "Differential conjugation of tat peptide to superparamagnetic nanoparticles and its effect on cellular uptake", Bioconjugate Chem., vol. 13, pp. 840-844, (2002).

Liu, J. et al., "Colorimetric Cu2+ detection with a ligation DNAzyme and nanoparticles", Chemical Communications, Advance Articles, DOI: 10.1039/b712421j, 6 pages, Oct. 24, 2007.

Liu, J. et al., "Non-Base pairing DNA provides a new dimension for controlling aptamer-linked nanoparticles and sensors", Journal of the American Chemical Society, vol. 129, No. 27, pp. 8634-8643, (2007).

Liu, J. et al., "Supporting Information for Colorimetric Cu2+ detection with a ligation DNAzyme and nanoparticles", Chemical Communications, Advance Articles, 4 pages, Oct. 24, 2007.

Stratagene Catolog, "Gene Characterization Kits", 2 pages, (1988).

* cited by examiner

SEQUENCE LISTING

<160> NUMBER OF SEQ ID NOS: 9

<210> SEQ ID NO 1
<211> LENGTH: 33
<212> TYPE: DNA
<213> ORGANISM: Artificial sequence
<220> FEATURE:
<223> OTHER INFORMATION: synthetic oligonucleotide

<400> SEQUENCE: 1
catctcttct ccgagccggt cgaaatagtg agt                    33

<210> SEQ ID NO 2
<211> LENGTH: 20
<212> TYPE: DNA
<213> ORGANISM: Artificial sequence
<220> FEATURE:
<223> OTHER INFORMATION: artificial oligonucleotide
<220> FEATURE:
<221> NAME/KEY: misc_feature
<222> LOCATION: (10)..(10)
<223> OTHER INFORMATION: r denotes a single ribonucleotide, such as
      adenosine ribonucleotide

<400> SEQUENCE: 2
actcactatr ggaagagatg                                   20

<210> SEQ ID NO 3
<211> LENGTH: 4
<212> TYPE: DNA
<213> ORGANISM: artificial sequence
<220> FEATURE:
<223> OTHER INFORMATION: variable region

<400> SEQUENCE: 3 tatt                                                     4

<210> SEQ ID NO 4
<211> LENGTH: 19
<212> TYPE: DNA
<213> ORGANISM: artificial sequence
<220> FEATURE:
<223> OTHER INFORMATION: synthesized polynucleotide
<220> FEATURE:
<221> NAME/KEY: Misc.
<222> LOCATION: (11)..(11)
<223> OTHER INFORMATION: ra denotes a single ribonucleotide, such as
      adenosine ribonucleotide

<400> SEQUENCE: 4
gactcactat rggaagaga                                    19

<210> SEQ ID NO 5
<211> LENGTH: 38
<212> TYPE: DNA
<213> ORGANISM: Artificial sequence
<220> FEATURE:
<223> OTHER INFORMATION: synthesized polynucleotide

<400> SEQUENCE: 5
tctcttctcc gagccggtcg aaatattgga ggaagctc                38

<210> SEQ ID NO 6
<211> LENGTH: 22
<212> TYPE: DNA
<213> ORGANISM: Artificial sequence -continued

```
<220> FEATURE:
<223> OTHER INFORMATION: synthesized polynucleotide

<400> SEQUENCE: 6
gagctggagg aaaaagtgag tc                                              22

<210> SEQ ID NO 7
<211> LENGTH: 43
<212> TYPE: DNA
<213> ORGANISM: Artificial sequence
<220> FEATURE:
<223> OTHER INFORMATION: synthesized polynucleotide
<220> FEATURE:
<221> NAME/KEY: Misc.
<222> LOCATION: (23)..(23)
<223> OTHER INFORMATION: r indicates single ribonucleotide, such as
      adenosine ribonucleotide

<400> SEQUENCE: 7
actcatctgt gagactcact atrggaagag atgtcaactc gtg                       43

<210> SEQ ID NO 8
<211> LENGTH: 50
<212> TYPE: DNA
<213> ORGANISM: Artificial sequence
<220> FEATURE:
<223> OTHER INFORMATION: synthesized polynucleotide

<400> SEQUENCE: 8
cacgagttga catctcttct ccgagccggt cgaaatattg gaggaagctc                50

<210> SEQ ID NO 9
<211> LENGTH: 34
<212> TYPE: DNA
<213> ORGANISM: Artificial sequence
<220> FEATURE:
<223> OTHER INFORMATION: synthesized polynucleotide

<400> SEQUENCE: 9
gagctggagg aaaaagtgag tctcacagat gagt                                 34
```

NUCLEIC ACID BIOSENSORS

FEDERALLY SPONSORED RESEARCH OR DEVELOPMENT

The subject matter of this application may in part have been funded by the Department of Energy (DEFG02-01ER63179) and the National Science Foundation (DMR-0117792). The government may have certain rights in this invention

BACKGROUND

Long considered strictly genetic material, DNA was shown in 1994 to be able to act as an enzyme (Breaker and Joyce 1994). Like RNAzymes, DNAzymes can catalyze nucleic acid and phosphoramidate bond cleavage, ligation, phopshorylation, and porphyrin metallation (Lu 2002). Because of their stability and catalytic capabilities, DNAzymes promise to be important in a large array of applications (Lu 2002).

Aptamers are nucleic acids (such as DNA or RNA) that recognize targets with high affinity and specificity (Ellington and Szostak 1990, Jayasena 1999). Aptazymes (also called allosteric DNA/RNAzymes or allosteric (deoxy)ribozymes) are DNA/RNAzymes regulated by an effector (the target molecule). They typically contain an aptamer domain that recognizes an effector and a catalytic domain (Hesselberth et al. 2000, Soukup and Breaker 2000, Tang and Breaker 1997). The effector can either decrease or increase the catalytic activity of the aptazyme through specific interactions between the aptamer domain and the catalytic domain. Therefore, the activity of the aptazyme can be used to monitor the presence and quantity of the effector. This strategy has been used to select and design aptazyme sensors for diagnostic and sensing purposes (Breaker 2002, Robertson and Ellington 1999, Seetharaman et al. 2001). DNA aptazymes are the most attractive candidate for sensor development because DNA is much less expensive to synthesize and more stable than RNA. In addition, general strategies to design DNA aptazymes, by introducing aptamer motifs close to the catalytic core of DNAzymes, are available (Wang et al. 2002). High cleavage activity requires the presence of effector molecules that upon binding to the aptamer motif, can allosterically modulate the activity of the catalytic core part of the aptazyme.

In vitro selection methods can be used to obtain aptamers for a wide range of target molecules with exceptionally high affinity, having dissociation constants as high as in the picomolar range (Brody and Gold 2000, Jayasena 1999, Wilson and Szostak 1999). For example, aptamers have been developed to recognize metal ions such as Zn(II) (Ciesiolka et al. 1995) and Ni(II) (Hofmann et al. 1997); nucleotides such as adenosine triphosphate (ATP) (Huizenga and Szostak 1995); and guanine(Kiga et al. 1998); co-factors such as NAD (Kiga et al. 1998) and flavin (Lauhon and Szostak 1995); antibiotics such as viomycin (Wallis et al. 1997) and streptomycin (Wallace and Schroeder 1998); proteins such as HIV reverse transcriptase (Chaloin et al. 2002) and hepatitis C virus RNA-dependent RNA polymerase (Biroccio et al. 2002); toxins such as cholera whole toxin and staphylococcal enterotoxin B (Bruno and Kiel 2002) and bacterial spores such as the anthrax (Bruno and Kiel 1999). Compared to antibodies, DNA/RNA based aptamers are easier to obtain and less expensive to produce because they are obtained in vitro in short time periods (days vs. months) and with limited cost. In addition, DNA/RNA aptamers can be denatured and renatured many times without losing their biorecognition ability. These unique properties make aptamers an idea platform for designing highly sensitive and selective biosensors (Hesselberth et al. 2000).

Radioisotope and fluorescence signals are often used to detect aptamer and aptazyme activity. Radioisotope-labeling has the advantage of minimal perturbation for the binding ability of aptamers and aptazymes (Rusconi et al. 2002, Seetharaman et al. 2001); however, safety and disposal concerns prevent this method from broad use. Fluorescence provides significant signal amplification and enables real-time monitoring of concentration fluctuations. However, determining effective parameters for using fluorophores is inefficient, requiring trial and error. If too close to the binding site, fluorophores may prevent the effector from binding; if too remote, no signal will be detected. To overcome this difficulty when using aptamers, fluorophores are incorporated into nucleotides during aptamer selection (Jhaveri et al. 2000). Many fluorophores are easily photo-bleached.

A powerful alternative to fluorophore and radio-isotope detection is colorimetry (Cao et al. 2001, Rakow and Suslick 2000, Smith et al. 1999). Colorimetric detection minimizes detection costs and safety concerns, and is well suited for on-site and real-time detection. In a colorimetric cocaine sensor based on aptamers, cocaine displaces a dye in the binding site of a cocaine aptamer (Stojanovic and Landry 2002). Because the dye has different absorption properties when bound to the aptamer, the presence of cocaine is indicated by a color change. However, finding an appropriate dye for a particular aptamer requires screening a large number of dyes. Moreover, the extinction coefficient for organic dyes seldom exceeds $10^6$ L·mole$^{-1}$·cm$^{-1}$, necessitating high dye concentration for simple visual observation.

Metallic particles have extinction coefficients three orders of magnitude higher than those of organic dyes (Link et al. 1999). For effective detection, they may be used in low concentrations (nanomolar) for use as detection agents with aptamers.

SUMMARY

In a first aspect, the invention is drawn to a sensor system for detecting an effector, having a nucleic acid enzyme (comprising an aptamer comprising a binding site for the effector), a substrate for the nucleic acid enzyme and particles having a second polynucleotide that is at least partially complementary to the substrate. The enzyme may be DNA, the effector may activate or inhibit the enzyme, the particles may be gold particles or other metal colloids or polystyrene latex particles. The effector may be adenosine, anthrax, an anthrax-derived molecule, small pox, a small pox-derived molecule, HIV, an HIV-derived molecule, an antiobiotic or cocaine. The nucleic acid enzyme may be both SEQ ID NOS:5 and 6, both SEQ ID NOS:8 and 9 or SEQ ID NO:1; the substrate may be SEQ ID NOS:4, 7 or 2. The sensor system may be mixed with a sample to detect an effector. Mg(II) and Pb(II) may also be added to the sample. When detecting an effector, a step of heating the sensor system to disrupt pairing between the polynucleotides may also be included. The presence of an effector is indicated by a color change in the sample, or of aggregated particles, which may precipitate in the sample.

In a second aspect, the invention is drawn to a sensor system for detecting an effector, having a nucleic acid enzyme of DNA (comprising an aptamer comprising a binding site for the effector), a substrate for the nucleic acid enzyme, gold particles having a second polynucleotide that is at least partially complementary to the substrate, and Mg(II).

The sensor system may further comprise Pb(II). This sensor system may be used to detect an effector by mixing it with a sample.

In a third aspect, the invention is drawn to methods of detecting an effector, where the ingredients of a sample, a nucleic acid enzyme (having an aptamer comprising a binding site for the effector), a substrate for the nucleic acid enzyme, and particles having a polynucleotide that is at least partially complementary to the substrate. The ingredients may be mixed in different sequences. The nucleic acid enzyme may be both SEQ ID NOS:5 and 6, both SEQ ID NOS:8 and 9 or SEQ ID NO:1; the substrate may be SEQ ID NOS:4, 7 or 2.

In a fourth aspect, the invention is drawn to kits for detecting an effector, a sensor system for detecting an effector, having a nucleic acid enzyme (comprising an aptamer comprising a binding site for the effector), a substrate for the nucleic acid enzyme and particles having a second polynucleotide that is at least partially complementary to the substrate. The particles may be gold particles or other metal colloids or polystyrene latex particles. The effector may be adenosine, anthrax, an anthrax-derived molecule, small pox, a small pox-derived molecule, HIV, an HIV-derived molecule, an antiobiotic or cocaine. The nucleic acid enzyme may be both SEQ ID NOS:5 and 6, both SEQ ID NOS:8 and 9 or SEQ ID NO:1; the substrate may be SEQ ID NOS:4, 7 or 2. The sensor system may be mixed with a sample to detect an effector. Mg(II) and Pb(II) may also be added to the sample. The presence of an effector is indicated by a color change in the sample, or of aggregated particles, which may precipitate in the sample.

The kit may be supplied such that the substrate, particles and nucleic acid enzyme are supplied in separate containers or the substrate, particles and nucleic acid enzyme are supplied in a single container. Furthermore, the kit may be supplied such that the substrate, particles and nucleic acid enzyme are supplied as an aggregate. The kit may further include control solutions, such as a solution having a known concentration of an effector. A color chart, wherein the colors indicate a concentration of the effector, may also be included to facilitate quantification.

DETAILED DESCRIPTION

Figure 1:
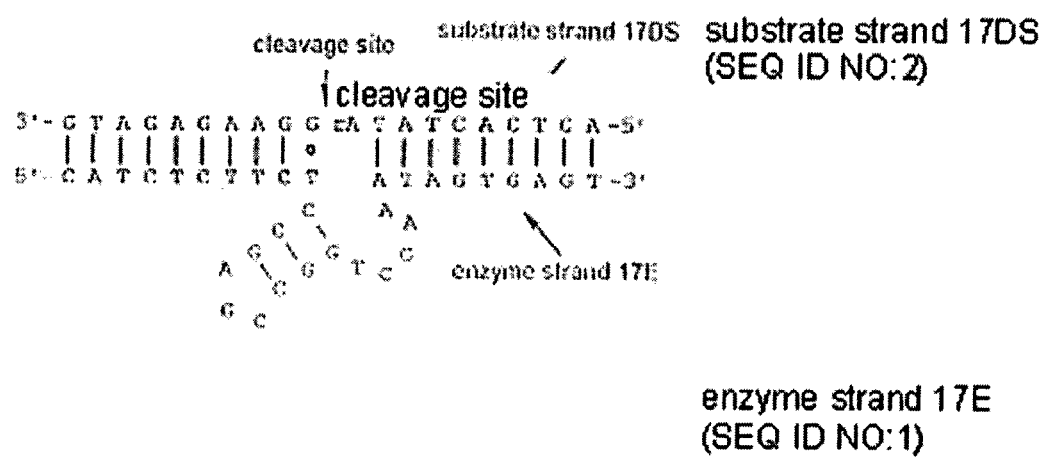
FIG. 1 shows an example of a nucleic acid enzyme and its substrate.

The present invention makes use of the discovery that the cleavage of a nucleic acid substrate by an aptazyme upon binding of an effector can be detected calorimetrically. In the presence of the effector, the substrate is cleaved and particles attached to polynucleotides that can hybridize to the substrate strand are dispersed, resulting in a color change. This system combines the benefit of elements that can recognize any molecule of choice with high sensitivity and ease-of-use provided by colorimetric detection.

The system comprises at least three parts:
(1) a nucleic acid-based enzyme having an effector-binding site (such as in aptamers) and a co-factor such as metal ions that catalyze substrate cleavage;
(2) a nucleic acid substrate for the nucleic acid-based enzyme, wherein interior portions of the substrate sequence is complementary to portions of the enzyme sequence; and
(3) particles attached to polynucleotides that are complementary to the 3'- and 5'-termini of the substrate.

To detect the target effector, the complementary portions of the polynucleotides (the polynucleotides attached to the particles complementary to the 3'- and 5'-termini of the substrate strand, and the 5'- and 3'-termini of the nucleic acid-based enzyme complementary to interior substrate strand sequences) are annealed in the presence of a sample suspected of containing the targeted effector. If the effector is absent, the aptazyme is either inactive or shows substantially reduced activity, resulting in no or little substrate cleavage and thus aggregation of the particles. If the effector is present, the enzyme is active and cleaves the substrate, preventing aggregate formation because the link between the particles is broken by the enzymatic cleavage step. In the case of gold particles, the aggregated state displays a blue color, while the dispersed state (or the non-aggregate state) is red in color. The presence of the target analyte as an effector can be detected based on the appearance of the color of the sensor system. More importantly, the concentration or the amount of the target analyte as an effector can be quantified by the degree of color deviation from blue or red. For example, a low concentration of the effector will result in a small percentage of substrate cleavage, small percentage of particles in the non-aggregate state, small deviation from the blue color and thus purple color can be observed. On the other hand, a high concentration of the effector will result in a large percentage of substrate cleavage, large percentage of particles in the non-aggregate state, large deviation from the blue color and thus pink/red can be observed. For a more quantitative analysis, spectrometry such as the extinction ratio between 522 nm and 700 nm can be used. The analyte as an effector may also decrease or inhibit the aptazyme activity instead of increase the aptazyme activity. In that case, the effect and color changes are the opposite to what described above. The effect may also be detected by other methods, such as aggregate precipitation. If the effector is absent, no cleavage will occur.

By replacing the aptamer domain with aptamers recognizing pre-selected effectors, calorimetric sensors for any desired effector can be easily made and used.

Definitions

An "effector" is a molecule that, when bound to an enzyme having an effector binding site, can enhance or inhibit enzyme catalysis. An "effector binding site" may be "specific," that is, binding only one effector molecule in the presence of other effector molecules. An example of effector binding site specificity is when only Zn(II) ions bind in the presence of many other ions, such as Mn(II), Mg(II) or Pb(II). Alternatively, an effector binding site may be "partially" specific (binding only a class of molecules), or "non-specific" (having molecular promiscuity). Examples of effectors include metal ions, anthrax, anthrax-derived molecules, small pox or small pox-derived molecules, pollutants (such as nitrogen fertilizers, toxic molecules, etc.), cocaine, human immuno-deficiency virus (HIV) and HIV-derived molecules.

A "nucleic acid-based enzyme" is an enzyme that principally contains nucleic acids, such as ribozymes (RNAzymes), deoxyribozymes (DNAzymes), and aptazymes. Nucleic acids may be natural, unnatural or modified nucleic acids. Peptide nucleic acids (PNAS) are also included. A nucleic acid-based enzyme requires a metal "co-factor" for efficient substrate cleavage and/or specific effector binding. Common co-factors include Mg(II) and Pb(II).

"Polynucleotide" refers to a nucleic acid sequence having at least two or more nucleotides. Polynucleotides may contain naturally-occurring nucleotides and modified nucleotides. PNA molecules are also embraced by this term.

"Sensitivity" refers to the limits of detection of a analytical device. In the context of the aptazyme-based sensors of the invention, sensitivity refers to the least concentration and highest concentration of an effector that the sensor can detect.

"Base-pairing" refers to the ability of a polynucleotide to form at least one hydrogen bond with a nucleotide under low stringency conditions. The nucleotide may be in a second polynucleotide or to a nucleotide found within the first polynucleotide. A polynucleotide is partially complementary to a second polynucleotide when the first polynucleotide is capable of forming at least one hydrogen bond with the second polynucleotide. To be partially complementary, a polynucleotide may have regions wherein base pairs may not form surrounded by those regions that do, form loops, stem-loops, and other secondary structures.

A Nucleic Acid-based Enzyme Having an Effector (or Effectors) Binding Site

A number of nucleic acid enzymes have been discovered or developed, having diverse catalytic activities (Tables 1 and 2). For catalytic function, the enzymes usually depend on one or more ion co-factors. In vitro selection may be used to "enhance" selectivity and sensitivity for a particular ion. Nucleic acid enzymes that catalyze molecular association (ligation, phosphorylation, and amide bond formation) or dissociation (cleavage or transfer) are particularly useful for the methods and compositions of the invention.

A nucleic acid enzyme that catalyzes the cleavage of a nucleic acid in the presence of an effector is used. The nucleic acid enzyme may be RNA (ribozyme), DNA (deoxyribozyme), a DNA/RNA hybrid enzyme, or a peptide nucleic acid (PNA) enzyme. PNAs comprise a polyamide backbone and naturally-occurring nucleoside bases (available from, e.g., Biosearch, Inc. (Bedford, Mass.)). Ribozymes that may be used include group I and group II introns, the RNA component of the bacterial ribonuclease P, hammerhead, hairpin, hepatitis delta virus and *Neurospora* VS ribozymes. Also included are in vitro selected ribozymes, such as those previously isolated (Tang and Breaker 2000). Ribozymes tend to be less stable than deoxyribozymes; thus deoxyribozyme are preferred. Deoxyribozymes with extended chemical functionality are also desirable (Santoro et al., 2000).

TABLE 1

Reactions catalyzed by ribozymes that were isolated from in vitro selection experiments.

| Reaction | $k_{cat}$ (min$^{-1}$) | $K_m$ (μM) | $k_{cat}/k_{uncat}$[a] | Reference |
|---|---|---|---|---|
| Phosphoester centers | | | | |
| Cleavage | 0.1 | 0.03 | $10^5$ | (Vaish et al. 1998) |
| Transfer | 0.3 | 0.02 | $10^{13}$ | (Tsang and Joyce 1996) |
| Ligation | 100 | 9 | $10^9$ | (Ekland et al. 1995) |
| Phosphorylation | 0.3 | 40 | $>10^5$ | (Lorsch and Szostak 1994) |
| Mononucleotide polymerization | 0.3 | 5000 | $>10^7$ | (Ekland and Bartel 1996) |
| Carbon centers | | | | |
| Aminoacylation | 1 | 9000 | $10^6$ | (Illangasekare and Yarus 1997) |
| Aminoacyl ester hydrolysis | 0.02 | 0.5 | 10 | (Piccirilli et al. 1992) |
| Aminoacyl transfer | 0.2 | 0.05 | $10^3$ | (Lohse and Szostak 1996) |
| N-alkylation | 0.6 | 1000 | $10^7$ | (Wilson and Szostak 1995) |
| S-alkylation | $4 \times 10^3$ | 370 | $10^3$ | (Wecker et al. 1996) |
| Amide bond cleavage | $1 \times 10^5$ | | $10^2$ | (Dai et al. 1995) |
| Amide bond formation | 0.04 | 2 | $10^5$ | (Wiegand et al. 1997) |
| Peptide bond formation | 0.05 | 200 | $10^6$ | (Zhang and Cech 1997) |
| Diels-Alder cycloaddition | $>0.1$ | $>500$ | $10^3$ | (Tarasow et al. 1997) |
| Others | | | | |
| Biphenyl isomerization | $3 \times 10^5$ | 500 | $10^2$ | (Prudent et al. 1994) |
| Porphyrin metallation | 0.9 | 10 | $10^3$ | (Conn et al. 1996) |

[a]Reactions catalyzed by ribozymes that were isolated from in vitro selection experiments. $k_{cat}/k_{uncat}$ is the rate enhancement over uncatalyzed reaction.

TABLE 2

Deoxyribozymes isolated through in vitro selection.

| Reaction | Cofactor | $k_{max}(\text{min}^{-1})^b$ | $k_{cat}/k_{uncat}$ | Reference |
|---|---|---|---|---|
| RNA transesterification | $Pb^{2+}$ | 1 | $10^5$ | (Breaker and Joyce 1994) |
|  | $Mg^{2+}$ | 0.01 | $10^5$ | (Breaker et al. 1995) |
|  | $Ca^{2+}$ | 0.08 | $10^5$ | (Faulhammer and Famulok 1997) |
|  | $Mg^{2+}$ | 10 | $>10^5$ | (Santoro and Joyce 1997) |
|  | None | 0.01 | $10^8$ | (Geyer and Sen 1997) |
|  | L-histidine | 0.2 | $10^6$ | (Roth and Breaker 1998) |
|  | $Zn^{2+}$ | ~40 | $>10^5$ | (Li et al. 2000) |
| DNA cleavage | $Cu^{2+}$ | 0.2 | $>10^6$ | (Carmi et al. 1996) |
| DNA ligation | $Cu^{2+}$ or $Zn^{2+}$ | 0.07 | $10^5$ | (Cuenoud and Szostak 1995) |
| DNA phosphorylation | $Ca^{2+}$ | 0.01 | $10^9$ | (Li and Breaker 1999) |
| 5',5'-pyrophophate formation | $Cu^{2+}$ | $5 \times 10^{\square}$ | $>10^{10}$ | (Li et al. 2000) |
| Porphyrin metalation | None | 1.3 | $10^3$ | (Li and Sen 1996) |

$^b k_{max}$ is the maximal rate constant obtained under optimized conditions.

Methods of producing ribozymes and deoxyribozymes include chemical oligonucleotide synthesis, polymerase chain reaction (PCR), DNA cloning and replication, or any other methods in the art. Preferably the nucleic acid enzymes are DNA/RNA hybrids and PNAs. Nucleotides containing modified bases, phosphates, or sugars may also be used; in some instances, these modified nucleotides may be advantageous for stability or confer effector specificity. Examples of modified bases include inosine, nebularine, 2-aminopurine riboside, $N^7$-deazaadenosine, and $O^6$-methylguanosine (Earnshaw and Gait 1998). Modified sugars and phosphates include 2'-deoxynucleoside, abasic, propyl, phosphorothioate, and 2'-O-allyl nucleoside (Earnshaw and Gait 1998).

A nucleic acid enzyme that cleaves a nucleic acid strand separate from the strand comprising the enzyme is a trans-acting enzyme. Using trans-acting enzymes allows for multiple rounds of substrate cleavages, since the enzymatic product is removed. An example of such a nucleic acid enzyme is 17E (SEQ ID NO:1); the corresponding substrate is 17DS (SEQ ID NO:2; r denotes a single ribonucleotide); both are presented in Table 3A and illustrated in FIG. 1. Other examples are also given in Table 3B.

TABLE 3A

DNA enzymes and substrates

| Molecule | SEQ ID NO: | Sequence$^c$ | # of nucleotides |
|---|---|---|---|
| Enzyme (17E) | 1 | catctcttct ccgagccggt cgaaatagtg agt | 33 |
| Substrate for 17E (17DS) | 2 | actcactatr ggaagagatg | 21 |
| Enzyme: JLYL1 "8–17" half | 5 | tctcttctcc gagccggtcg aaatattgga ggaagctc | 38 |
| ATP half | 6 | gagctggagg aaaaagtgag tc | 22 |
| Sustrate for JLYL1 | 4 | gactcactat rggaagaga | 19 |
| Enzyme: JLYL2 "8–17" half | 8 | tctcttct ccgagccggt cgaaatattg gaggaagctc gagctggagg aaaaagtgag tc | 38 |
| ATP half | 9 |  | 22 |
| Substrate for JLYL2 | 7 | actcatctgt gagactcact atrggaagag atgtcaactc gtg | 43 |

$^c$ "r" denotes a single ribonucleotide, such as adenosine ribonucleotide

TABLE 3B

RNA/DNA based aptamers and RNA/DNAzymes

| RNA/DNA based aptamers and their targets[1–4] | | RNA/DNAzymes[5,6–10] |
|---|---|---|
| Organic dyes[11,12] | Xanthene[59] | 8-17 DNAzyme[13–15] |
| Theophyllin[16] | Kanamycin A[60] | 10-23 DNAzymes[13,17] |
| Dopamine[18] | Lividomycin[60] | Hammerhead[19,20] |
| Hoechst 33258[21] | Tobramycin[61] | Hairpin[19,22] |
| Sulforhodamine B[23,24] | Neomycin B[62,63] | Leadzyme[25] |

TABLE 3B-continued

RNA/DNA based aptamers and RNA/DNAzymes

| RNA/DNA based aptamers and their targets[1–4] | | RNA/DNAzymes[5],[6–10] |
|---|---|---|
| Cellobiose[26] | Viomycin[64] | Hepatitis Delta Virus[27,28] |
| D-tryptophan[29] | Chloramphenicol[65] | Group I Intron[30,31] |
| L-arginine[32–37] | Streptomycin[66] | Spliceosome[38] |
| L-citrullin[32,36] | HIV-1 Rev peptide[67,68] | Ribosome[39] |
| L-argininamide[40] | Vasopressin[69] | DNA nuclease activity[41] |
| L-valine[42] | Spectinomycin[70] | Ligase activity[43] |
| L-isoleucine[44] | L-tyrosinamide[71] | Kinase activity[45] |
| AMP/ATP[46–50] | HIV-1 RNase H[72] | Phosphoramidate bond cleavage[51] |
| Guanosine[52] | Chitin[73] | Porphyrin metallation[53] |
| FMN[47,54] | Human Thrombin[74] | Peroxidase activity[55] |
| NAD[54] | cAMP[75] | |
| Vitamin $B_{12}$[56] | Cholic acid[76] | |
| 8-oxo-dG[57] | Hematoporphyrin[77] | |
| 5'-cap[58] | HIV-1 Tat/$Zn^{2+}$[78] | |
| | Anthrax spores[79] | |

Directed mutagenesis can be used to change one or more properties of a nucleic acid enzyme or its substrate. Using 17E and 17DS as an example, one may wish to alter the avidity of the two arms of the hybridized enzyme and substrate. The "arms" are those areas displaying Watson-Crick base-pairing in FIG. 1. To alter avidity, the length of the arms is changed. Increasing the length of the arms increases the number of Watson-Crick bonds, thus increasing avidity; decreasing the length decreases avidity. Decreasing the avidity of the arms facilitates the removal of substrate from the enzyme, thus allowing for faster enzymatic turnover.

Another method of decreasing avidity includes creating mismatches between the enzyme and the substrate. Alternatively, the G-C content of the arms may be altered. The effect of any directed change should be monitored to ensure that the enzyme retains the desired activity, including ion sensitivity and selectivity. For example, to ensure that the mutated enzyme maintains sensitivity and selectivity for adenosine, one would test to determine if the mutated enzyme remained reactive in the presence of adenosine (sensitivity) and maintained its lower level of activity in the presence of other effectors (selectivity).

In vitro Selection of Aptamers

Aptamers and aptazymes that bind a desired effector can be isolated by in vitro selection. In vitro selection is a technique in which RNA or DNA molecules with certain functions are isolated from a large number of sequence variants through multiple cycles of selection and amplification (Chapman and Szostak 1994, Joyce 1994). DNAzymes and RNAzymes with maximized activities or novel catalytic abilities, as well as aptamers can be obtained using, for example, the technique of systematic evolution of ligands by exponential enrichment (SELEX) (Tuerk and Gold 1990).

In vitro selection is typically initiated with a large collection (pool) of randomized sequences, usually containing $10^{13}$-$10^{15}$ sequence variants. Chemical synthesis of a set of degenerated polynucleotides using standard phosphoramidite chemistry can be used to generate such randomized pools. The 3'-phosphoramidite compounds of the four nucleosides (adenosine, cytosine, guanine, thymidine) are premixed and used to synthesize the polynucleotides; randomness is generated by controlling the ratio of the four phosphoroamidites. Biases can also be achieved, as well as holding a phosphoramidite constant at a specific position. Other strategies for creating randomized DNA libraries include mutagenic polymerase chain reaction (PCR) and template-directed mutagenesis (Cadwell and Joyce 1992, Cadwell and Joyce 1994, Tsang and Joyce 1996). If in vitro selection of RNA molecules is desired, randomized DNA libraries are first converted to an RNA library by in vitro transcription.

The randomized libraries are then screened for molecules possessing a desired function, such as binding the targeted effector, and are isolated. Separation may be achieved using affinity column chromatography (using, e.g., the targeted effector), gel electrophoresis, or selective amplification of a tagged reaction intermediate. The selected molecules are amplified, using, for example, PCR for DNA, or isothermal amplification reaction for RNA. These selected, amplified molecules are then mutated (reintroducing diversity) using, for example, mutagenic PCR to attempt to select for molecules with yet higher activity. These three steps, selection, amplification and mutation, are repeated, often with increasing selection stringency, until sequences with the desired activity dominate the pool.

Novel nucleic acid enzymes isolated from random sequences in vitro have extended the catalytic repertoire of RNA and DNA (Table 1). Deoxyribozymes catalyze fewer types of reactions compared to ribozymes (Table 2). The catalytic rate ($k_{cat}$) of most deoxyribozymes is comparable to that of ribozymes catalyzing the same reaction. In certain cases, the catalytic efficiency ($k_{cat}/K_m$) of nucleic acid enzymes even exceeds protein enzyme catalytic efficiency.

In vitro selection can be used to change the ion specificity or binding affinity of existing nucleic acid enzymes, or to obtain nucleic acid enzymes specific for desired substrates. For example, the $Mg^{2+}$ concentration required for optimal hammerhead ribozyme activity has been lowered using in vitro selection to improve the enzyme performance under physiological conditions (Conaty et al. 1999, Zillmann et al. 1997).

Often nucleic acid enzymes developed for a specific effector by in vitro selection will have activity in the presence of other molecules. For example, 17E deoxyribozyme was developed by in vitro selection for activity in the presence of $Zn^{2+}$. However, the enzyme showed greater activity in the presence of $Pb^{2+}$ than $Zn^{2+}$. Although produced in a process looking for $Zn^{2+}$-related activity, 17E may be used as a sensitive and selective sensor for $Pb^{2+}$. To produce nucleic acid enzymes with greater selectivity, a negative selection step may be introduced.

Other polynucleotide sequences are useful, including those described in U.S patent application Ser. No. 09/605,558, filed Jun. 27, 2000, now U.S. Pat. No. 6,706,474, issued Mar. 16, 2004, the contents of which are incorporated by reference (Lu and Liu).

Aptazyme Structure

The aptazyme (FIG. 2) consists of a sequence complementary to a region 3' of the cleavage site of the substrate, a DNAzyme catalytic core that is conserved, a variable region that is attached to the 3' terminus of the core (tatt (SEQ ID NO:3, indicated by "*" in FIG. 2), the effector binding site (FIG. 2, "aptamer motif"), and a 3' sequence that is complementary to a region 5' of the substrate cleavage site. The variable region may be 1, 2, 3, 4, 5, 6, 7, 8, 9, 10 or more nucleotides longer; preferably 3-6 nucleotides long. By varying the length of the variable region, enzymatic activity and/or effector binding (selectivity and/or avidity) may be improved.

Figure 2:
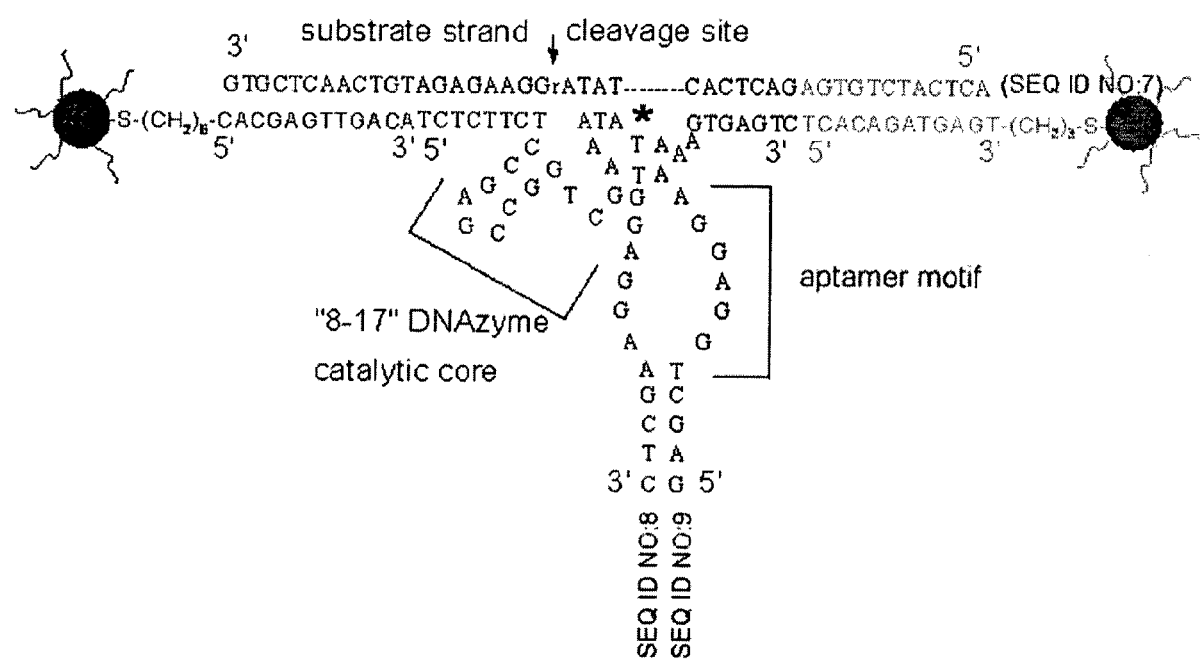
FIG. 2 shows an adenosine aptazyme (SEQ ID NOS: 8 and 9); a substrate (SEQ ID NO:7), where rA indicates a single adenosine ribonucleotide; a polynucleotide having complementarity to the 3'-portion of the substrate and conjugated to a particle (SEQ ID NO:10); and a polynucleotide having complementarity to the 5'-portion of the substrate and conjugated to a particle (SEQ ID NO:11).

The aptazyme shown in FIG. 2 is specific for adenosine. The nucleotide sequence for the DNAzyme is SEQ ID NO:8, the sequence for the polynucleotide containing that aptamer is SEQ ID NO:9, and the nucleotide sequence for the substrate strand is SEQ ID NO:7.

Particles Tagged with Polynucleotides Complementary to the 3' and 5' Termini of the Nucleic Acid Enzyme Substrate For the sensor to register the enzymatic activity, a detectable change must occur upon a change in aggregation of the particles to which the polynucleotides are attached. In addition, the composition of the particles must be such that they do not interfere with substrate cleavage. Particles may be made of metal, semiconductor and magnetic colloids; ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs (e.g., (Mirkin et al. 2002)); and gold particles (commercially available; e.g., Amersham Biosciences; Piscataway, N.J. and Nanoprobes, Inc; Yaphank, N.Y.). Non-metal particles may also be used, such as polystyrene latex particles or latex particles containing dye.

Gold colloidal particles are preferred. Gold colloidal particles have high extinction coefficients for the bands that give rise to their intense colors. These colors vary with particle size, concentration, inter-particle distance, extent of aggregation and shape of the aggregates. For instance, hybridization of polynucleotides attached to gold particles results in an immediate color change visible to the naked eye (see, e.g., (Mirkin et al. 2002)).

Gold particles, polynucleotides or both are derivatized for the attachment of polynucleotides. For instance, polynucleotides derivatized with alkanethiols at their 3'- or 5'-termini readily attach to gold particles (Whitesides 1995). A method of attaching 3' thiol DNA to flat gold surfaces can also be used to attach polynucleotides to particles (Mucic et al. 1996). Alkanethiol-derivatized particles can be used to attach polynucleotides. Other functional groups for attaching polynucleotides to solid surfaces include phosphorothioates to attach polynucleotides to gold surfaces (Beebe and Rabke-Clemmer 1995), substituted alkylsiloxanes for binding polynucleotides to silica and glass surfaces and aminoalkylsiloxanes and mercaptoaklylsiloxanes (Grabar et al. 1995). Polynucleotides terminating in a 5'-thionucleoside or a 3'-thionucleoside may also be used for attaching polynucleotides to solid surfaces. Some methods of attaching polynucleotides are presented in Table 4.

TABLE 4

Systems for attaching polynucleotides to particles

| System | Reference |
| --- | --- |
| biotin-streptavidin | (Shaiu et al. 1993) |
| carboxylic acids on aluminum | (Allara and Nuzzo 1985) |
| disulfides on gold | (Nuzzo et al. 1987) |
| carboxylic acids on silica | (Iler 1979, Tompkins and Allara 1974) |
| carboxylic acids on platinum | (Timmons and Zisman 1965) |
| aromatic ring compounds on platinum | (Soriaga and Hubbard 1982) |
| silanes on silica | (Maoz and Sagiv 1987) |

Preferably, the substrate is modified, for example, by extension of the 3'- and 5'-ends by a number of bases which act as "sticky ends" for facilitating annealing to the complementary polynucleotide strand attached to the particles. Substrate modification allows complexes comprising substrate-linked particles to be formed without inhibiting the nucleic acid enzyme/substrate interaction. However, where the substrate contains regions not critical for interaction with the nucleic acid enzyme, modification may not be necessary.

Figure 3:
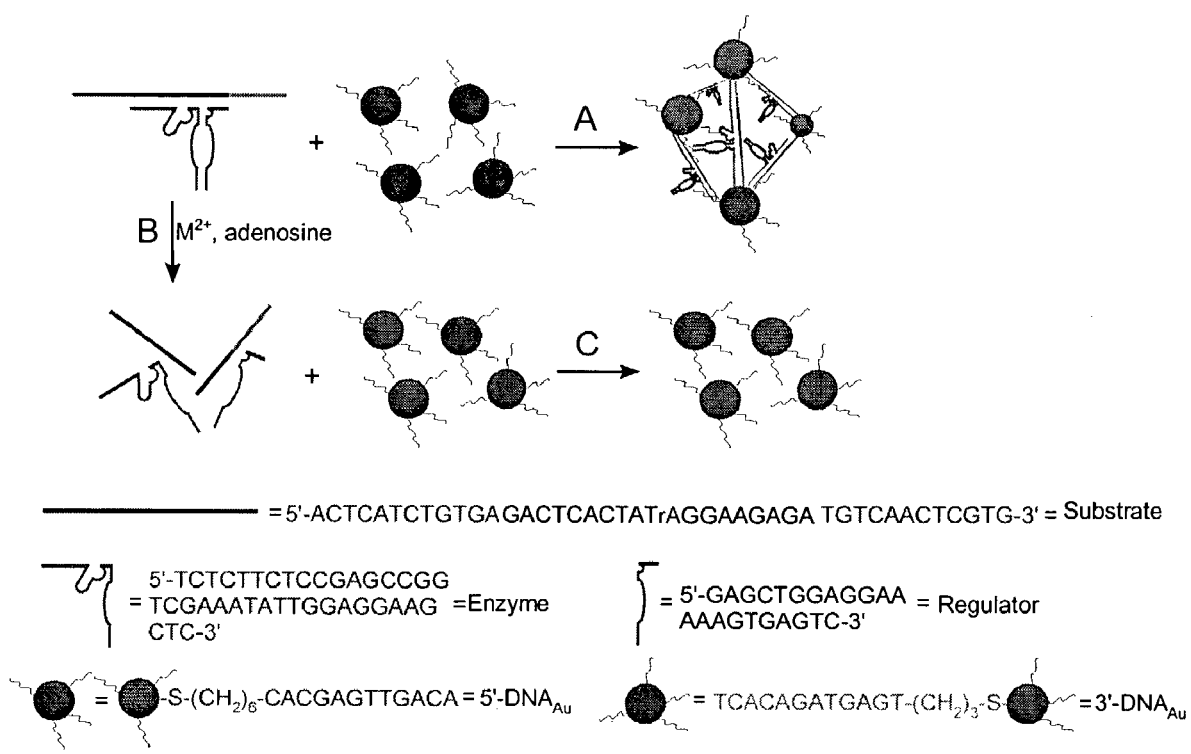
FIG. 3 shows a schematic representation of the colorimetric detection of adenosine. The aptazyme system can act as linker for DNA attached gold particles to form aggregations, which have a blue color (reaction A). In the presence of adenosine and metal ions, the substrate can be cleaved (reaction B). The cleaved substrate can no longer act as linker for particles and the color remains red (reaction C). The polynucleotide containing the substrate (SEQ ID NO:7), the polynucleotide containing the enzyme (SEQ ID NO:5), the polynucleotide containing the regulator (SEQ ID NO:6), the polynucleotide having complementarity to the 3'-portion of the substrate and conjugated to a particle (SEQ ID NO:10) and the polynucleotide having complementarity to the 5'-portion of the substrate and conjugated to a particle (SEQ ID NO:11) are illustrated.

To detect the target effector, the nucleic acid enzyme, substrate, and labeled particles are combined in the presence of a sample suspected of containing a target effector, such as adenosine, to which the enzyme is sensitive (FIG. 3). In the presence of the effector, the enzyme cleaves the substrate, preventing aggregate formation. In some instances, heating the sensor system to above the melting point of the complex may be necessary. In this case, the presence of the effector allows the enzyme to cleave the substrate, preventing aggregation of the complex.

Different aggregation states of the particles results in a different color. For example, a large degree of particle aggregation display colors close to blue while a small degree of particle aggregation display colors close to red. Furthermore, the amount of substrate cleavage and thus the degree of aggregation depends on the concentration of the effector. A low effector concentration results in only partial substrate cleavage that produces a mixture of single particles and aggregates, allowing for semi-quantitatively or qualitative assays. The color difference can be amplified to improve sensitivity. For a quantitative measurement, the optical spectra of the assay mixture are determined. In addition to color change, the formation of aggregates of the particles, or precipitation of aggregated particles may also be monitored. Color changes can be observed with the naked eye or spectroscopically. The formation of aggregates can be observed by electron microscopy or by nephelometry; and precipitation of aggregated particles can be observed with the naked eye or microscopically.

To facilitate the observation of a color change, the color is observed on a background of a contrasting color. When gold particles are used, the observation of a color change is facilitated by spotting a sample of the hybridization solution on a solid white surface (such as silica or alumina TLC plates, filter paper, cellulose nitrate membranes, and nylon membranes) and allowing the spot to dry. Initially, the spot retains the color of the hybridization solution (which ranges from pink/red, in the absence of aggregation, to purplish-red/purple, if there has been aggregation of gold particles). On drying, a blue spot develops if aggregation is present prior to spotting; a pink spot develops if dispersion occurred. The blue and the pink spots are stable and do not change on subsequent cooling or heating or over time. They provide a convenient permanent record of the test. No other steps are necessary to observe the color change.

Alternatively, assay results may be visualized by spotting a sample onto a glass fiber filter (e.g., Borosilicate Microfiber Filter, 0.7 μm pore size, grade FG75) for use with 13 nm gold particles. After rinsing with water, a spot comprising the aggregates is observed. Additional methods are also available for visualizing assay results (Mirkin et al. 2002).

The targeted effector can be detected in a variety or samples, including bodily fluids. Standards containing known amounts of the effector may be assayed along side the unknown sample, and the color changes compared. Alternatively, standard color charts, similar to those used with pH papers, may be provided.

Kits

The invention also provides kits for detecting analytes as effectors. In one embodiment, the kit comprises at least one container, the container holding at least one type of particle having polynucleotides attached thereto; a substrate; and a nucleic acid enzyme. The polynucleotides attached to the particles have a sequence complementary to the sequence of at least a first and a second portion of the substrate. The first and second portions of the substrate are separated by a third portion of the substrate that is cleaved by the nucleic acid enzyme in the presence of the analyte.

A kit may also comprise at least two types of particles having polynucleotides attached thereto. A first type of particle has attached polynucleotides which have a sequence complementary to the sequence of a first portion of the substrate. A second type of particle has polynucleotides attached that have a sequence complementary to the sequence of a second portion of the substrate. The first and second portions of the substrate are separated by a third portion of the substrate that is cleaved by the nucleic acid enzyme in the presence of the effector.

When a kit is supplied, the different components of the composition may be packaged in separate containers and admixed immediately before use. Such packaging of the components separately may permit long-term storage of the active components. For example, one or more of the particles having polynucleotides attached thereto; the substrate; and the nucleic acid enzyme are supplied in separate containers.

The reagents included in the kits can be supplied in containers of any sort such that the life of the different components are preserved and are not adsorbed or altered by the materials of the container. For example, sealed glass ampules may contain one of more of the reagents, or buffers that have been packaged under a neutral, non-reacting gas, such as nitrogen. Ampules may consist of any suitable material, such as glass, organic polymers, such as polycarbonate, polystyrene, etc.; ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

The kits may also contain other reagents and items useful for detecting the targeted effector. The reagents may include standard solutions containing known quantities of the effector, dilution and other buffers, pretreatment reagents, etc. Other items which may be provided as part include a backing (for visualizing aggregate break down), such as a TLC silica plate; microporous materials, syringes, pipettes, cuvettes and containers. Standard charts indicating the appearance of the particles in various aggregation states, corresponding to the presence of different amounts of the effector under test, may be provided.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

EXAMPLES

The following examples are provided to illustrate the invention. Those skilled in the art can readily make insignificant variations in the compositions and methods of this invention. The examples are not meant to limit the invention in any way.

An aptazyme designed for the directed assembly of gold particles for colorimetric detection and quantification of adenosine is herein used as a paradigm. By replacing the aptamer domain that recognizes adenosine in the exemplary adenosine biosensor with other aptamer domains recognizing pre-selected effectors, calorimetric sensors for any desired effector can be easily made and used. Furthermore, by replacing the catalytic core (the 8-17 motif in this case) with other catalytic cores, similar aptazymes may be engineered.

Example 1

Colorimetric Adenosine Biosensor

Polynucleotides and Reagents

All polynucleotides were purchased from the Integrated DNA Technology Inc. (Coralville, Iowa). Adenosine and other nucleosides were purchased from Sigma-Aldrich (St. Louis, Mo.). Thirteen nm diameter gold particles were prepared and 3'- and 5'-thiol-modified 12-mer DNA were attached (Storhoff et al. 1998).

Cleavage Reaction

Thirty-eight μl of solution containing 3 μM substrate, 6 μM enzyme and 9 μM regulator strands in 300 mM NaCl, 50 mM Tris-actate, pH 7.2 buffer (300 mM NTA). 2 μl metal ion stock solution (5 mM Pb(II) and 200 mM Mg(II)) were added to initiate the cleavage reaction. The final metal ion concentration was 0.25 mM Pb(II) and 10 mM Mg(II). At different times, 2 μl aliquots were transferred to tube containing of 50 μl gold particles with 10 μM EDTA; the EDTA specifically chelated Pb(II) (5 μM) in solution, even in the presence of 0.4 mM Mg(II), because the formation constant of EDTA for Pb(II) is approximately 10 orders of magnitude higher than that for Mg(II) (Sillén 1964). In the presence of 0.4 mM Mg(II) only, the cleavage rate for the aptazyme is negligible. Thus, the reaction can be considered quenched upon transferring to the gold particle solution. The 2 μl aliquot contained 6 pmol substrate if no cleavage occurs. The cleavage can decrease the amount of substrate and that can be reflected by the degree of aggregation of the particles.

Gold Particle Aggregation

The particle solution mixed with a 2 µl aliquot was heated to ~70° C. for 3 minutes and then was allowed to cool to room temperature. The solution was assayed for the extinction property using UV-vis extinction spectroscopy or spotted onto a TLC plate.

FIG. 2 shows the primary and proposed secondary structure of the three nucleic acid strands that comprise the adenosine aptazyme and two DNA-attached gold particles hybridized with the substrate strand. The two particles are designed to be positioned at the two ends of the substrate, so that two different thio-modified DNA molecules are used to attach to gold particles. One sequence has a thiol group at the 3' end of the DNA (3'-$DNA_{Au}$) and the other has a thiol at the 5' end (5'-$DNA_{Au}$). The substrate strand is a DNA/RNA chimera with a single RNA linkage that serves as the cleavage site. The strand is flanked with two 12-mer overhang that are used to hybridize with 3'-$DNA_{Au}$ and 5'-$DNA_{Au}$. The catalytic core of the aptazyme is adapted from the "8-17" DNAzyme (Faulhammer and Famulok 1997, Li et al. 2000, Santoro and Joyce 1997) and has been optimized for high activity in the presence of Pb(II) (Brown et al., Li et al. 2000). The 3' end of the DNAzyme is hybridized with the third component of the aptazyme to form an adenosine aptamer motif, obtained using SELEX process (Huizenga and Szostak 1995) and was adapted into an aptazyme (Wang et al. 2002). The presence of adenosine promotes formation of the active tertiary DNAzyme structure. This complex then promotes cleavage of the substrate strand at the single ribo-adenosine position. Without adenosine, even though the three components may interact via Watson-Crick base-paring, the catalytic activity is much less than that in the presence of adenosine (Wang et al. 2002).

FIG. 3 shows a schematic of the colorimetric detection of adenosine based on aptazyme-directed assembly of gold particles. In the absence of adenosine, the substrate strand in this aptazyme can be used as a linker to bring DNA modified gold particles together through hybridization to the DNA-tagged particles (reaction A). Since the color of the gold particles changes from red for separated particles to blue for aggregated particles (Mirkin et al. 1996), upon hybridization, a blue color is observed. However, the presence of adenosine can switch on the aptazyme activity for cleaving the substrate strand (reaction B). The cleaved substrate can no longer support the gold particle aggregates. Thus the red color of separated particles is observed (reaction C). Because the rate of substrate cleavage can be modulated by the concentration of adenosine that binds to the aptamer motif, the fraction of cleavage at a set time should be dependent on the concentration of adenosine. Different ratios of the cleaved to non-cleaved substrates results in different colors, from red to blue, which reflect the adenosine concentration and can be quantified.

Example 2

Demonstration of Aptazyme-directed Assembly of Gold Particles

Figure 4:
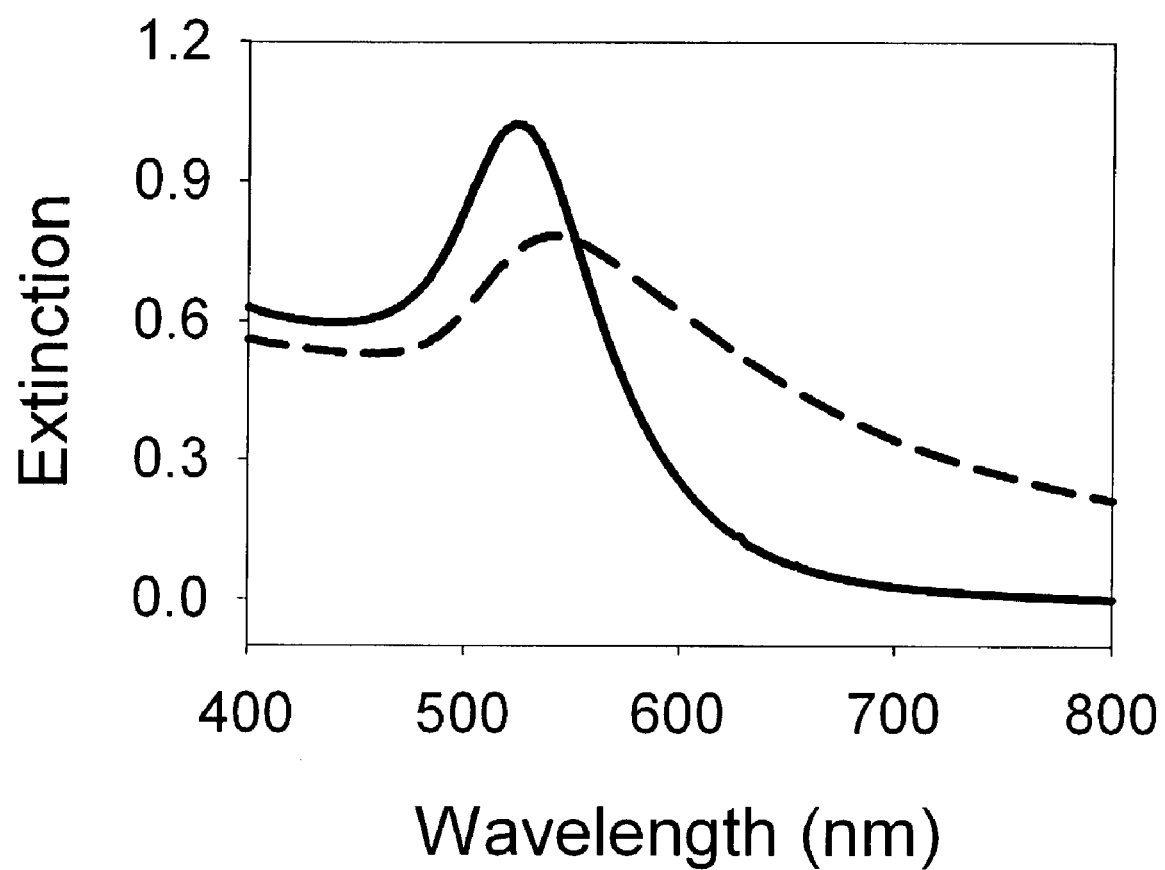
FIG. 4 shows the extinction spectra of separated 13 nm diameter gold particles (solid line) and gold particles aggregation linked by aptazymes (dashed line) in the visible region. Aggregation induced by DNA linkers shifts the peak of the surface plasmon band from 522 nm to 540 nm.
Figure 5:
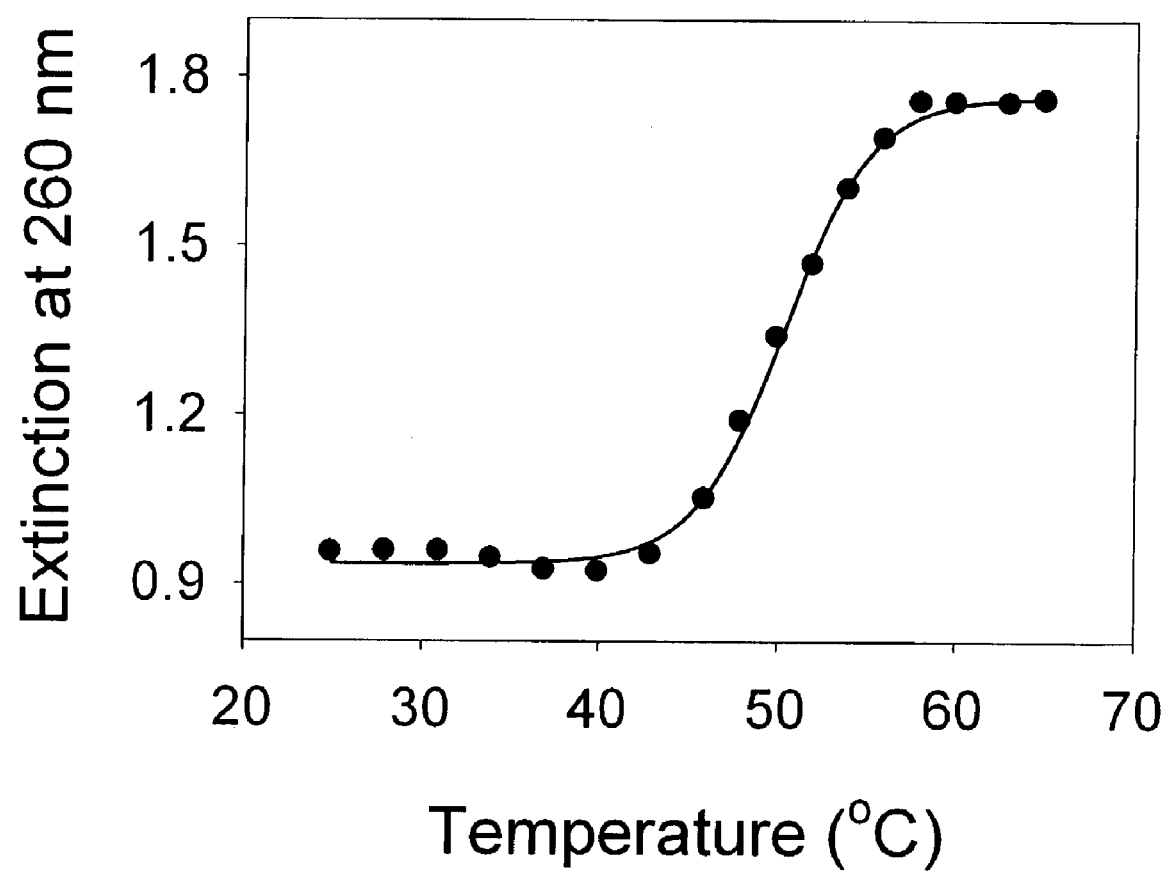
FIG. 5 shows the melting curve of the aptazyme assembled gold particles in 25 mM Tris-acetate buffer, pH 7.2, 300 mM NaCl.

FIG. 4 shows the extinction spectra of gold particles in the absence (solid line) and in the presence (dash line) of the substrate strand. The shift of the extinction peak from 522 nm to 540 nm and the significant increase in extinction in the long wavelength region indicate that the presence of the substrate strand converts separated gold particles (red) to aggregated particles (blue). The melting temperature of the aggregate was determined to be 50° C. in 300 mM NaCl (FIG. 5). The sharp melting transition demonstrates the formation of DNA linked gold particle assembly.

Figure 6:
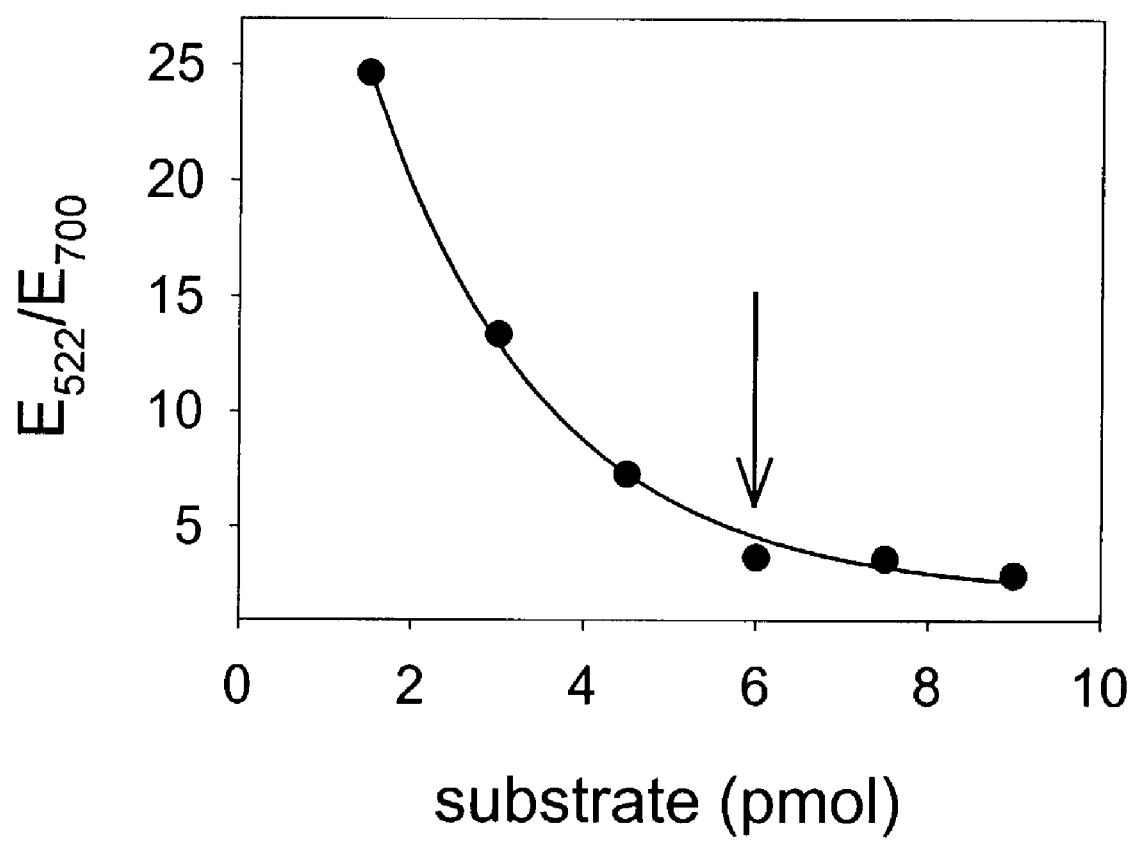
FIG. 6 shows the relationship between the substrate quantity and the degree of aggregation of gold particles. The vertical axis is the ratio of the extinction between 522 nm and 700 nm. The arrow indicates 6 pmol of substrate.

Determining the optimal ratio between the substrate strand and particles, such that any decrease in the quantity of substrate induced by cleavage can be reflected in the optical properties of the particle aggregations, increases sensitivity of the assay. If the substrate is in excess, a small fraction of cleavage will be undetected. To a mixture of equal volumes (25 µl) of 5'-$DNA_{Au}$ and 3'-$DNA_{Au}$, each with extinction of 2.2 at 522 nm, 1 to 9 pmol of substrate was added in the presence of excess amount of the enzyme and the regulator strands. After annealing, the extinction properties of the resulting solutions were determined by UV-vis spectroscopy. The extinction ratio between 522 nm and 700 nm was used to assay the degree of aggregation. These two wavelengths were chosen to represent the quantity of separated and aggregated particles, respectively (FIG. 6). A lower ratio indicates a higher degree of aggregation. This ratio is also a measure of the color changes from red to blue. A high ratio is indicated by red and a low ratio is indicated by blue. The ratio decreases exponentially with increasing quantity of the substrate strand, showing that the addition of substrate increases particle aggregations. When the substrate is more than 6 pmol, the degree of aggregation is no longer sensitive to a further increase in the substrate quantity. Therefore, 6 pmol of substrate are used as a starting point for forming aggregation. Any cleavage of the substrate disturbs the formation of aggregates and increases the extinction ratio.

Example 3

The Kinetics of Color Changes of the Aptazyme-gold Particle Sensor

Figure 7:
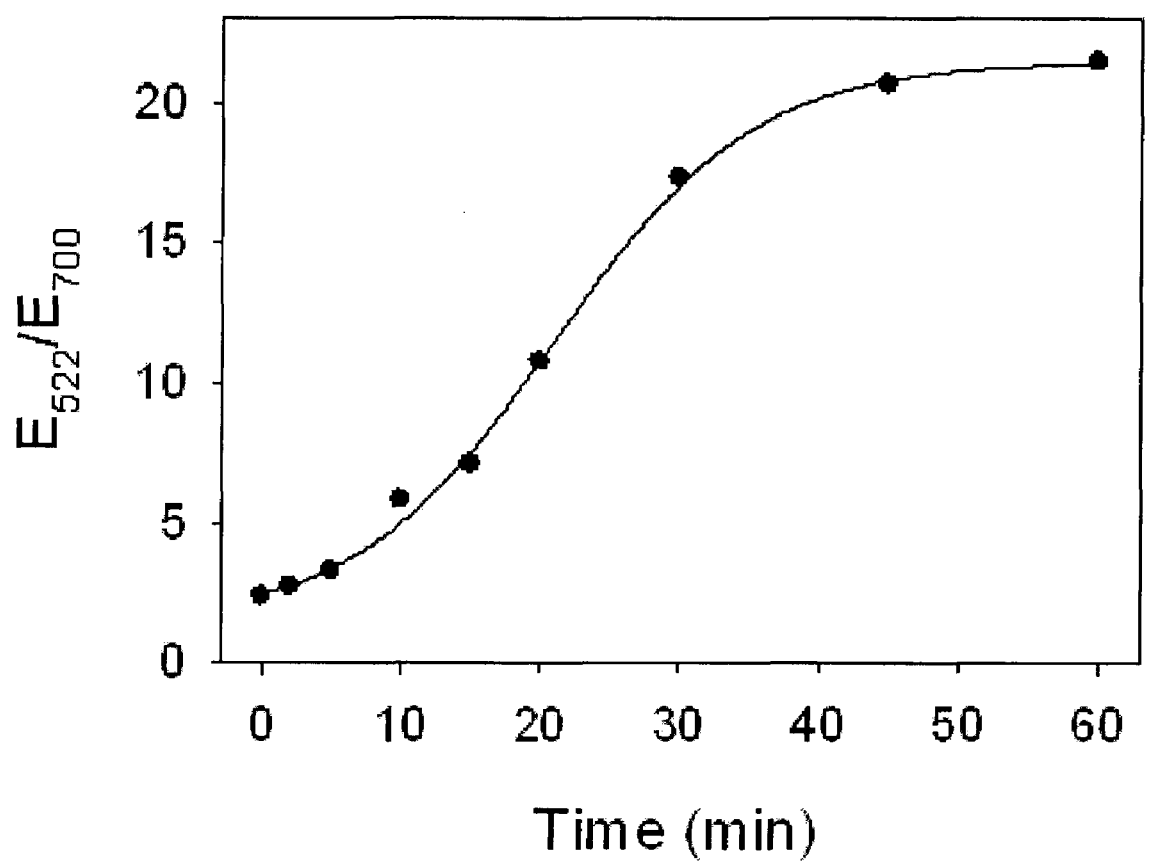
FIG. 7 shows the kinetics of color change of the aptazyme-gold particle sensor.

In the presence of only Mg(II), the rate constant of the aptazyme was $3.5 \times 10^{-3}$ $min^{-1}$ with 5 mM adenosine (Wang et al. 2002), thus requiring 200 minutes for 50% substrate cleavage. The "8-17" DNAzyme is at least 3000-fold more active in the presence of Pb(II) than Mg(II) under the same conditions (Brown et al., Li and Lu 2000, Li et al. 2000). Pb(II) was used in the system, in addition to Mg(II), to decrease detection time. FIG. 7 shows the kinetics of the color changes of the aptazyme-gold particle sensor monitored by the extinction ratio between 522 nm and 700 nm in the presence of 5 mM adenosine. The kinetics data can be fit to a sigmoidal curve, thus showing that the reaction progresses to a substantial extent in 30 minutes and is complete at 60 minutes. Small errors in timing (e.g., less than 1 minute) in the sensing operation would not result in large errors in observed particle aggregations and thus color changes.

Example 4

Sensitivity and Selectivity of the Sensor

Figure 8:
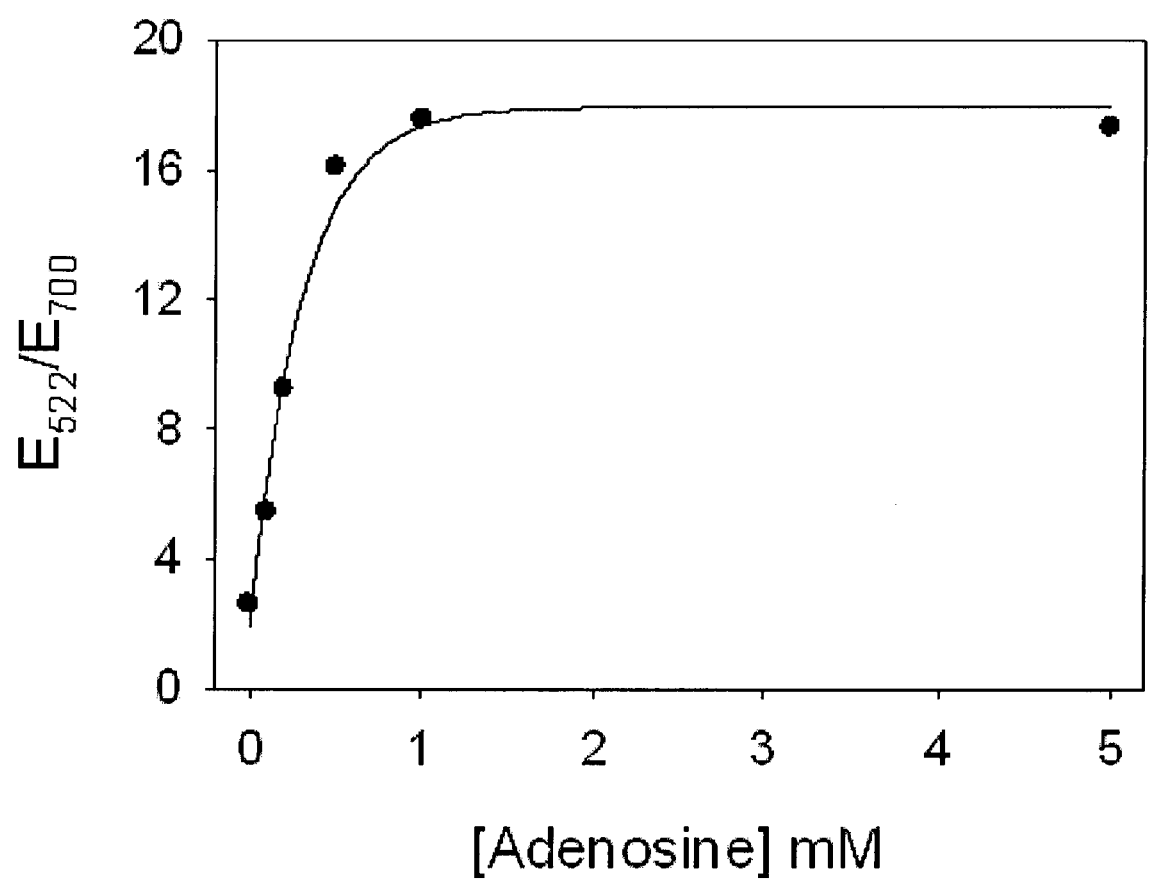
FIG. 8 shows the quantification of adenosine concentration using UV-vis spectroscopy.

Thirty minutes was chosen for the assay time to determine the sensitivity and selectivity of the sensor, this time was chosen to balance both the speed and the sensitivity of the sensor. FIG. 8 shows adenosine-dependent color changes; the spectra were obtained using a Hewlett-Packard 8453 spectrophotometer. Under these condition used, the sensitivity of the adenosine biosensor is 100 µM to 1 mM. Because the assay is kinetically-based, the detection range can be shifted by using different assay times.

To determine selectivity of the aptazyme-gold particle sensor, 5 mM uridine, cytosine or guanosine were used in the assay. Under these circumstances, only background signal was observed. The color difference can be conveniently monitored by spotting the resulting particles onto TLC plates. In this experiment, color progression was from blue to purple to red, corresponding to increasing adenosine concentrations. However, assays using 5 mM of gaunosine, cytidine or uridine show only blue color, the same as assays without any nucleosides added.

REFERENCES (References for Table 3B are Found Below)

Allara D, Nuzzo R. (1985) Spontaneously organized molecular assemblies. 1. Formation, dynamics and physical properties of n-alkanoic acids adsorbed from solution on an oxidized aluminum surface. *Langmuir* 1: 45-52.

Beebe T, Rabke-Clemmer C, (1995) Thiol labeling of DNA for attachment to gold surfaces. U.S. Pat. No. 5,472,881 USA.

Biroccio A, Hamm J, Incitti I, De Francesco R, Tomei L. (2002) Selection of RNA aptamers that are specific and high-affinity ligands of the hepatitis C virus RNA-dependent RNA polymerase. *J Virol* 76: 3688-3696.

Breaker R R, Joyce G F, Breaker R R, Joyce G F. (1995) A DNA enzyme with Mg(2+)-dependent RNA phosphoesterase activity.; A DNA enzyme that cleaves RNA. *Chem Biol; Chem Biol* 2; 1: 223-229.

Breaker R R, Joyce G F. (1994) A DNA enzyme that cleaves RNA. *Chem Biol* 1: 223-229.

Breaker R R. (2002) Engineered allosteric ribozymes as biosensor components. *Curr Opin Biotechnol* 13: 31-39.

Brody E N, Gold L. (2000) Aptamers as therapeutic and diagnostic agents. *J Biotechnol* 74: 5-13.

Brown A, Pavot C, Li J, Lu Y. A lead-dependent DNAzyme with a two-step mechanism. submitted.

Bruno J G, Kiel J L. (1999) In vitro selection of DNA aptamers to anthrax spores with electrochemiluminescence detection. *Biosens Bioelectron* 14: 457-464.

Bruno J G, Kiel J L. (2002) Use of magnetic beads in selection and detection of biotoxin aptamers by electrochemiluminescence and enzymatic methods. *Biotechniques* 32: 178-80, 182-3.

Cadwell R C, Joyce G F. (1992) Randomization of genes by PCR mutagenesis. *PCR Methods Appl* 2: 28-33.

Cadwell R C, Joyce G F. (1994) Mutagenic PCR. *PCR Methods Appl* 3: S136-40.

Cao Y, Jin R, Mirkin C A. (2001) DNA-modified core-shell Ag/Au particles. *J Am Chem Soc* 123: 7961-7962.

Carmi N, Shultz L A, Breaker R R. (1996) In vitro selection of self-cleaving DNAs. *Chem Biol* 3: 1039-1046.

Chaloin L, Lehmann M J, Sczakiel G, Restle T. (2002) Endogenous expression of a high-affinity pseudoknot RNA aptamer suppresses replication of HIV-1. *Nucleic Acids Res* 30: 4001-4008.

Chapman K B, Szostak J W. (1994) In vitro selection of catalytic RNAs. *Curr Opin Struct Biol* 4: 618-622.

Ciesiolka J, Gorski J, Yarus M. (1995) Selection of an RNA domain that binds Zn2+. *RNA* 1: 538-550.

Conaty J, Hendry P, Lockett T. (1999) Selected classes of minimised hammerhead ribozyme have very high cleavage rates at low Mg2+ concentration. *Nucleic Acids Res* 27: 2400-2407.

Conn M, Prudent J, Schultz P. (1996) Porphyrin Metallation Catalyzed by a Small RNA Molecule. *J Am Chem Soc* 118: 7012-7013.

Cuenoud B, Szostak J W. (1995) A DNA metalloenzyme with DNA ligase activity. *Nature* 375: 611-614.

Dai X, De Mesmaeker A, Joyce G F. (1995) Cleavage of an amide bond by a ribozyme. *Science* 267: 237-240.

Earnshaw, Gait. (1998) Modified oligoribonucleotides as site-specific probes of RNA structure and function. *Biopolymers* 48: 39-55.

Ekland E H, Bartel D P. (1996) RNA-catalysed RNA polymerization using nucleoside triphosphates. *Nature* 382: 373-376.

Ekland E H, Szostak J W, Bartel D P. (1995) Structurally complex and highly active RNA ligases derived from random RNA sequences. *Science* 269: 364-370.

Ellington A D, Szostak J W. (1990) In vitro selection of RNA molecules that bind specific ligands. *Nature* 346: 818-822.

Faulhammer D, Famulok M. (1997) *Angew Chem Int Ed Engl* 35: 2837-2841.

Geyer C R, Sen D. (1997) Evidence for the metal-cofactor independence of an RNA phosphodiester-cleaving DNA enzyme. *Chem Biol* 4: 579-593.

Grabar K, Freeman R, Hommer M, Natan M. (1995) Preparation and characterization of Au colloid Monolayers. *Anal. Chem.* 67: 735-743.

Hesselberth J, Robertson M P, Jhaveri S, Ellington A D. (2000) In vitro selection of nucleic acids for diagnostic applications. *J Biotechnol* 74: 15-25.

Hofmann H P, Limmer S, Hornung V, Sprinzl M. (1997) Ni2+-binding RNA motifs with an asymmetric purine-rich internal loop and a G-A base pair. *RNA* 3: 1289-1300.

Huizenga D E, Szostak J W. (1995) A DNA aptamer that binds adenosine and ATP. *Biochemistry* 34: 656-665.

Iler R. (1979) Chapter 6. In: anonymous (eds) *The chemistry of silica*. Wiley, N.Y.

Illangasekare M, Yarus M. (1997) Small-molecule-substrate interactions with a self-aminoacylating ribozyme. *J Mol Biol* 268: 631-639.

Jayasena S D. (1999) Aptamers: an emerging class of molecules that rival antibodies in diagnostics. *Clin Chem* 45: 1628-1650.

Jhaveri S, Kirby R, Conrad R, Maglott E, Bowser M, Kennedy R, Glick G, Ellington A. (2000) Designed signaling aptamers that transduce molecular recognition to changes in fluorescence intensity. *J. Am. Chem. Soc.* 122: 2469-2473.

Jhaveri S, Rajendran M, Ellington A D. (2000) In vitro selection of signaling aptamers. *Nat Biotechnol* 18: 1293-1297.

Joyce G F. (1994) In vitro evolution of nucleic acids. *Curr Opin Struct Biol* 4: 331-336.

Kiga D, Futamura Y, Sakamoto K, Yokoyama S. (1998) An RNA aptamer to the xanthine/guanine base with a distinctive mode of purine recognition. *Nucleic Acids Res* 26: 1755-1760.

Lauhon C T, Szostak J W. (1995) RNA aptamers that bind flavin and nicotinamide redox cofactors. *J Am Chem Soc* 117: 1246-1257.

Li J, Lu Y. (2000) A highly sensitive and selective catalytic DNA biosensor for lead ions. *J Am Chem Soc* 122: 10466-10467.

Li J, Zheng W, Kwon A H, Lu Y. (2000) In vitro selection and characterization of a highly efficient Zn(II)-dependent RNA-cleaving deoxyribozyme. *Nucleic Acids Res* 28: 481-488.

Li Y, Breaker R R. (1999) Phosphorylating DNA with DNA. *Proc Natl Acad Sci USA* 96: 2746-2751.

Li Y, Sen D. (1996) A catalytic DNA for porphyrin metallation. *Nat Struct Biol* 3: 743-7.

Link S, Wang Z, El-Sayed M. (1999) Alloy formation of gold-silver particles and the dependence of the plasmon absorption on their compositions. *J Phys Chem B* 103: 3529-3533.

Lohse P A, Szostak J W. (1996) Ribozyme-catalysed amino-acid transfer reactions. *Nature* 381: 442-444.

Lorsch J R, Szostak J W. (1994) In vitro evolution of new ribozymes with polynucleotide kinase activity. *Nature* 371: 31-36.

Lu Y, Liu J, SIMPLE CATALYTIC DNA BIOSENSORS FOR IONS BASED ON COLOR CHANGES, application Ser. No. 09/605,558, USA.

Lu Y. (2002) New transition-metal-dependent DNAzymes as efficient endonucleases and as selective metal biosensors. *Chemistry* 8: 4589-4596

Maoz R, Sagiv J. (1987) Penetration-controlled reactions in organized monolayer assemblies. 1. Aqueous permanganate interaction with monolayer and multilayer films of long-chain surfactants. *Langmuir* 3: 1034-1044.

Mirkin C A, Letsinger R L, Mucic R C, Storhoff J J. (1996) A DNA-based method for rationally assembling particles into macroscopic materials. *Nature* 382: 607-609.

Mirkin, C. A., Letsinger, L. R, Mucic, C. R, Storhoff, J. J, Elghanian R, (2002) Particles having polynucleotides attached thereto and uses therefor. U.S. Pat. No. 6,361,944 USA.

Mucic R, Herrlein M, Mirkin, C. A., Letsinger R. (1996) Synthesis and characterization of DNA with ferrocenyl groups attached to their 5'-termini: Electrochemical characterization of a redox-active nucleotide monolayer. *Chem. Commun.* 555.

Nuzzo R, Fusco F, Allara D. (1987) Spontaneously organized molecular assemblies, 3. Preparation and properties of solution adsorbed monolayers of organic disulfides on gold surfaces. *J Am Chem Soc* 109: 2358.

Piccirilli J A, McConnell T S, Zaug A J, Noller H F, Cech T R. (1992) Aminoacyl esterase activity of the Tetrahymena ribozyme. *Science* 256: 1420-1424.

Prudent J R, Uno T, Schultz P G. (1994) Expanding the scope of RNA catalysis. *Science* 264: 1924-1927.

Rakow N A, Suslick K S. (2000) A colorimetric sensor array for odour visualization. *Nature* 406: 710-713.

Robertson M P, Ellington A D. (1999) In vitro selection of an allosteric ribozyme that transduces analytes to amplicons. *Nat Biotechnol* 17: 62-66.

Roth A, Breaker R R. (1998) An amino acid as a cofactor for a catalytic polynucleotide. *Proc Natl Acad Sci USA* 95: 6027-6031.

Rusconi C P, Scardino E, Layzer J, Pitoc G A, Ortel T L, Monroe D, Sullenger B A. (2002) RNA aptamers as reversible antagonists of coagulation factor IXa. *Nature* 419: 90-94.

Santoro S W, Joyce G F. (1997) A general purpose RNA-cleaving DNA enzyme. *Proc Natl Acad Sci USA* 94: 4262-4266.

Seetharaman S, Zivarts M, Sudarsan N, Breaker R R. (2001) Immobilized RNA switches for the analysis of complex chemical and biological mixtures. *Nat Biotechnol* 19: 336-341.

Shaiu W L, Larson D D, Vesenka J, Henderson E. (1993) Atomic force microscopy of oriented linear DNA molecules labeled with 5 nm gold spheres. *Nucleic Acids Res* 21: 99-103.

Sillén L G, (1964) Stability constants of metal-ion complexes. Edition: 2d ed.

Smith J, Olson D, Armitage B. (1999) Molecular recognition of PNA-containing hybrids: Spontaneous assembly of helical cyanine dye aggregates on PNA templates. *J. Am. Chem. Soc.* 121: 2686-2695.

Soriaga M, Hubbard A. (1982) Determination of the orientation of aromatic molecules adsorbed on platinum electrodes: The influence of solute concentration. *J Am Chem Soc* 104.

Soukup G A, Breaker R R. (2000) Allosteric nucleic acid catalysts. *Curr Opin Struct Biol* 10: 318-325.

Stojanovic M N, Landry D W. (2002) Aptamer-based calorimetric probe for cocaine. *J Am Chem Soc* 124: 9678-9679.

Storhoff J, Elghanian R, Mucic R, Mirkin C, Letsinger R L. (1998) One-pot colorimetric differentiation of polynucleotides with single base imperfections using gold particle probes. *J Am Chem Soc* 120: 1959-1964.

Tang J, Breaker R R. (1997) Rational design of allosteric ribozymes. *Chem Biol* 4: 453-459.

Tang J, Breaker R R. (2000) Structural diversity of self-cleaving ribozymes. *Proc Natl Acad Sci USA* 97: 5784-5789.

Tarasow T M, Tarasow S L, Eaton B E. (1997) RNA-catalysed carbon-carbon bond formation. *Nature* 389: 54-57.

Timmons, Zisman. (1965) *J. Phys. Chem.* 69: 984-990.

Tompkins H, Allara D. (1974) The study of the gas-solid interaction of acetic acid with a cuprous oxide surface using reflection-absorption spectroscopy. *J. Colloid and Interface Sci.* 49410.

Tsang J, Joyce G F. (1996) In vitro evolution of randomized ribozymes. *Methods Enzymol* 267: 410-426.

Tuerk C, Gold L. (1990) Systematic evolution of ligands by exponential enrichment: RNA ligands to bacteriophage T4 DNA polymerase. *Science* 249: 505-510.

Vaish N K, Heaton P A, Fedorova O, Eckstein F. (1998) In vitro selection of a purine nucleotide-specific hammerheadlike ribozyme. *Proc Natl Acad Sci USA* 95: 2158-2162.

Wallace S T, Schroeder R. (1998) In vitro selection and characterization of streptomycin-binding RNAs: recognition discrimination between antibiotics. *RNA* 4: 112-123.

Wallis M G, Streicher B, Wank H, von Ahsen U, Clodi E, Wallace S T, Famulok M, Schroeder R. (1997) In vitro selection of a viomycin-binding RNA pseudoknot. *Chem Biol* 4: 357-366.

Wang D Y, Lai B H, Sen D. (2002) A general strategy for effector-mediated control of RNA-cleaving ribozymes and DNA enzymes. *J Mol Biol* 318: 33-43.

Wecker M, Smith D, Gold L. (1996) In vitro selection of a novel catalytic RNA: characterization of a sulfur alkylation reaction and interaction with a small peptide. *RNA* 2: 982-994.

Whitesides, (1995) Proceedings of the Robert A. Welch Foundation 39th Conference On Chemical Research Nanophase Chemistry., Houston, Tex.

Wiegand T W, Janssen R C, Eaton B E. (1997) Selection of RNA amide synthases. *Chem Biol* 4: 675-683.

Wilson C, Szostak J W. (1995) In vitro evolution of a self-alkylating ribozyme. *Nature* 374: 777-782.

Wilson D S, Szostak J W. (1999) In vitro selection of functional nucleic acids. *Annu Rev Biochem* 68: 611-647.

Zhang B, Cech T R. (1997) Peptide bond formation by in vitro selected ribozymes. *Nature* 390: 96-100.

Zillmann M, Limauro S E, Goodchild J. (1997) In vitro optimization of truncated stem-loop II variants of the hammerhead ribozyme for cleavage in low concentrations of magnesium under non-turnover conditions. *RNA* 3: 734-747.

REFERENCES for Table 3B

1. Ellington, A. D. & Conrad, R. (1995). Aptamers as potential nucleic acid pharmaceuticals. *Biotechnol. Annu. Rev.* 1: 185-214.
2. Jayasena, S. D. (1999). Aptamers: an emerging class of molecules that rival antibodies in diagnostics. *Clin. Chem.* (Washington, D.C.) 45: 1628-50.
3. Sun, L. Q., Cairns, M. J., Saravolac, E. G., Baker, A. & Gerlach, W. L. (2000). Catalytic nucleic acids: From lab to applications. *Pharmacol. Rev.* 52: 325-47.
4. Hesselberth, J., Robertson, M. P., Jhaveri, S. & Ellington, A. D. (2000). In vitro selection of nucleic acids for diagnostic applications. *Rev. Mol. Biotechnol.* 74: 15-25.
5. Joyce, G. F. (1999). Reactions Catalyzed by RNA and DNA Enzymes. In *The RNA World*, vol. 37 (Gesteland, R. F., Cech, T. R. & Atkins, J. F., ed.), pp. 687-9, Cold Spring Harbor Laboratory Press, Cold Spring Harbor, N.Y.
6. Breaker, R. R. (1997). DNA enzymes. *Nat. Biotechnol.* 15: 427-31.
7. Sen, D. & Geyer, C. R. (1998). DNA enzymes. *Curr. Opin. Chem. Biol.* 2: 680-7.
8. Breaker, R. R. (1999). Catalytic DNA: in training and seeking employment. *Nat. Biotechnol.* 17: 422-3.
9. Breaker, R. R. (2000). Making catalytic DNAs. *Science* (Washington, D.C.) 290: 2095-6.
10. Derose, V. J. (2002). Two Decades of RNA Catalysis. *Chemistry & Biology* 9: 961-9.
11. Ellington, A. D. & Szostak, J. W. (1990). In vitro selection of RNA molecules that bind specific ligands. *Nature* (London) 346: 818-22.
12. Ellington, A. D. & Szostak, J. W. (1992). Selection in vitro of single-stranded DNA molecules that fold into specific ligand-binding structures. *Nature* (London) 355: 850-2.
13. Santoro, S. W. & Joyce, G. F. (1997). A general purpose RNA-cleaving DNA enzyme. *Proc. Natl. Acad. Sci. U.S.A.* 94: 4262-6.
14. Faulhammer, D. & Famulok, M. (1996). The Ca2+ ion as a cofactor for a novel RNA-cleaving deoxyribozyme. *Angew. Chem., Int. Ed. Engl.* 35: 2837-41.
15. Li, J., Zheng, W., Kwon, A. H. & Lu, Y. (2000). In vitro selection and characterization of a highly efficient Zn(II)-dependent RNA-cleaving deoxyribozyme. *Nucleic Acids Res.* 28: 481-8.
16. Jenison, R. D., Gill, S. C., Pardi, A. & Polisky, B. (1994). High-resolution molecular discrimination by RNA. *Science* (Washington, DC, United States) 263: 1425-9.
17. Santoro, S. W. & Joyce, G. F. (1998). Mechanism and utility of an RNA-cleaving DNA enzyme. *Biochemistry* 37: 13330-42.
18. Mannironi, C., Di Nardo, A., Fruscoloni, P. & Tocchini-Valentini, G. P. (1997). In vitro selection of dopamine RNA ligands. *Biochemistry* 36: 9726-34.
19. Sigurdsson, S. T., Thomson, J. B. & Eckstein, F. (1998). Small ribozymes. *Cold Spring Harbor Monogr. Ser.* 35: 339-76.
20. Stage-Zimmermann, T. K. & Uhlenbeck, O. C. (1998). Hammerhead ribozyme kinetics. *RNA* 4: 875-89.
21. Werstuck, G. & Green, M. R. (1998). Controlling gene expression in living cells through small molecule-RNA interactions. *Science* (Washington, D. C.) 282: 296-8.
22. Walter, N. G. & Burke, J. M. (1998). The hairpin ribozyme: structure, assembly and catalysis. *Curr. Opin. Chem. Biol.* 2: 24-30.
23. Holeman, L. A., Robinson, S. L., Szostak, J. W. & Wilson, C. (1998). Isolation and characterization of fluorophore-binding RNA aptamers. *Folding Des.* 3: 423-31.
24. Wilson, C. & Szostak, J. W. (1998). Isolation of a fluorophore-specific DNA aptamer with weak redox activity. *Chem. Biol.* 5: 609-17.
25. Pan, T. & Uhlenbeck, O. C. (1992). A small metalloribozyme with a two-step mechanism. *Nature* 358: 560-3.
26. Yang, Q., Goldstein, I. J., Mei, H.-Y. & Engelke, D. R. (1998). DNA ligands that bind tightly and selectively to cellobiose. *Proc. Natl. Acad. Sci. U.S.A.* 95: 5462-7.
27. Been, M. D. & Wickham, G. S. (1997). Self-cleaving ribozymes of hepatitis delta virus RNA. *Eur. J. Biochem.* 247: 741-53.
28. Tanner, N. K. (1998). Biochemistry of hepatitis delta virus catalytic RNAs. *Ribozymes Gene Ther. Cancer*: 23-38.
29. Famulok, M. & Szostak, J. W. (1992). Stereospecific recognition of tryptophan agarose by in vitro selected RNA. *J. Am. Chem. Soc.* 114: 3990-1.
30. Cech, T. R. (1993). Structure and mechanism of the large catalytic RNAs: group I and group II introns and ribonuclease P. In *The RNA World* (Gesteland, R. F. & Atkins, J. F., ed.), pp. 239-70, Cold Spring Harbor Laboratory Press, Cold Spring Harbor, N.Y.
31. Cech, T. R. & Herschlag, D. (1996). Group I ribozymes: substrate recognition, catalytic strategies, and comparative mechanistic analysis. *Nucleic Acids Mol. Biol.* 10: 1-17.
32. Famulok, M. (1994). Molecular Recognition of Amino Acids by RNA-Aptamers: An L-Citrulline Binding RNA Motif and Its Evolution into an L-Arginine Binder. *J. Am. Chem. Soc.* 116: 1698-706.
33. Geiger, A., Burgstaller, P., Von Der Eltz, H., Roeder, A. & Famulok, M. (1996). RNA aptamers that bind L-arginine with sub-micromolar dissociation constants and high enantioselectivity. *Nucleic Acids Res.* 24: 1029-36.
34. Tao, J. & Frankel, A. D. (1996). Arginine-Binding RNAs Resembling TAR Identified by in Vitro Selection. *Biochemistry* 35: 2229-38.
35. Connell, G. J., Illangesekare, M. & Yarus, M. (1993). Three small ribooligonucleotides with specific arginine sites. *Biochemistry* 32: 5497-502.
36. Burgstaller, P., Kochoyan, M. & Famulok, M. (1995). Structural probing and damage selection of citrulline- and arginine-specific RNA aptamers identify base positions required for binding. *Nucleic Acids Res.* 23: 4769-76.
37. Nolte, A., Klussmann, S., Bald, R., Erdmann, V. A. & Fuerste, J. P. (1996). Mirror-design of L-oligonucleotide ligands binding to L-arginine. *Nature Biotechnology* 14: 1116-9.
38. Valadkhan, S. & Manley, J. L. (2001). Splicing-related catalysis by protein-free snRNAs. *Nature* (London, United Kingdom) 413: 701-7.
39. Nissen, P., Hansen, J., Ban, N., Moore, P. B. & Steitz, T. A. (2000). The structural basis of ribosome activity in peptide bond synthesis. *Science* (Washington, D.C.) 289: 920-30.
40. Harada, K. & Frankel, A. D. (1995). Identification of two novel arginine binding DNAs. *EMBO J.* 14: 5798-811.
41. Carmi, N., Balkhi, H. R. & Breaker, R. R. (1998). Cleaving DNA with DNA. *Proc. Natl. Acad. Sci. U.S.A.* 95: 2233-7.
42. Majerfeld, I. & Yarus, M. (1994). An RNA pocket for an aliphatic hydrophobe. *Nat. Struct. Biol.* 1: 287-92.
43. Cuenoud, B. & Szostak, J. W. (1995). A DNA metalloenzyme with DNA ligase activity. *Nature* 375: 611-4.
44. Majerfeld, I. & Yarus, M. (1998). Isoleucine:RNA sites with associated coding sequences. *Rna* 4: 471-8.

45. Li, Y. & Breaker, R. R. (1999). Phosphorylating DNA with DNA. *Proc. Natl. Acad. Sci. U.S.A.* 96: 2746-51.
46. Sassanfar, M. & Szostak, J. W. (1993). An RNA motif that binds ATP. *Nature* (London) 364: 550-3.
47. Burgstaller, P. & Famulok, M. (1994). Isolation of RNA aptamers for biological cofactors by in vitro selection. *Angew. Chem.* 106: 1163-6 (See also Angew. Chem., Int. Ed. Engl., 994, 33(10), 084-7).
48. Burke, D. H. & Gold, L. (1997). RNA aptamers to the adenosine moiety of S-adenosyl methionine: structural inferences from variations on a theme and the reproducibility of SELEX. *Nucleic Acids Res.* 25: 2020-4.
49. Huizenga, D. E. & Szostak, J. W. (1995). A DNA Aptamer That Binds Adenosine and ATP. *Biochemistry* 34: 656-65.
50. Klussmann, S., Nolte, A., Bald, R., Erdmann, V. A. & Fuerste, J. P. (1996). Mirror-image RNA that binds D-adenosine. *Nat. Biotechnol.* 14: 1112-5.
51. Burmeister, J., Von Kiedrowski, G. & Ellington, A. D. (1997). Cofactor-assisted self-cleavage in DNA libraries with a 3'-'5'-phosphoramidate bond. *Angew. Chem., Int. Ed. Engl.* 36: 1321-4.
52. Connell, G. J. & Yarus, M. (1994). RNAs with dual specificity and dual RNAs with similar specificity. *Science* (Washington, D.C.) 264: 1137-41.
53. Li, Y. & Sen, D. (1996). A catalytic DNA for porphyrin metallation. *Nat. Struct. Biol.* 3: 743-7.
54. Lauhon, C. T. & Szostak, J. W. (1995). RNA aptamers that bind flavin and nicotinamide redox cofactors. *J. Am. Chem. Soc.* 117: 1246-57.
55. Travascio, P., Bennet, A. J., Wang, D. Y. & Sen, D. (1999). A ribozyme and a catalytic DNA with peroxidase activity: active sites versus cofactor-binding sites. *Chemistry & Biology* 6: 779-87.
56. Lorsch, J. R. & Szostak, J. W. (1994). In vitro selection of RNA aptamers specific for cyanocobalamin. *Biochemistry* 33: 973-82.
57. Rink, S. M., Shen, J.-C. & Loeb, L. A. (1998). Creation of RNA molecules that recognize the oxidative lesion 7,8-dihydro-8-hydroxy-2'-deoxyguanosine (8-oxodG) in DNA. *Proc. Natl. Acad. Sci. U.S.A.* 95: 11619-24.
58. Haller, A. A. & Samow, P. (1997). In vitro selection of a 7-methyl-guanosine binding RNA that inhibits translation of capped mRNA molecules. *Proc. Natl. Acad. Sci. U.S.A.* 94: 8521-6.
59. Kiga, D., Futamura, Y., Sakamoto, K. & Yokoyama, S. (1998). An RNA aptamer to the xanthine/guanine base with a distinctive mode of purine recognition. *Nucleic Acids Res.* 26: 1755-60.
60. Lato, S. M., Boles, A. R. & Ellington, A. D. (1995). In vitro selection of RNA lectins: Using combinatorial chemistry to interpret ribozyme evolution. *Chem. Biol.* 2: 291-303.
61. Wang, Y., Killian, J., Hamasaki, K. & Rando, R. R. (1996). RNA Molecules That Specifically and Stoichiometrically Bind Aminoglycoside Antibiotics with High Affinities. *Biochemistry* 35: 12338-46.
62. Wallis, M. G., Von Ahsen, U., Schroeder, R. & Famulok, M. (1995). A novel RNA motif for neomycin recognition. *Chem. Biol.* 2: 543-52.
63. Famulok, M. & Huettenhofer, A. (1996). In Vitro Selection Analysis of Neomycin Binding RNAs with a Mutagenized Pool of Variants of the 16S rRNA Decoding Region. *Biochemistry* 35: 4265-70.
64. Wallis, M. G., Streicher, B., Wank, H., Von Ahsen, U., Clodi, E., Wallace, S. T., Famulok, M. & Schroeder, R. (1997). In vitro selection of a viomycin-binding RNA pseudoknot. *Chem. Biol.* 4: 357-66.
65. Burke, D. H., Hoffman, D. C., Brown, A., Hansen, M., Pardi, A. & Gold, L. (1997). RNA aptamers to the peptidyl transferase inhibitor chloramphenicol. *Chem. Biol.* 4: 833-43.
66. Wallace, S. T. & Schroeder, R. (1998). In vitro selection and characterization of streptomycin-binding RNAs: recognition discrimination between antibiotics. *Rna* 4: 112-23.
67. Giver, L., Bartel, D. P., Zapp, M. L., Green, M. R. & Ellington, A. D. (1993). Selection and design of high-affinity RNA ligands for HIV-1 Rev. *Gene* 137: 19-24.
68. Giver, L., Bartel, D., Zapp, M., Pawul, A., Green, M. & Ellington, A. D. (1993). Selective optimization of the Rev-binding element of HIV-1. *Nucleic Acids Res.* 21: 5509-16.
69. Williams, K. P., Liu, X.-H., Schumacher, T. N. M., Lin, H. Y., Ausiello, D. A., Kim, P. S. & Bartel, D. P. (1997). Bioactive and nuclease-resistant L-DNA ligand of vasopressin. *Proc. Natl. Acad. Sci. U.S.A.* 94: 11285-90.
70. Zimmerman, J. M. & Maher, L. J., Iii (2002). In vivo selection of spectinomycin-binding RNAs. *Nucleic Acids Res.* 30: 5425-35.
71. Vianini, E., Palumbo, M. & Gatto, B. (2001). In vitro selection of DNA aptamers that bind L-tyrosinamide. *Bioorganic & Medicinal Chemistry* 9: 2543-8.
72. Andreola, M.-L., Pileur, F., Calmels, C., Ventura, M., Tarrago-Litvak, L., Toulme, J.-J. & Litvak, S. (2001). DNA aptamers selected against the HIV-1 RNase H display in vitro antiviral activity. *Biochemistry* 40: 10087-94.
73. Fukusaki, E.-I., Kato, T., Maeda, H., Kawazoe, N., Ito, Y., Okazawa, A., Kajiyama, S.-I. & Kobayashi, A. (2000). DNA aptamers that bind to chitin. *Bioorg. Med. Chem. Lett.* 10: 423-5.
74. Bock, L. C., Griffin, L. C., Latham, J. A., Verrnaas, E. H. & Toole, J. J. (1992). Selection of single-stranded DNA molecules that bind and inhibit human thrombin. *Nature* (London) 355: 564-6.
75. Koizumi, M. & Breaker, R. R. (2000). Molecular Recognition of cAMP by an RNA Aptamer. *Biochemistry* 39: 8983-92.
76. Kato, T., Takemura, T., Yano, K., Ikebukuro, K. & Karube, I. (2000). In vitro selection of DNA aptamers which bind to cholic acid. *Biochim. Biophys. Acta* 1493: 12-8.
77. Okazawa, A., Maeda, H., Fukusaki, E., Katakura, Y. & Kobayashi, A. (2000). In vitro selection of hematoporphyrin binding DNA aptamers. *Bioorg. Med. Chem. Lett.* 10: 2653-6.
78. Kawakami, J., Imanaka, H., Yokota, Y. & Sugimoto, N. (2000). In vitro selection of aptamers that act with Zn2+. *J. Inorg. Biochem.* 82: 197-206.
79. Bruno, J. G. & Kiel, J. L. (1999). In vitro selection of DNA aptamers to anthrax spores with electrochemiluminescence detection. *Biosensors & Bioelectronics* 14: 457-64.

The invention claimed is:

1. A sensor system for detecting an effector, comprising:
   (i) an aggregate, wherein the aggregate comprises a plurality of complexes wherein each complex comprises:
   (I) an aptazyme, comprising an aptamer comprising a binding site for the effector,
   (II) a substrate for the aptazyme, hybridized to the aptazyme,
   (III) particles,
   (IV) polynucleotides attached to the particles at the 5' terminus or 3' terminus and hybridized to the substrate,
   wherein the aptazyme cleaves the substrate when the aptamer binds the effector and cleavage of the substrate results in deaggregation of the aggregate.

2. A sensor system for detecting an effector, comprising:
   (i) an aggregate, wherein the aggregate comprises a plurality of complexes wherein each complex comprises:
   (I) an aptazyme, comprising an aptamer comprising a binding site for the effector,
   (II) a substrate for the aptazyme, hybridized to the aptazyme,
   (III) gold particles,
   (IV) polynucleotides attached to the particles at the 5'-terminus or 3'-terminus, and hybridized to the substrate, and
   (ii) Mg(II),
   wherein the aptazyme comprises DNA,
   the aptazyme cleaves the substrate when the aptamer binds the effector and cleavage of the substrate results in deaggregation of the aggregate.

3. A sensor system for detecting an effector, comprising:
   (i) an aggregate, wherein the aggregate comprises a plurality of complexes wherein each complex comprises:
   (I) an aptazyme, comprising an aptamer comprising a binding site for the effector,
   (II) a substrate for the aptazyme, hybridized to the aptazyme,
   (III) first particles,
   (IV) first polynucleotides attached to the first particles at the 5'-terminus or 3'-terminus and hybridized to the substrate;
   (V) second particles,
   (VI) second polynucleotides attached to the second particles at the 5'-terminus or 3'-terminus and hybridized to the substrate, wherein the aptazyme cleaves the substrate when the aptamer binds the effector and cleavage of the substrate results in deaggregation of the aggregate.

4. The sensor system of claim 1, wherein the aptazyme comprises DNA.

5. The sensor system of claim 1, wherein the effector is adenosine.

6. The sensor system of claim 1, wherein the particles comprise gold particles.

7. The sensor system of claim 1, wherein the particles comprise a material selected from the group consisting of metal colloids, semiconductor colloids and polystyrene latex particles.

8. The sensor system of claim 2, further comprising Pb(II).

9. The sensor system of claim 3, wherein the aptazyme comprises DNA.

10. The sensor system of claim 3, wherein the effector is adenosine.

11. The sensor system of claim 3, wherein the first and second particles comprise gold particles.

12. The sensor system of claim 3, wherein the first and second particles comprise a material selected from the group consisting of metal colloids, semiconductor colloids and polystyrene latex particles.

13. The sensor system of claim 3, wherein the first and second polynucleotides have identical sequences.

14. The sensor system of claim 3, wherein the first and second polynucleotides have different sequences.

15. The sensor system of claim 1, wherein the effector activates the aptazyme.

16. The sensor system of claim 1, wherein the effector inhibits the aptazyme.

17. The sensor system of claim 2, wherein the effector activates the aptazyme.

18. The sensor system of claim 2, wherein the effector inhibits the aptazyme.

19. The sensor system of claim 3, wherein the effector activates the aptazyme.

20. The sensor system of claim 3, wherein the effector inhibits the aptazyme.

* * * * *

UNITED STATES PATENT AND TRADEMARK OFFICE
CERTIFICATE OF CORRECTION

| | |
|---|---|
| PATENT NO. | : 7,612,185 B2 |
| APPLICATION NO. | : 10/384497 |
| DATED | : November 3, 2009 |
| INVENTOR(S) | : Yi Lu and Juewen Liu |

It is certified that error appears in the above-identified patent and that said Letters Patent is hereby corrected as shown below:

Other Publications:

Page 2
Col. 2, line 39, please delete "RAN" and insert --RNA--.
Col. 2, line 64, please delete "Deoxyribozyme$_2$" and insert --Deoxyribozyme,--.

Page 3
Col. 1, line 10, please delete "Homier" and insert --Hommer--.

Page 6
Col. 1, line 27, please delete ".concentration" and insert --concentration--.
Col. 2, line 33, please delete "Ca$^{2+}$ion" and insert --Ca$^{2+}$ ion--.

Page 12
Col. 2, line 10, please delete "Cu$^{2+}$based" and insert --Cu$^{2+}$ based--.
Col. 2, line 14, please delete "Cu$^{2+}$based" and insert --Cu$^{2+}$ based--.

Page 13
Col. 1, line 23, please delete "Hg$^{2+}$in" and insert --Hg$^{2+}$ in--.
Col. 1, line 44, please delete "Hg$^{2+}$in" and insert --Hg$^{2+}$ in--.
Col. 1, line 45, please delete "Jouranl" and insert --Journal--.
Col. 1, line 50, please delete "Hg$^{2+}$in" and insert --Hg$^{2+}$ in--.
Col. 1, line 58, please delete "No. 9, 4" and insert --No. 4--.
Col. 2, line 7, please delete "highly" and insert --Highly--.
Col. 2, line 35, please delete "Snesors" and insert --Sensors--.
Col. 2, line 43, please delete "Hg$^{2+}$ion" and insert --Hg$^{2+}$ ion--.

Page 15
Col. 1, line 67, please delete "pepride" and insert --peptide--.

Signed and Sealed this

Seventeenth Day of August, 2010

David J. Kappos
*Director of the United States Patent and Trademark Office*